US008742158B2

(12) United States Patent
Stranix et al.

(10) Patent No.: US 8,742,158 B2
(45) Date of Patent: Jun. 3, 2014

(54) PROTEASE INHIBITORS

(71) Applicant: TaiMed Biologics, Inc., Taipei (TW)

(72) Inventors: Brent R. Stranix, Pointe-Claire (CA); Jean-Francois Lavallee, Montreal (CA); Nicolas Leberre, Montreal (CA); Valerie Perron, Laval (CA); Dominik Herbart, Blainville (CA); Guy Milot, Longueuil (CA); Chandra Panchal, Dollard-des-Ormeaux (CA)

(73) Assignee: TaiMed Biologies, Inc., Taipei (TW)

( * ) Notice: Subject to any disclaimer, the term of this patent is extended or adjusted under 35 U.S.C. 154(b) by 0 days.

(21) Appl. No.: 13/768,779

(22) Filed: Feb. 15, 2013

(65) Prior Publication Data

US 2013/0158261 A1 Jun. 20, 2013

Related U.S. Application Data

(62) Division of application No. 12/311,122, filed as application No. PCT/IB2007/004453 on Sep. 20, 2007, now Pat. No. 8,410,300.

(60) Provisional application No. 60/846,084, filed on Sep. 21, 2006.

(51) Int. Cl.
*C07C 311/41* (2006.01)

(52) U.S. Cl.
CPC .................................... *C07C 311/41* (2013.01)
USPC ............................................................ 560/13

(58) Field of Classification Search
None
See application file for complete search history.

(56) References Cited

U.S. PATENT DOCUMENTS

| | | | |
|---|---|---|---|
| 5,013,861 | A | 5/1991 | Weller, III et al. |
| 5,527,829 | A | 6/1996 | Kalish |
| 5,614,522 | A | 3/1997 | Talley et al. |
| 5,714,605 | A | 2/1998 | Vazquez et al. |
| 5,776,718 | A | 7/1998 | Palmer et al. |
| 5,965,588 | A | 10/1999 | Vazquez et al. |
| 5,985,870 | A | 11/1999 | Getman et al. |
| 6,022,994 | A | 2/2000 | Vazquez et al. |
| 6,127,372 | A | 10/2000 | Tung et al. |
| 6,159,995 | A | 12/2000 | Thorwart et al. |
| 6,384,036 | B1 | 5/2002 | Freskos et al. |
| 6,436,989 | B1 | 8/2002 | Hale et al. |
| 6,455,587 | B1 | 9/2002 | Bouzide et al. |
| 6,506,786 | B2 | 1/2003 | Stranix et al. |
| 6,528,532 | B1 | 3/2003 | Stranix et al. |
| 6,528,655 | B1 | 3/2003 | N'Zemba et al. |
| 6,608,100 | B1 | 8/2003 | Stranix et al. |
| 6,610,689 | B2 | 8/2003 | Stranix et al. |
| 6,632,816 | B1 | 10/2003 | Stranix et al. |
| 6,638,921 | B1 | 10/2003 | Sauve et al. |
| 6,656,965 | B2 | 12/2003 | Stranix et al. |
| 6,677,367 | B2 | 1/2004 | Stranix et al. |
| 6,703,403 | B2 | 3/2004 | Norbeck et al. |
| 7,388,008 | B2 | 6/2008 | Stranix et al. |
| 8,008,297 | B2 | 8/2011 | Stranix et al. |
| 8,227,450 | B2 | 7/2012 | Milot et al. |
| 2005/0171038 | A1 | 8/2005 | Hammond et al. |
| 2006/0287316 | A1 | 12/2006 | Wu et al. |
| 2009/0118339 | A1 | 5/2009 | Jonckers et al. |
| 2009/0253926 | A1 | 10/2009 | Milot et al. |
| 2010/0130765 | A1 | 5/2010 | Milot et al. |
| 2011/0178120 | A1 | 7/2011 | Stranix et al. |
| 2011/0184028 | A1 | 7/2011 | Stranix et al. |
| 2012/0053139 | A1 | 3/2012 | Wu et al. |

FOREIGN PATENT DOCUMENTS

| | | | |
|---|---|---|---|
| CA | 2 089 747 | A1 | 4/1992 |
| CA | 2 077 948 | A1 | 3/1993 |
| CA | 2 316 218 | A1 | 7/1999 |
| EP | 0 532 466 | A2 | 3/1993 |
| JP | 06321950 | A | 11/1994 |
| WO | WO-92/06998 | A1 | 4/1992 |
| WO | WO-95/06998 | A1 | 3/1995 |
| WO | WO-95/24385 | A1 | 9/1995 |
| WO | WO-97/27180 | A1 | 7/1997 |
| WO | WO-98/31664 | A1 | 7/1998 |
| WO | WO-99/33815 | A1 | 7/1999 |
| WO | WO-99/55687 | A2 | 11/1999 |
| WO | WO-00/47551 | A2 | 8/2000 |
| WO | WO-01/68593 | A2 | 9/2001 |
| WO | WO-01/76961 | A1 | 10/2001 |
| WO | WO-02/064551 | A1 | 8/2002 |
| WO | WO-03/074467 | A2 | 9/2003 |
| WO | WO-2004/054586 | A1 | 7/2004 |
| WO | WO-2004/056764 | A1 | 7/2004 |
| WO | WO-2005/066131 | A1 | 7/2005 |

(Continued)

OTHER PUBLICATIONS

Anderson et al., "The Use of Esters of N-Hydroxysuccinimide in Peptide Synthesis," *J. Am. Chem. Soc.* 86(9):1839-1842 (1964).

(Continued)

*Primary Examiner* — Alicia L Otton

(74) *Attorney, Agent, or Firm* — Clark & Elbing LLP

(57) ABSTRACT

The present invention provides HIV protease inhibitors of formulas I, IA, IB, Ib or II, or pharmaceutically acceptable salts thereof, wherein $R_2$ may be, for example, 2-pyridyl-$CH_2$—, 3-pyridyl-$CH_2$—, 4-pyridyl-$CH_2$—, a sulfonyl group as described in the formulas herein including benzenesulfonyl or thiophenesulfonyl groups, $R_{2a}$—CO)—, $R_{2a}$ being selected from the group consisting of piperonyl, 2-pyranzinyl (unsubstituted or substituted with H, or an alkyl of 1 to 4 carbon atoms) or a picolylamine group as described herein, wherein R3 may be, for example, a phenyl group or diphenylmethyl group as described herein, and wherein Cx may be, for example, COOH, $CONR_5R_6$, $CH_2OH$ or $CH_2OR_7$.

1 Claim, No Drawings

(56) References Cited

FOREIGN PATENT DOCUMENTS

| | | | |
|---|---|---|---|
| WO | WO-2006/012725 | A1 | 2/2006 |
| WO | WO-2006/114001 | A1 | 11/2006 |
| WO | WO-2007/062526 | A1 | 6/2007 |
| WO | WO-2008/078200 | A2 | 7/2008 |
| WO | WO-2009/148600 | A2 | 12/2009 |

OTHER PUBLICATIONS

Andrade et al., "HIV-Related Drug Metabolism and Cytochrome P450 Enzymes," *AIDS Clin. Care* 12(11):91-95 (2000).

Bouzide et al., "Lysine Derivatives as Potent HIV Protease Inhibitors. Discovery, Synthesis and Structure-Activity Relationship Studies," *Bioorg. Med. Chem. Lett.* 15:1509-1513 (2005).

Boyle et al., "Asymmetric Transformation of α-Amino-ϵ-Caprolactam, a Lysine Precursor," *J. Org. Chem.* 44(26):4841-4847 (1979).

Bukrinsky et al., "Active Nuclear Import of Human Immunodeficiency Virus Type 1 Preintegration Complexes," *Proc. Natl. Acad. Sci. USA* 89(14):6580-6584 (1992).

Calogeropoulou et al., "Strategies in the Design of Prodrugs of an Anti-HIV Agents," *Current Topics in Medicinal Chemistry* 3:1467-1495 (2003).

CASRN 612547-11-2. Entered STN Nov. 4, 2003. Accessed Mar. 22, 2012.

Chemical Abstracts, 123(7), Abstract 83099w (1995), Harada and Mikio, *Jpn. Kokai Tokkyo Koho* JP 06,321,950, Takeda Chemical Industries, Ltd. (1994).

Chemical Abstracts, 46(13), Abstract 6593c (1952), lzumiya, *J. Chem. Soc. Japan, Pure Chem. Sect.*, 72:149-152 (1951).

Chemical Abstracts, 46(13), Abstract 6593g (1952), lzumiya, *J. Chem. Soc. Japan, Pure Chem. Sect.*, 72:445-447 (1951).

Chemical Abstracts, 46(13), Abstract 6593i (1952), lzumiya, *J. Chem. Soc. Japan, Pure Chem. Sect.*, 72:550-552 (1951).

Chemical Abstracts, 62(2), Abstract 1740c (1965), Hermann, et al., *Peptides Proc. European Symp., 5th, Oxford*, 171-175 (1962).

Chong et al., "Peptidomimetic HIV Protease Inhibitors: Phosphate Prodrugs with Improved Biological Activities," *J. Med. Chem.* 36(17):2575-2577 (1993).

Dandache et al., "In Vitro Antiviral Activity and Cross-Resistance Profile of PL-100, A Novel Protease Inhibitor of Human Immunodeficiency Virus Type 1," *Antimicrob. Agents Chemother.* 51(11):4036-4043 (2007).

Dankwardt et al., "Amino Acid Derived Sulfonamide Hydroxamates as Inhibitors of Procollagen C-Proteinase. Part 2: Solid-Phase Optimization of Side Chains," *Bioorg. Med. Chem. Lett.* 12:1233-1235 (2002).

El-Nagger et al., "Synthesis and Biological Activity of Some New Quinoline-8-Sulphonylamino Acid and Dipeptide Derivatives," *Acta Pharm. Jugosl.* 33(2):103-110 (1983).

El-Nagger et al., "Synthesis of Nitrobenzene- and Nitroluensulfonylamino Acid and Dipeptide Derivatives," *Pol. J. Chem.* 52(3):637-642 (1978).

Elmore et al., "Kinetics and Mechanism of Catalysis of Proteolytic Enzymes," *Biochem. J.* 102:728-734 (1967).

Ettmayer et al., Lessons Learned from Marketed and Investigational Prodrugs, *Journal of Medicinal Chemistry* 47(10):2393-2404 (2004).

Fitzsimmons et al., "Selective Biotransformation of the Human Immunodeficiency Virus Protease Inhibitor Saquinavir by Human Small-Intestinal Cytochrome P4503A4," *Drug. Metab. Disp.* 25(2):256-266 (1997).

Galley et al., "HIV-1 Infection of Nondividing Cells: C-Terminal Tyrosine Phosphorylation of the Viral Matrix Protein is a Key Regulator," *Cell* 80(3):379-388 (1995).

Garrity et al., "A New Synthetic Route to 2-(P-Nitrobenzyl)-1, 4, 7, 10-Tetraazacyclododecane," *Tetrahedron Letters* 34(35):5531-5534 (1993).

Goff, "Retroviral Reverse Transcriptase: Synthesis, Structure, and Function," *Journal of Acquired Immune Deficiency Syndromes* 3(8):817-831 (1990).

Greene and Wuts, "Protection for the Amino Group," *Protective Groups in Organic Synthesis* 3rd Ed. 518-525 (John Wiley & Sons, Inc. 1999).

Greene, "Protection for the Amino Group," *Protective Groups in Organic Synthesis* 258-263 (John Wiley & Sons, Inc. 1981).

Hamill et al., "Non-Peptide Fibrinogen Receptor Antagonists. Synthesis of [3H]L-756,568," *J. Labelled Cpd. Radiopharm.* 42(6):605-609 (1999).

Haseltine, "Molecular Biology of the Human Immunodeficieny Virus Type 1," *The FASEB Journal* 5(10):2349-2360 (1991).

Hlavacek et al., "An Alternative Route to Nα-Methylamino Acid Derivatives: Synthesis and Conformation of Some Nα-Acetyl- Nα-Methylamino Acid Methylamides," *Collection Czech. Chem. Commun.* 53:2473-2494 (1988).

Japour et al., "Standardized Peripheral Blood Mononuclear Cell Culture Assay for Determination of Drug Susceptibilities of Clinical Human Immunodeficiency Virus Type 1 Isolates," *Antimicrob. Agents and Chemotherapy* 37(5):1095-1101 (1993).

Karup et al., "9-Acridinylpeptides and 9-Acridinyl-4-Nitrophenylsulfonylpeptides," *Int. J. Peptide Protein Res.* 32(5):331-343 (1988).

Kempf et al., "Pharmacokinetic Enhancement of Inhibitors of the Human Immunodeficiency Virus Protease by Coadministration with Ritonavir," *Antimicrob. Agents Chemother.* 41(3):654-660 (1997).

Kolc, "Amino Acids and Peptides," *Collect. Czech Chem. Commun.* 34(2):630-634 (1969).

Kottirsch et al., "Beta-Amino Acid Derivatives as Orally Active Non-Peptide fibrinogen Receptor Antagonists," *Bioorg. Med. Chem. Lett.* 7(6):727-732 (1997).

Lasky et al., "Delineation of a Region of the Human Immunodeficiency Virus Typ1 gp120 Glycoprotein Critical for Interaction with the CD4 Receptor," *Cell* 50(6):975-985 (1987).

Leclerc et al., "On the Selectivity of Acylation of Unprotected Diamino Acids," *Can. J. Chem.* 46(7):1047-1051 (1968).

Lescrinier et al., "α-Amino Acids Derived from Ornithine as Building Blocks for Peptide Synthesis," *J. Peptide Res.* 49(2):183-189 (1997).

Maeda et al., "Amino Acids and Peptides. V. Synthesis of Amino Acid Derivatives Containing a Sulfonamide Bond," *Chem. Pharm. Bull.* 33(5):2137-2141 (1985).

Matayoshi et al., Novel Fluorogenic Substrates for Assaying Retroviral Proteases by Resonance Energy Transfer, *Science* 247(4945):954-958 (1990).

Meek et al., "Inhibition of HIV-1 Protease in Infected T-Lymphocytes by Synthetic Peptide Analogues," *Nature* 343(6253):90-92 (1990).

Pauwels et al., "Rapid and Automated Tetrazolium-Based Colorimetric Assay for the Detection of Anti-HIV Compounds," *J. Virological Methods* 20(4):309-321 (1988).

Poduska et al., "Amino Acids and Peptides. LII. Intramolecular Aminolysis of Amide Bonds in Derivatives of α, λ- Diaminobutyric Acid, α, β-Diaminopropionic Acid and Irnithine," *Coll. Czech. Chem. Commun.* 30(7):2410-2433 (1965).

Sakai et al., "Integration is Essential for Efficient Gene Expression of Human Immunodeficiency Virus Type 1," *J. Virol.* 67(3):1169-1174 (1993).

Schon et al., "9-Fluorenylmethyl Pentaflourophenyl Carbonate as a Useful Reagent for the Preparation of N-9-Fluorenylmethyloxycarbonylamino Acids and Their Pentafluorophenyl Esters," *J. of Synthetic Org. Chem.* 4:303-305 (1986).

Sevigny et al., "Antiviral Activity and Cross-Resistance Profile of P-1946, A Novel Human Immunodeficiency Virus Type 1 Protease Inhibitor," *Antiviral Res.* 70(2):17-20 (2006).

Sohma et al., "Development of Water-Soluble Prodrugs of the HIV-1 Protease Inhibitor KNI-727: Importance of the Conversion Time for Higher Gastrointestinal Absorption of Prodrugs Based on Spontaneous Chemical Cleavage," *J. Med. Chem.* 46(19):4124-4135 (2003).

Solinas et al., "The Oxidative Deamination of I-Aminoethylcysteine Sulfoxide and Sulfone by Snake Venom I-Amino Acid Oxidase," *Physiol. Chem. Phys. Med. NMR.* 25(4):281-285 (1993).

(56) References Cited

OTHER PUBLICATIONS

Stranix et al., "Lysine Sulfonamides as Novel HIV-Protease Inhibitors: Nϵ-Acyl Aromatic α-Amino Acids," *Bioorg. Med. Chem. Lett.* 16(13):1359-3462 (2006).

Treluyer et al., "Oxidative Metabolism of Amprenavir in the Human Liver. Effect of the CYP3A Maturation," *Drug Metab. Disp.* 31(3):275-281 (2003).

Vierling et al., "Prodrugs of HIV Protease Inhibitors," *Current Pharmaceutical Design* 9:1755-1770 (2003).

International Preliminary Report on Patentability (PCT/IB2007/004453) issued Jan. 25, 2011.

International Search Report for PCT/CA2001/00296, dated Nov. 27, 2001, mailed Dec. 10, 2001.

International Search Report for PCT/CA2004/001440, dated Nov. 27, 2004, mailed Dec. 10, 2004.

Written Opinion for PCT/CA2004/001440, mailed Dec. 10, 2004.

European Search Report for EP 08021798.7 dated May 12, 2010.

European Examination Report for EP 08021798.7 dated May 25, 2010.

PROTEASE INHIBITORS

This application is a divisional of U.S. application Ser. No. 12/311,122, filed Mar. 19, 2009 and having a 371(c) date of Apr. 6, 2010, now U.S. Pat. No. 8,410,300, which was the U.S. National Stage of International Application No. PCT/IB2007/004453, filed Sep. 20, 2007, which claims the benefit of the filing date of U.S. Provisional Application No. 60/846,084, filed Sep. 21, 2006, the entire contents of which are herein incorporated by reference.

BACKGROUND OF THE INVENTION

Inhibitors of the HIV viral protease are presently considered the most effective drugs against HIV infection. Unfortunately, most current proteases inhibitors are relatively large hydrophobic molecules that possess rather low bioavailability. A high pill burden is therefore required to attain the therapeutic dose in a patient. This is a deterrent, which too often results in patient non-compliance and inadequate treatment results. This situation leads to sub-optimal therapeutic drug concentration that in turns leads to the development of HIV resistant strains. Consequently, there is an urgent need to improve the solubility and bioavailability of proteases inhibitors.

A unique class of amino acid based HIV protease inhibitors have been described in international application No. PCT/CA02/00190 published under No. WO02/064551 on Aug. 22, 2002 the entire content of which is incorporated herein by reference.

Aromatic derivatives have also been described in U.S. Pat. No. 6,632,816 to Stranix et al, the entire content of which is incorporated herein by reference. This patent includes, more particularly, N,-synthetic amino acid substituted L-lysine derivatives possessing potent aspartyl protease inhibitory properties. However, it would be advantageous to improve these derivatives by enhancing aqueous solubility and bioavailability in order to reduce the pill burden and to favour patient's compliance. Since it is challenging to generate active protease inhibitors, specifically toward wild-type and resistant strains, the formation of derivatives of original HIV protease inhibitors such as inhibitors described in U.S. Pat. No. 6,632,816 to Stranix et al, known to be active toward resistant strains represents a viable route with considerable advantages. More particularly, generation of compounds with enhanced aqueous solubility, bioavailability, time of duration and formulation properties along with other advantages is desirable in the development of an effective drug.

Compounds with improved solubility and bioavailability have been described in U.S. application Ser. No. 10/902,935 published under No. 2006-0025592A1 on Feb. 2, 2006 in the name of to Stranix et al. These compounds were found to be suitable for oral administration in aqueous solution.

SUMMARY OF THE INVENTION

The present invention provides new compounds which may be used to inhibit HIV protease.

More particularly, the present invention relates in a first aspect thereof to a compound of formula I

I

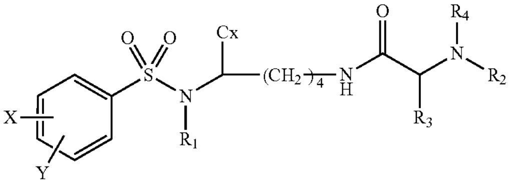

and pharmaceutically acceptable salt thereof, where Cx may be selected, for example, from the group consisting of $CH_2OH$, COOM', $CONR_5R_6$, $CH_2OR_7$ where $R_7$ may be selected from the group consisting of $(HO)_2P(O)$ and $(MO)_2P(O)$, where M' may be H or an alkali metal or alkaline earth metal, where M may be an alkali metal or alkaline earth metal and a group of formula $R_{7A}$—CO—, where $R_{7A}$ may be selected, for example, from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atom, —$CH_2OH$, $CH_3O_2C$—, $CH_3O_2CCH_2$—, Acetyl-$OCH_2CH_2$—, $HO_2CCH_2$—, 2-hydroxyphenyl, 3-hydroxyphenyl, 4-hydroxyphenyl, $(CH_3)_2NCH_2$—, $(CH_3)_2CHCH(NH_2)$—, $HOCH_2CH_2NH$—, $CH_3OCH_2O$—, $CH_3OCH_2CH_2O$—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

III

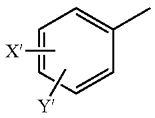

a picolyl group selected from the group consisting of

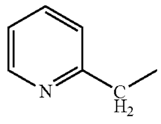

(2-picolyl)

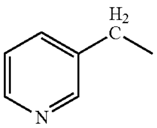

(3-picolyl)

and

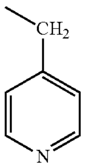

(4-picolyl)

a picolyloxy group selected from the group consisting of

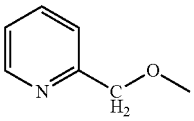

(2-picolyloxy)

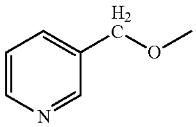

(3-picolyioxy)

and

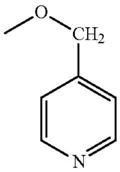

(4-picolyloxy)

a substituted pyridyl group selected from the group consisting of

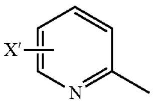 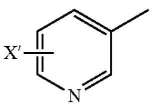 and 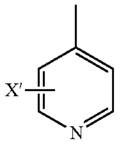

(substituted 2-pyridyl) (substituted 3-pyridyl) (substituted 4-pyridyl)

and a group of formula,

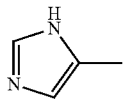

where X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, $—CF_3$, $—OCF_3$, —CN, $—NO_2$, $—NR_5R_6$, $—NHCOR_5$, $—OR_5$, $—SR_5$, $—COOR_5$, $—COR_5$, and $—CH_2OH$ or X and Y together define an ethyleneoxy group of formula $—OCH_2CH_2—$, or $—CH_2CH_2O—$, or an alkylenedioxy group selected from the group consisting of a methylenedioxy group of formula $—OCH_2O—$, and an ethylenedioxy group of formula $—OCH_2CH_2O—$, where $R_1$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, 2-pyridyl-$CH_2$—, 3-pyridyl-$CH_2$—, and 4-pyridyl-$CH_2$—, where $R_2$ may be selected, for example, from the group consisting of H, a straight alkyl group of 1 to 6 carbon atoms, a branched alkyl group of 3 to 6 carbon atoms, a cycloalkyl group of 3 to 6 carbon atoms, 2-pyridyl-$CH_2$—, 3-pyridyl-$CH_2$—, 4-pyridyl-$CH_2$—, a benzenesulfonyl group of formula

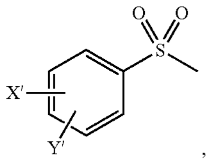, a thiophenesulfonyl group of formula

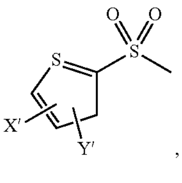, 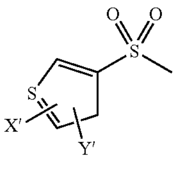

a group selected from the group of

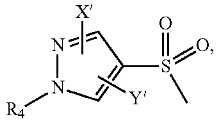 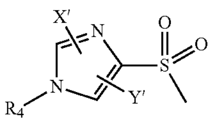

a group of formula

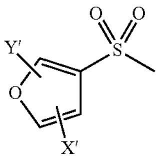

a group selected from the group of formula

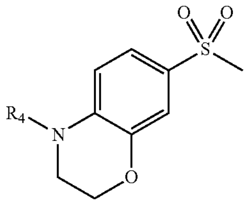 and 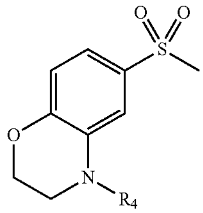

and a group of formula $R_{2A}$—CO—, where $R_{2A}$ may be selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, $—CH_2OH$, $—CF_3$, $—CH_2CF_3$, $—CH_2CH_2CF_3$, piperonyl, pyrrolidinyl, piperidinyl, 4-morpholinyl, $CH_3O_2C—$, $CH_3O_2CCH_2—$, Acetyl-$OCH_2CH_2—$, $HO_2CCH_2—$, 3-hydroxyphenyl, 4-hydroxyphenyl, 4-$CH_3OC_6H_4CH_2—$, $CH_3NH—$, $(CH_3)_2N—$, $(CH_3CH_2)_2N—$, $(CH_3CH_2CH_2)_2N—$, $HOCH_2CH_2NH—$, $CH_3OCH_2O—$, $CH_3OCH_2CH_2O—$, $C_6H_5CH_2O—$, 2-pyrrolyl, 2-pyridyl (unsubstituted or substituted), 3-pyridyl(unsubstituted or substituted), 4-pyridyl-(unsubstituted or substituted), 2-pyrazinyl (unsubstituted or substituted with H, alkyl of 1 to 4 carbon atoms), 2-quinolyl, 3-quinolyl, 4-quinolyl, 1-isoquinolyl, 3-isoquinolyl, 2-quinoxalinyl, a phenyl group of formula

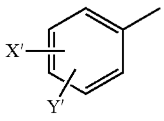

a picolyl group selected from the group consisting of

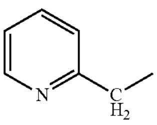 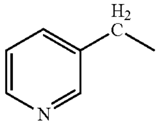 and 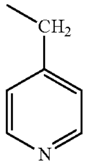

a picolylamine group selected from the group

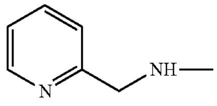 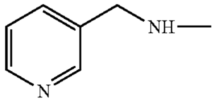 and 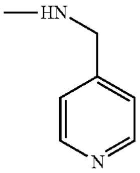

a picolyloxy group selected from the group consisting of

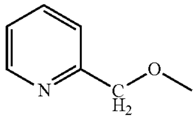 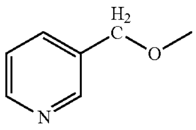 and 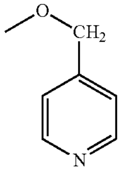

a substituted pyridyl group selected from the group consisting of

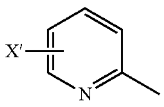 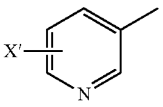 and 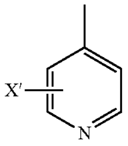

a group selected from the group consisting of

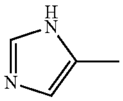 and 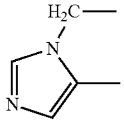 , where X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_5R_6$, —$NHCOR_5$, —$OR_5$, —$SR_5$, —$COOR_5$, —$COR_5$, —$OCF_3$, —CN and —$CH_2OH$, wherein $R_4$ may be selected, for example, from the group consisting of H, a straight alkyl group of 1 to 6 carbon atoms, a branched alkyl group of 3 to 6 carbon atoms, and a cycloalkyl group of 3 to 6 carbon atoms, where $R_5$ and $R_6$, the same or different, may be selected, for example, from the group consisting of H, a straight alkyl group of 1 to 6 carbon atoms, a branched alkyl group of 3 to 6 carbon atoms, and a cycloalkyl group of 3 to 6 carbon atoms, where $R_3$ may be selected, for example, from the group consisting of a cyclohexyl group of formula

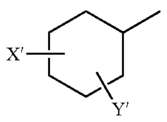

a phenyl group of formula

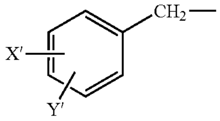

a diphenylmethyl group of formula IV

IV

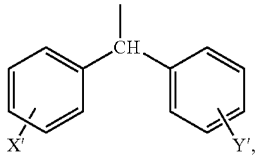

a naphthyl-1-$CH_2$— group of formula V

V

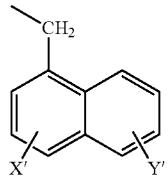

a naphthyl-2-$CH_2$— group of formula VI

VI

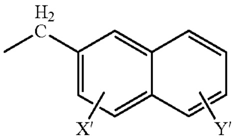

a biphenylmethyl group of formula VII

VII

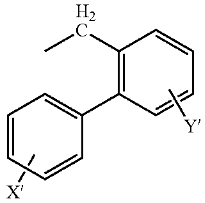

and an anthryl-9-$CH_2$— group of formula VIII

VIII

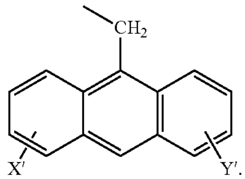

In accordance with the present invention, $R_2$ may be selected, for example, from the group consisting of 2-pyridyl-$CH_2$—, 3-pyridyl-$CH_2$—, 4-pyridyl-$CH_2$—, a benzenesulfonyl group of formula

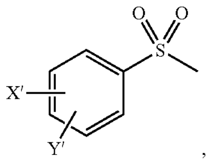
, a thiophenesulfonyl group of formula

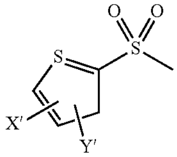
,
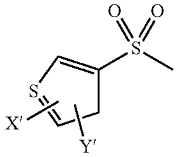

a group selected from the group of

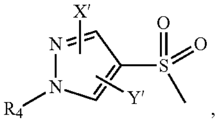
,
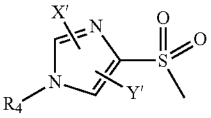

a group of formula

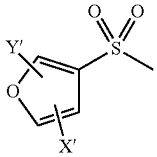

a group selected from the group of formula

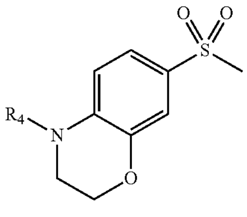
and
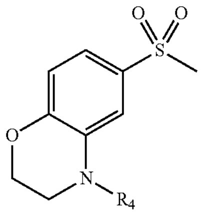

and a group of formula $R_{2A}$—CO—, where $R_{2A}$ may be selected from the group consisting of piperonyl, 2-pyrazinyl (unsubstituted or substituted with H, or an alkyl of 1 to 4 carbon atoms)

and a group selected from the group of

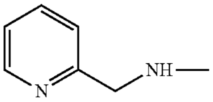
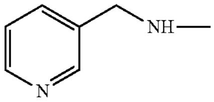
and
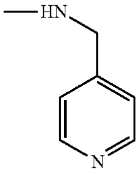

where X', Y', $R_5$, $R_6$ may be as defined herein.

In accordance with an exemplary embodiment of the present invention Cx may be COOH.

In accordance with an additional embodiment the present invention Cx may be $CONR_5R_6$.

In accordance with a further embodiment of the present invention, Cx may be $CH_2OH$.

In accordance with yet a further exemplary embodiment of the present invention, Cx may be $CH_2OR_7$.

In accordance with an exemplary embodiment of the present invention, $R_3$ may be a cyclohexyl group as described herein.

In accordance with an additional embodiment the present invention $R_3$ may be a diphenylmethyl group as described herein.

In accordance with a further embodiment of the present invention, R3 may be a naphthyl-$CH_2$ group as described herein.

In accordance with yet a further embodiment of the present invention, R3 may be a phenyl group as described herein.

In accordance with the present invention $R_3$ may be a phenyl group of formula

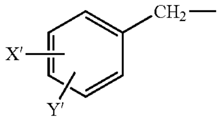

where X' or Y' may be as defined herein and where at least one of X' or Y' is, for example, a straight alkyl group of 1 to 6 carbon atoms, a branched alkyl group of 3 to 6 carbon atoms, a cycloalkyl group of 3 to 6 carbon atoms.

Also in accordance with the present invention $R_3$ may be a phenyl group of formula

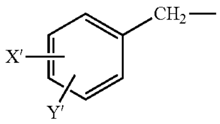

Cx may be $CH_2OR_7$ and where $R_7$ may be selected, for example, from the group consisting of $(HO)_2P(O)$ and $(MO)_2P(O)$, wherein M may be an alkali metal or alkaline earth metal and a group of formula.

Also in accordance with the present invention $R_3$ may be $(C_6H_5)_2CH$—, 1-naphtyl-$CH_2$— or 2-naphthyl-$CH_2$—.

In an additional aspect, the present invention relates to a compound of formula IA

IA

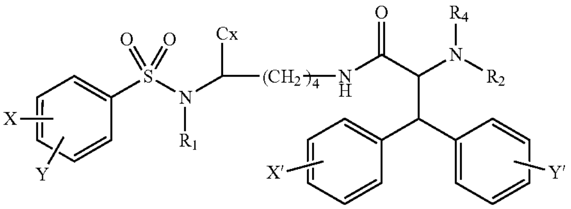

and pharmaceutically acceptable salt thereof, where Cx may be selected, for example from the group consisting of $CH_2OH$, COOM', $CONH_2$, $CONR_5R_6$, $CH_2OR_7$ where $R_7$ may be selected, for example, from the group consisting of $(HO)_2P(O)$ and $(MO)_2P(O)$, where M' may be H or an alkali metal or alkaline earth metal, wherein M may be an alkali metal or alkaline earth metal and a group of formula $R_{7A}$—CO—, where $R_{7A}$ may be, selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atom, —$CH_2OH$, $CH_3O_2C$—, $CH_3O_2CCH_2$—, Acetyl-$OCH_2CH_2$—, $HO_2CCH_2$—, 2-hydroxyphenyl, 3-hydroxyphenyl, 4-hydroxyphenyl, $(CH_3)_2NCH_2$—, $(CH_3)_2CHCH(NH_2)$—, $HOCH_2CH_2NH$—, $CH_3OCH_2O$—, $CH_3OCH_2CH_2O$—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

III

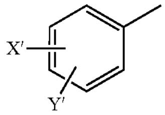

a picolyl group selected from the group consisting of

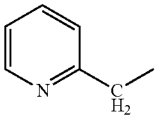
(2-picolyl)

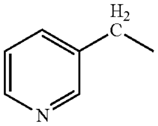
(3-picolyl)

and

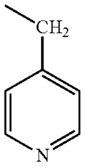
(4-picolyl)

a picolyloxy group selected from the group consisting of

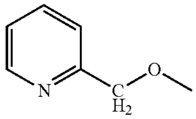
(2-picolyloxy)

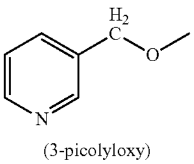
(3-picolyloxy)

and

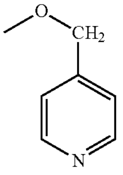
(4-picolyloxy)

a substituted pyridyl group selected from the group consisting of

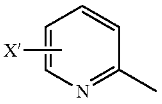
(substituted 2-pyridyl)

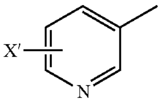
(substituted 3-pyridyl)

and

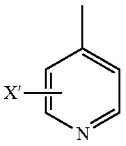
(substituted 4-pyridyl)

and a group of formula,

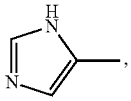
, where X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_5R_6$, —NH$COR_5$, —$OR_5$, —$SR_5$, —$COOR_5$, —$COR_5$, and —$CH_2OH$ or X and Y together define an ethyleneoxy group of formula —$OCH_2CH_2$— or —$CH_2CH_2O$—, or an alkylenedioxy group selected from the group consisting of a methylenedioxy group of formula —$OCH_2O$— and an ethylenedioxy group of formula —$OCH_2CH_2O$—, where $R_1$ may be selected from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, 2-pyridyl-$CH_2$—, 3-pyridyl-$CH_2$— and 4-pyridyl-$CH_2$—, where $R_2$ may be selected, for example, from the group consisting of H, a straight alkyl group of 1 to 6 carbon atoms, a branched alkyl group of 3 to 6 carbon atoms, a cycloalkyl group of 3 to 6 carbon atoms, 2-pyridyl-$CH_2$—, 3-pyridyl-$CH_2$—, 4-pyridyl-$CH_2$—, a benzenesulfonyl group of formula

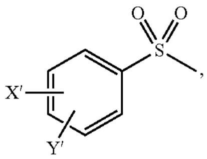
, a thiophenesulfonyl group of formula

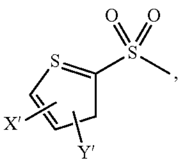
,

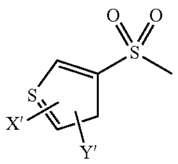

a group selected from the group of

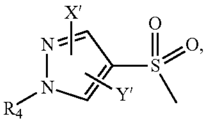

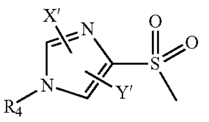

a group of formula

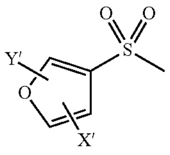

and a group of formula $R_{2A}$—CO—, $R_{2A}$ may be selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, piperonyl, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl- (unsubstituted or substituted), 3-pyridyl- (unsubstituted or substituted), 4-pyridyl-(unsubstituted or substituted), 2-pyrazinyl (unsubstituted or substituted with H, or an alkyl of 1 to 4 carbon atoms), 2-quinolyl, 3-quinolyl, 4-quinolyl, 1-isoquinolyl, 3-isoquinolyl, 2-quinoxalinyl, a phenyl group of formula

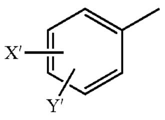

a picolyl group selected from the group consisting of

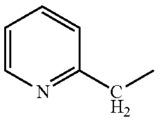

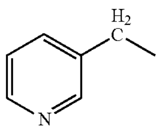

and

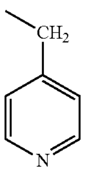

a picolylamine group selected from the group

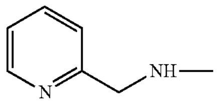

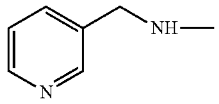

and

-continued

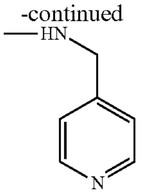

a picolyloxy group selected from the group consisting of

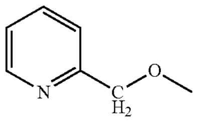

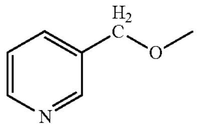

and

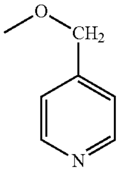

a substituted pyridyl group selected from the group consisting of

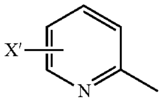

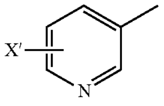

and

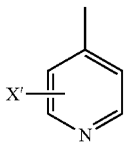

a group selected from the group consisting of

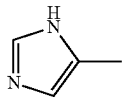

and,

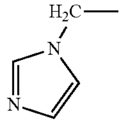

, where X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_5R_6$, —$NHCOR_5$, —$OR_5$, —$SR_5$, —$COOR_5$, —$COR_5$, —CN, —$OCF_3$ and —$CH_2OH$, where $R_4$ may be selected from the group consisting of H, a straight alkyl group of 1 to 6 carbon atoms, a branched alkyl group of 3 to 6 carbon atoms, and a cycloalkyl group of 3 to 6 carbon atoms, where $R_5$ and $R_6$, the same or different, may be selected from the group consisting of H, a straight alkyl group of 1 to 6 carbon atoms, a branched alkyl group of 3 to 6 carbon atoms, and a cycloalkyl group of 3 to 6 carbon atoms, In accordance with an embodiment of the invention, Cx may be selected from the group consisting of COOH, and $CONR_5R_6$.

In accordance with the present invention, $R_2$ may be selected from the group consisting of 2-pyridyl-$CH_2$—, 3-pyridyl-$CH_2$—, 4-pyridyl-$CH_2$—, a benzenesulfonyl group of formula

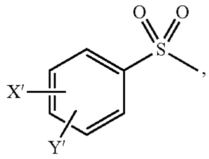
, a thiophenesulfonyl group of formula

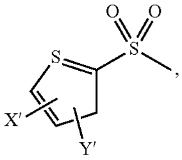
,
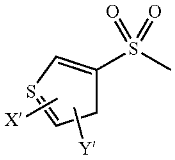

a group selected from the group of

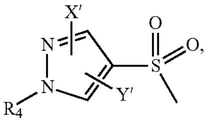
,
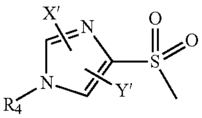

a group of formula

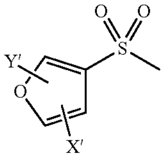

a group selected from the group of formula

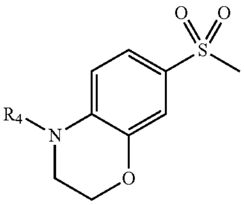
and
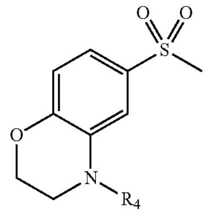

and a group of formula $R_{2A}$—CO—, where $R_{2A}$ may be selected from the group consisting of piperonyl, $NR_5R_6(CH_2)_m$—O—, 2-pyrazinyl (unsubstituted or substituted with H, or an alkyl of 1 to 4 carbon atoms), and a group selected from the group

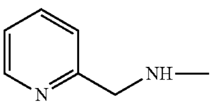
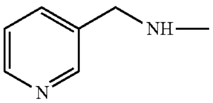
and

-continued

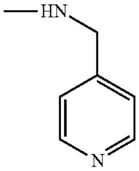

In a particular embodiment of the present invention, $R_2$ may be selected, for example, from the group consisting of a benzenesulfonyl group of formula

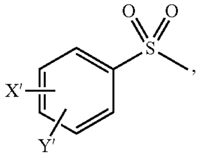
, a thiophenesulfonyl group of formula

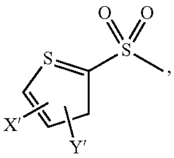
,
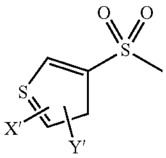

a group selected from the group of

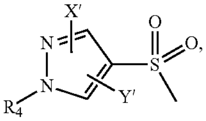
,
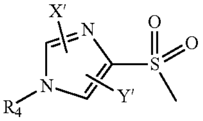

a group of formula

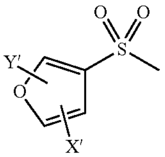

and a group selected from the group of formula

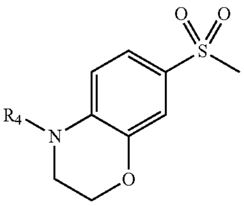
and
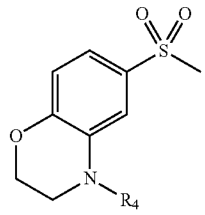

In a further aspect the present invention relates to a compound of formula IB

IB

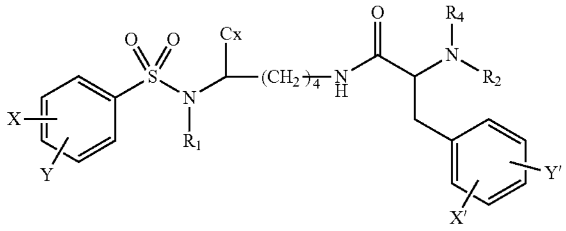

and pharmaceutically acceptable salt thereof, where Cx may be selected, for example, from the group consisting of $CH_2OH$, COOM', $CONH_2$, $CONR_5R_6$, $CH_2OR_7$ where $R_7$ may be selected from the group consisting of $(HO)_2P(O)$ and $(MO)_2P(O)$, where M' may be H or an alkali metal or alkaline earth metal, where M may be an alkali metal or alkaline earth metal and a group of formula $R_{7A}$—CO—, where $R_{7A}$ may be selected, for example, from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atom, —$CH_2OH$, $CH_3O_2C$—, $CH_3O_2CCH_2$—, Acetyl-$OCH_2CH_2$—, $HO_2CCH_2$—, 2-hydroxyphenyl, 3-hydroxyphenyl, 4-hydroxyphenyl, $(CH_3)_2NCH_2$—, $(CH_3)_2CHCH(NH_2)$—, $HOCH_2CH_2NH$—, $CH_3OCH_2O$—, $CH_3OCH_2CH_2O$—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

III

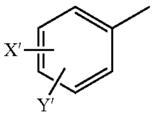

a picolyl group selected from the group consisting of

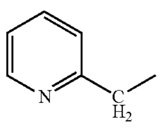

(2-picolyl)

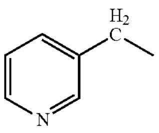

(3-picolyl)

and

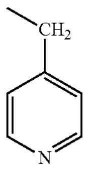

(4-picolyl)

a picolyloxy group selected from the group consisting of

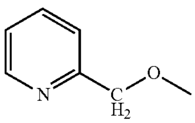

(2-picolyloxy)

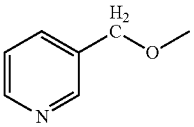

(3-picolyloxy)

and

-continued

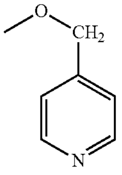

(4-picolyloxy)

a substituted pyridyl group selected from the group consisting of

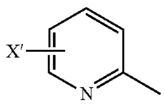

(substituted 2-pyridyl)

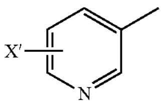

(substituted 3-pyridyl)

and

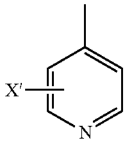

(substituted 4-pyridyl)

and a group of formula,

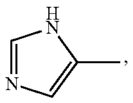

, where X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_5R_6$, —NH-$COR_5$, —$OR_5$, —$SR_5$, —$COOR_5$, —$COR_5$, and —$CH_2OH$ or X and Y together define an ethylenoxy group of formula —$CH_2CH_2O$— or —$CH_2CH_2O$— or an alkylenedioxy group selected from the group consisting of a methylenedioxy group of formula —$OCH_2O$— and an ethylenedioxy group of formula —$OCH_2CH_2O$—, where $R_1$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, 2-pyridyl-$CH_2$—, 3-pyridyl-$CH_2$—, and 4-pyridyl-$CH_2$—, where $R_2$ may be selected, for example, from the group consisting of piperonyl-CO—, 2-pyridyl-CO—, 3-pyridyl-CO—, 4-pyridyl-CO—, 2-pyrazinyl-CO— (unsubstituted or substituted with H, or an alkyl of 1 to 4 carbon atoms), a carboxyphenyl group of formula

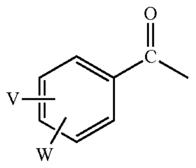

and a pyridyl-CO— group selected from the group consisting of

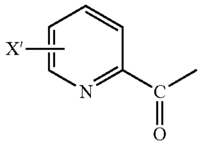

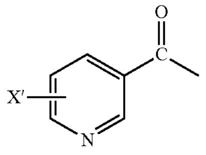

and

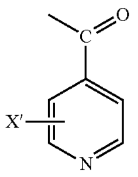

where at least one of V and W may be a straight alkyl group of 1 to 6 carbon atoms, a branched alkyl group of 3 to 6 carbon atoms, a cycloalkyl group of 3 to 6 carbon atoms and the other of V and W being, H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_5R_6$, —$NHCOR_5$, —$OR_5$, —$SR_5$, —$COOR_5$, —$COR_5$, and —$CH_2OH$, where X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_5R_6$, —$NHCOR_5$, —$OR_5$, —$SR_5$, —$COOR_5$, —$COR_5$, and —$CH_2OH$, where $R_4$ may be selected from the group consisting of H, a straight alkyl group of 1 to 6 carbon atoms, a branched alkyl group of 3 to 6 carbon atoms, and a cycloalkyl group of 3 to 6 carbon atoms, where $R_5$ and $R_6$, the same or different, may be selected from the group consisting of H, a straight alkyl group of 1 to 6 carbon atoms, a branched alkyl group of 3 to 6 carbon atoms, and a cycloalkyl group of 3 to 6 carbon atoms.

In yet a further aspect the present invention relates to a compound of formula Ib Ib

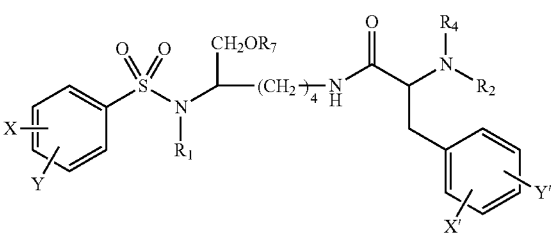

and pharmaceutically acceptable salt thereof, where $R_7$ may be selected, for example, from the group consisting of $(HO)_2P(O)$ and $(MO)_2P(O)$, where M may be an alkali metal or alkaline earth metal and a group of formula $R_{7A}$—CO—, $R_{7A}$ may be selected from the group consisting of an alkyloxy group of 1 to 6 carbon atom, —$CH_2OH$, $CH_3O_2C$—, $CH_3O_2CCH_2$—, Acetyl-$OCH_2CH_2$—, $HO_2CCH_2$—, 2-hydroxyphenyl, 3-hydroxyphenyl, 4-hydroxyphenyl, $(CH_3)_2NCH_2$—, $(CH_3)_2CHCH(NH_2)$—, $HOCH_2CH_2NH$—, $CH_3OCH_2O$—, $CH_3OCH_2CH_2O$—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

III

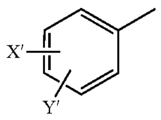

a picolyl group selected from the group consisting of

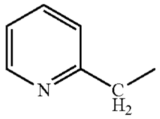

(2-picolyl)

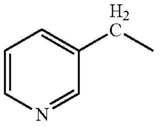

(3-picolyl)

and

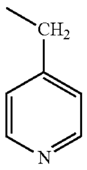

(4-picolyl)

a picolyloxy group selected from the group consisting of

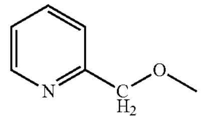

(2-picolyloxy)

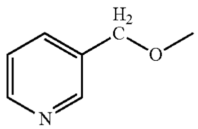

(3-picolyloxy)

and

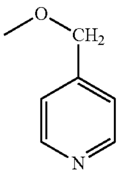

(4-picolyloxy)

a substituted pyridyl group selected from the group consisting of

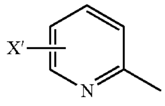

(substituted 2-pyridyl)

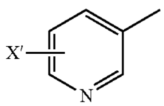

(substituted 3-pyridyl)

and

-continued

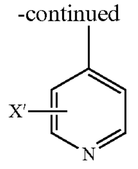

(substituted 4-pyridyl)

and a group of formula,

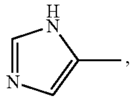

, where X and Y, the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_5R_6$, —$NHCOR_5$, —$OR_5$, —$SR_5$, —$COOR_5$, —$COR_5$, and —$CH_2OH$ or X and Y together define an ethylenoxy group of formula —$CH_2CH_2O$— or —$OCH_2CH_2$— or an alkylenedioxy group selected from the group consisting of a methylene-dioxy group of formula —$OCH_2O$— and an ethylenedioxy group of formula —$OCH_2CH_2O$—, where $R_1$ may be selected, for example, from the group consisting of a straight alkyl group of 1 to 6 carbon atoms, a branched alkyl group of 3 to 6 carbon atoms, a cycloalkyla-lkyl group having 3 to 6 carbon atoms in the cycloalkyl part thereof and 1 to 3 carbon atoms in the alkyl part thereof, 2-pyridyl-$CH_2$—, 3-pyridyl-$CH_2$— and 4-pyridyl-$CH_2$—, where $R_2$ may be selected, for example, from the group consisting of H, a straight alkyl group of 1 to 6 carbon atoms, a branched alkyl group of 3 to 6 carbon atoms, a cycloalkyl group of 3 to 6 carbon atoms, 2-pyridyl-$CH_2$—, 3-pyridyl-$CH_1$—, 4-pyridyl-$CH_2$—, a benzenesulfonyl group of formula

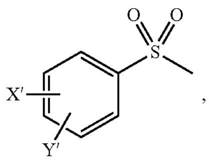

, a thiophenesulfonyl group of formula

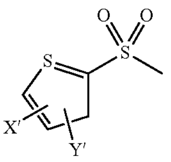

,

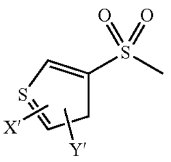

a group selected from the group of

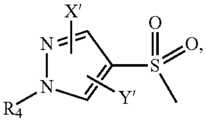

,

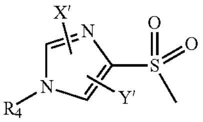

a group of formula

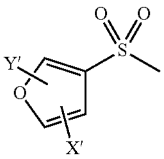

, a group selected from the group of formula

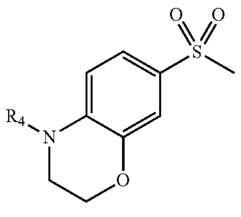

and

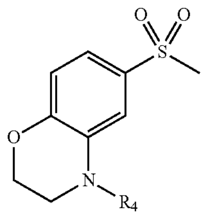

and a group of formula $R_{2A}$—CO— where $R_{2A}$ may be selected, for example, from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, piperonyl, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hy-droxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl, 3-pyridyl, 4-pyridyl-, 2-pyrazinyl (unsubstituted or substituted with H or an alkyl of 1 to 4 carbon atoms), 2-quinolyl, 3-quinolyl, 4-quinolyl, 1-isoquinolyl, 3-isoquinolyl, 2-quinoxalinyl, a phenyl group of formula

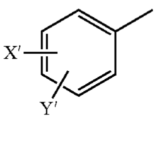

a picolyl group selected from the group consisting of

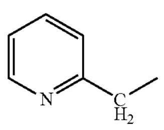

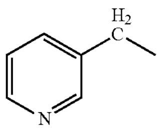

and

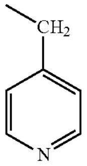

a picolyamine group selected from the group

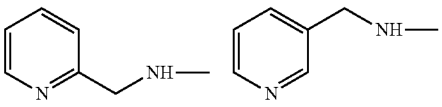

and

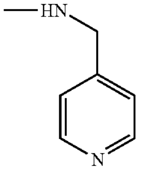

a picolyloxy group selected from the group consisting of

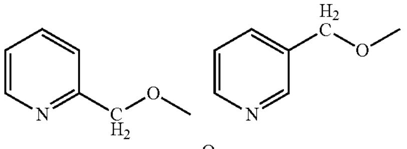

and

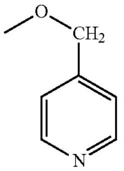

a substituted pyridyl group selected from the group consisting of

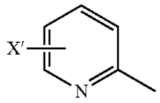

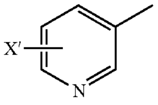

and

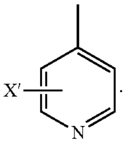

a group selected from the group consisting of

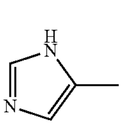

and

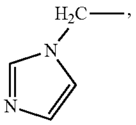

wherein X' and Y', the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_5R_6$, —$NHCOR_5$, —$OR_5$, —$SR_5$, —$COOR_5$, —$COR_5$, —CN, —$OCF_3$, and —$CH_2OH$, wherein $R_4$ may be selected, for example, from the group consisting of H, a straight alkyl group of 1 to 6 carbon atoms, a branched alkyl group of 3 to 6 carbon atoms, and a cycloalkyl group of 3 to 6 carbon atoms, and wherein $R_5$ and $R_6$, the same or different, may be selected from the group consisting of H, a straight alkyl group of 1 to 6 carbon atoms, a branched alkyl group of 3 to 6 carbon atoms, and a cycloalkyl group of 3 to 6 carbon atoms.

In an additional aspect, the present invention relates to a compound of formula II

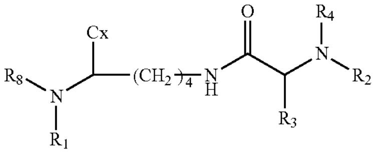

II and pharmaceutically acceptable salts thereof, where Cx may be selected from the group consisting of $CH_2OH$, COOM', $CONH_2$, $CONR_5R_6$, $CH_2OR_7$ where $R_7$ may be selected from the group consisting of $(HO)_2P(O)$ and $(MO)_2P(O)$, where M' may be H or an alkali metal or alkaline earth metal, where M may be an alkali metal or alkaline earth metal and a group of formula $R_{7A}$—CO—, where $R_{7A}$ may be selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atom, —$CH_2OH$, $CH_3O_2C$—, $CH_3O_2CCH_2$—, Acetyl-$OCH_2CH_2$—, $HO_2CCH_2$—, 2-hydroxyphenyl, 3-hydroxyphenyl, 4-hydroxyphenyl, $(CH_3)_2NCH_2$—, $(CH_3)_2CHCH(NH_2)$—, $HOCH_2CH_2NH$—, $CH_3OCH_2O$—, $CH_3OCH_2CH_2O$—, 2-pyrrolyl, 2-pyridyl, 3-pyridyl, 4-pyridyl, 1-methyl-1,4-dihydro-3-pyridyl, 2-pyrazinyl, 2-quinolyl, 3-quinolyl, 4-quinolyl, 1-isoquinolyl, 3-isoquinolyl, 2-quinoxalinyl, a phenyl group of formula

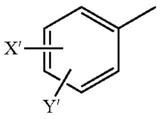

III a picolyl group selected from the group consisting of

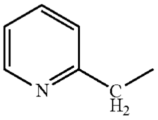

(2-picolyl)

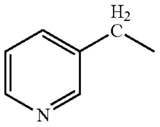

(3-picolyl)

and

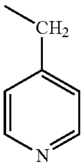

(4-picolyl)

a picolyloxy group selected from the group consisting of

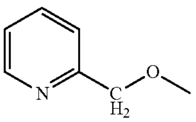

(2-picolyloxy)

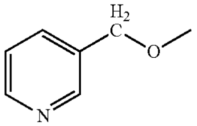

(3-picolyloxy)

and

-continued

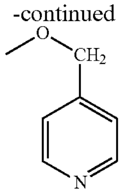

(4-picolyloxy)

a substituted pyridyl group selected from the group consisting of

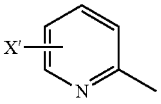

(substituted 2-pyridyl)

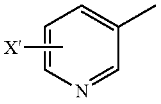

(substituted 3-pyridyl)

and

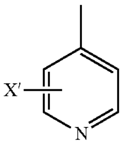

(substituted 4-pyridyl)

a group of formula,

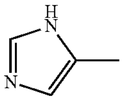

where X and Y, the same or different, may be selected, for example, from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$OCF_3$, —CN, —$NO_2$, —$NR_5R_6$, —NH-$COR_5$, —$OR_5$, —$SR_5$, —$COOR_5$, —$COR_5$, and —$CH_2OH$ or X and Y together define an ethylenoxy group of formula —$CH_2CH_2O$— or —$OCH_2CH_2$— or an alkylenedioxy group selected from the group consisting of a methylenedioxy group of formula —$OCH_2O$— and an ethylenedioxy group of formula —$OCH_2CH_2O$—, wherein $R_1$ may be selected, for example, from the group consisting of a straight alkyl group of 1 to 6 carbon atoms, a branched alkyl group of 3 to 6 carbon atoms, a cycloalkylalkyl group having 3 to 6 carbon atoms in the cycloalkyl part thereof and 1 to 3 carbon atoms in the alkyl part thereof, 2-pyridyl-$CH_2$—, 3-pyridyl-$CH_2$—, 4-pyridyl-$CH_2$—, wherein $R_2$ may be selected, for example, from the group consisting of H, a straight alkyl group of 1 to 6 carbon atoms, a branched alkyl group of 3 to 6 carbon atoms, a cycloalkyl group of 3 to 6 carbon atoms, 2-pyridyl-$CH_2$—, 3-pyridyl-$CH_2$—, 4-pyridyl-$CH_2$—, a benzenesulfonyl group of formula

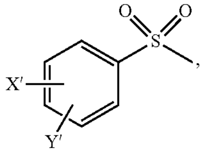

a thiophenesulfonyl group of formula

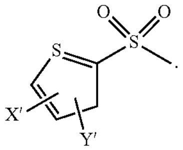

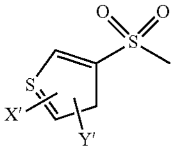

a group selected from the group of

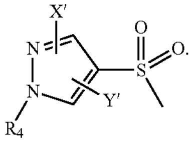

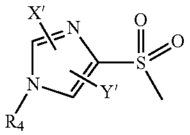

a group of formula

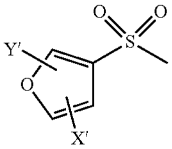

a group selected from the group of formula

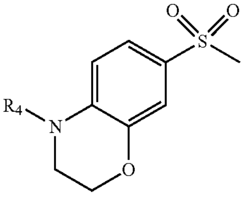

and

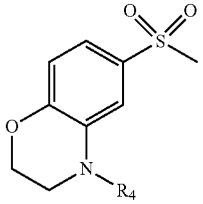

and a group of formula $R_{2A}$—CO—, where $R_{2A}$ may be selected from the group consisting of a straight or branched alkyl group of 1 to 6 carbon atoms, a cycloalkyl group having 3 to 6 carbon atoms, a cycloalkylalkyl group having 3 to 6 carbon atoms in the cycloalkyl part thereof and 1 to 3 carbon atoms in the alkyl part thereof, an alkyloxy group of 1 to 6 carbon atoms, tetrahydro-3-furanyloxy, —$CH_2OH$, —$CF_3$, —$CH_2CF_3$, —$CH_2CH_2CF_3$, piperonyl, pyrrolidinyl, piperidinyl, 4-morpholinyl, $CH_3O_2C$—, $CH_3O_2CCH_2$—, Acetyl-$OCH_2CH_2$—, $HO_2CCH_2$—, 3-hydroxyphenyl, 4-hydroxyphenyl, 4-$CH_3OC_6H_4CH_2$—, $CH_3NH$—, $(CH_3)_2N$—, $(CH_3CH_2)_2N$—, $(CH_3CH_2CH_2)_2N$—, $HOCH_2CH_2NH$—, $CH_3OCH_2O$—, $CH_3OCH_2CH_2O$—, $C_6H_5CH_2O$—, 2-pyrrolyl, 2-pyridyl (unsubstituted or substituted), 3-pyridyl (unsubstituted or substituted), 4-pyridyl- (unsubstituted or substituted), 2-pyrazinyl (unsubstituted or substituted with H, or an alkyl of 1 to 4 carbon atoms), 2-quinolyl, 3-quinolyl, 4-quinolyl, 1-isoquinolyl, 3-isoquinolyl, 2-quinoxalinyl, a phenyl group of formula

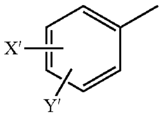

a picolyl group selected from the group consisting of

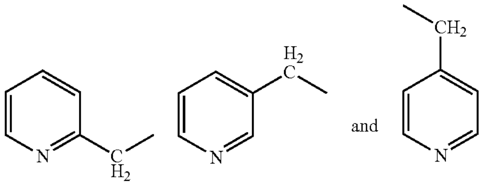

and a picolylamine group selected from the group

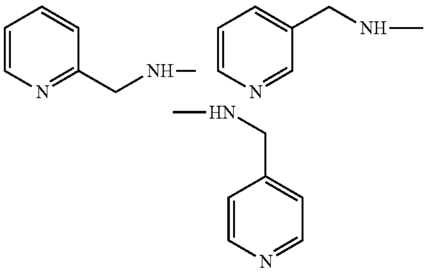

and a picolyloxy group selected from the group consisting of

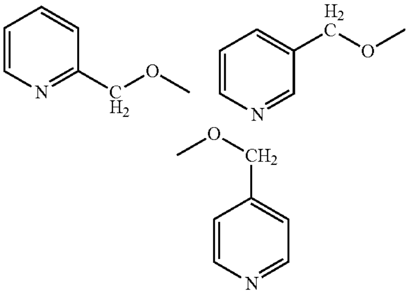

and a substituted pyridyl group selected from the group consisting of

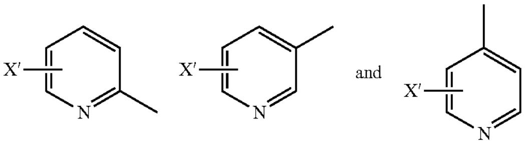

and a group selected from the group consisting of

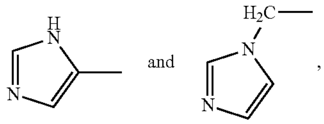

and , where X' and Y', the same or different, may be selected from the group consisting of H, a straight alkyl group of 1 to 6 carbon atoms, a branched alkyl group of 3 to 6 carbon atoms, a cycloalkyl group of 3 to 6 carbon atoms, F, Cl, Br, I, —$CF_3$, —$NO_2$, —$NR_5R_6$, —$NHCOR_5$, —$OR_5$, —$SR_5$, —$COOR_5$, —$COR_5$, —CN, —$OCF_3$ and —$CH_2OH$, where $R_4$ may be selected from the group consisting of H, a straight alkyl group of 1 to 6 carbon atoms, a branched alkyl group of 3 to 6 carbon atoms, and a cycloalkyl group of 3 to 6 carbon atoms, where $R_5$ and $R_6$, the same or different, may be selected from the group consisting of H, a straight alkyl group of 1 to 6 carbon atoms, a branched alkyl group of 3 to 6 carbon atoms, and a cycloalkyl group of 3 to 6 carbon atoms, where $R_8$ may be selected from the group consisting of a group selected from the group of

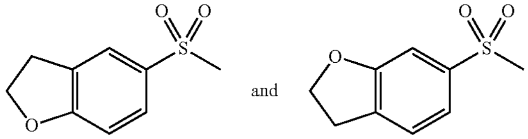

and a group selected from the group of

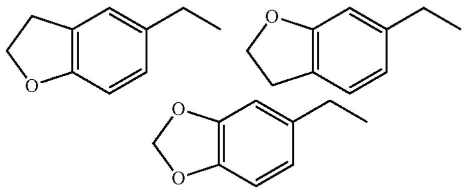

and a group of formula

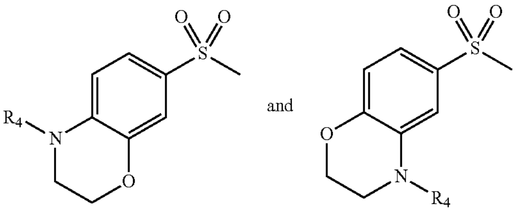

and and a group of formula

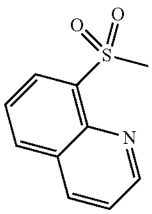

where $R_3$ may be selected from the group consisting of a phenyl group of formula

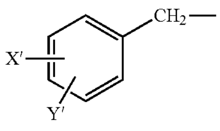

a diphenylmethyl group of formula IV

IV

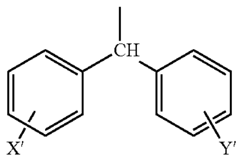

a naphthyl-1-$CH_2$— group of formula V

V

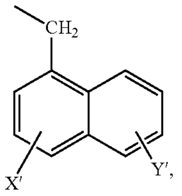

a naphthyl-2-$CH_2$— group of formula VI

VI

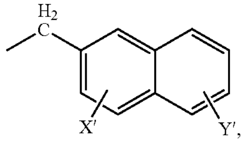

a biphenylmethyl group of formula VII

VII

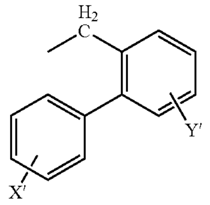

and an anthryl-9-$CH_2$— group of formula VIII

VIII

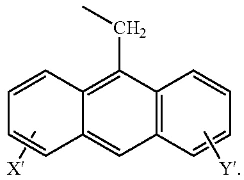

The present invention further relates to the use of at least one compound described herein for making a pharmaceutical composition, medicament or drug. The compound described herein may be used in the making of a drug for the treatment and/or prevention of HIV infection and/or for the prevention of the apparition of acquired immunodeficiency syndrome (AIDS), and/or for reducing HIV replication and/or its cytopathic effects and/or inhibiting the HIV protease enzyme (e.g., for reducing the activity of an HIV protease) etc.

The present invention further relates to the use of the at least one compound described herein for treating and/or preventing HIV infection and/or AIDS for reducing HIV replication and/or its cytopathic effects and/or inhibiting the HIV protease enzyme or else in an individual in need thereof.

The invention also relates to a method of treating and/or preventing HIV infection and/or AIDS (e.g., for delaying the apparition of AIDS), for reducing HIV replication and/or its cytopathic effects and/or for inhibiting the HIV protease enzyme or else in an individual in need thereof. In accordance with the present invention, the method may comprise administering a compound described herein (or a pharmaceutical composition, drug etc.) to (in) an individual in need thereof.

The present invention more particularly relates to a method of reducing the replication of HIV, the method may comprise providing a cell with a compound described herein (or a pharmaceutical composition, drug etc.) or administering such compound to (in) an individual in need thereof.

The present invention also relates to a process or method for preparing the compounds described herein and the use of intermediate compounds for such purpose.

The compounds of this invention may include pharmaceutically acceptable derivatives of the compounds as described herein. A "pharmaceutically acceptable derivative" means any pharmaceutically acceptable salt (e.g., Na, K, Cs, etc), acetals (i.e., dimethylacetal, diethylacetal, etc), oxime, ammonium or ester (as for example, but not limited to methyl, ethyl, propyl, isopropyl esters, etc) of a compound of this invention.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethyleneglycol, sodium carboxymethylcellulose, polyacrylates, waxes, polyethylene-polyoxypropylene-block polymers, polyethylene glycol and wool fat.

The pharmaceutical compositions of this invention may be administered orally, parenterally by inhalation spray, topically, rectally, nasally, buccally, vaginally or via an implanted reservoir. We prefer oral administration or administration by injection. The pharmaceutical compositions of this invention may contain any conventional non-toxic pharmaceutically acceptable carriers, adjuvants or vehicles. The term "parenteral" as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are amino acid, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv. or a similar alcohol.

The pharmaceutical compositions of this invention may be orally administered in any orally acceptable dosage form including, but not limited to, capsules, tablets, and aqueous suspension and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene or polyoxypropylene compound, emulsifying wax and water. Alternatively, the pharmaceutical compositions can be formulated with a suitable lotion or cream containing the active compound suspended or dissolved in a carrier. Suitable carriers include, but are not limited to, mineral oil, sorbitan monostearate, polysorbate 60, cetyl esters wax cetearyl alcohol, 2-octyldodecanol, benzyl alcohol and water. The pharmaceutical compositions of this invention may also be topically applied to the lower intestinal tract by rectal suppository formulation or in a suitable neat formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline employing benzyl alcohol or other suitable preservatives, absorption promoters to enhance bioavailability, fluorocarbons, and/or other solubilizing or dispersing agents known in the art.

Dosage levels of between about 0.01 and about 25 mg/kg body weight per day, preferably between about 0.5 and about 25 mg/kg body weight per day of the active ingredient compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the patient treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis, upon any recurrence of disease symptoms.

As the skilled artisan will appreciate, lower or higher doses than those recited above may be required. Specific dosage and treatment regimen for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

It is to be understood herein, that if a "range" or "group of substances" is mentioned with respect to a particular characteristic (e.g., temperature, concentration, time and the like) of the present invention, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or subgroups therein. Thus, for example, with respect to the number of carbon atoms, the mention of the range of 1 to 6 carbon atoms is to be understood herein as incorporating each and every individual number of carbon atoms as well as sub-ranges such as, for example, 1 carbon atoms, 3 carbon atoms, 4 to 6 carbon atoms, etc.

It is in particular to be understood herein that the compound formulae each include each and every individual compound described thereby as well as each and every possible class or sub-group or sub-class of compounds whether such class or sub-class is defined as positively including particular compounds, as excluding particular compounds or a combination thereof; for example an exclusionary definition may read as follows: "provided that when one of A and B is —COOH and the other is H, —COOH may not occupy the 4' position".

The compounds of the present invention may be prepared using conventional techniques from readily available starting materials. The detailed descriptions of these approaches are presented herein.

Schemes illustrate a generic example for the preparation of the compounds described herein.

Scheme 1
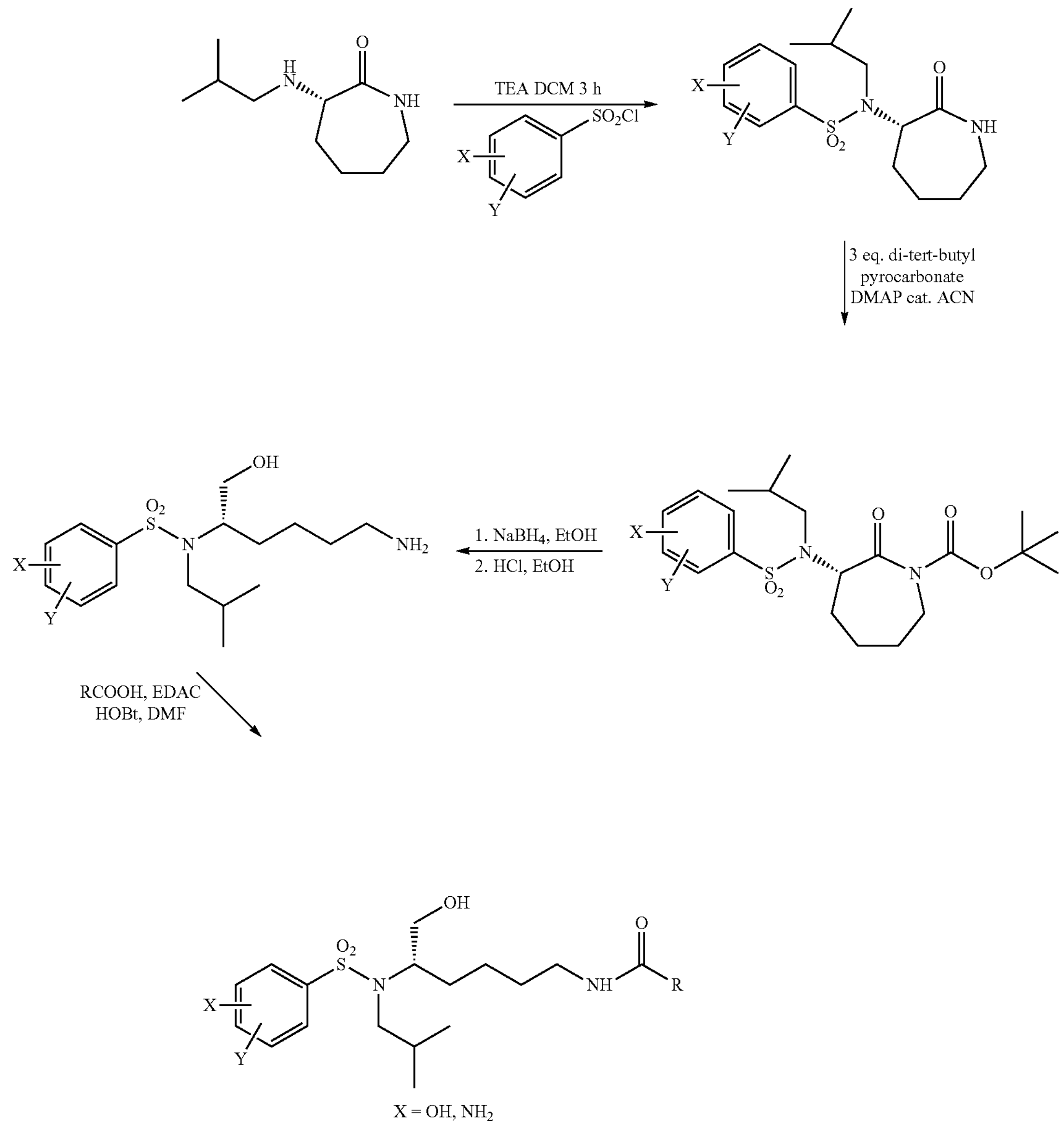
Scheme 2
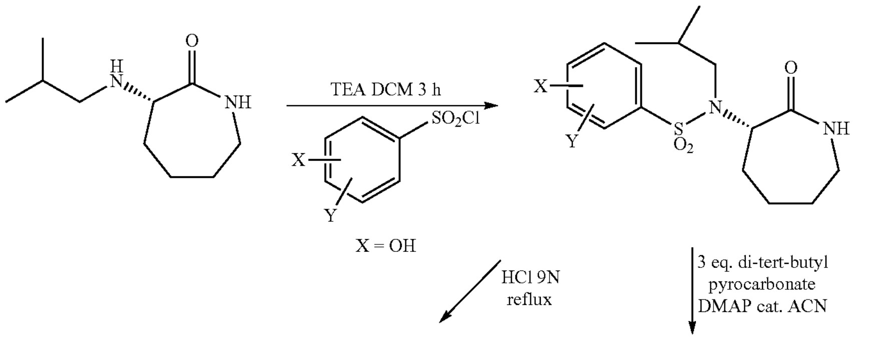

-continued
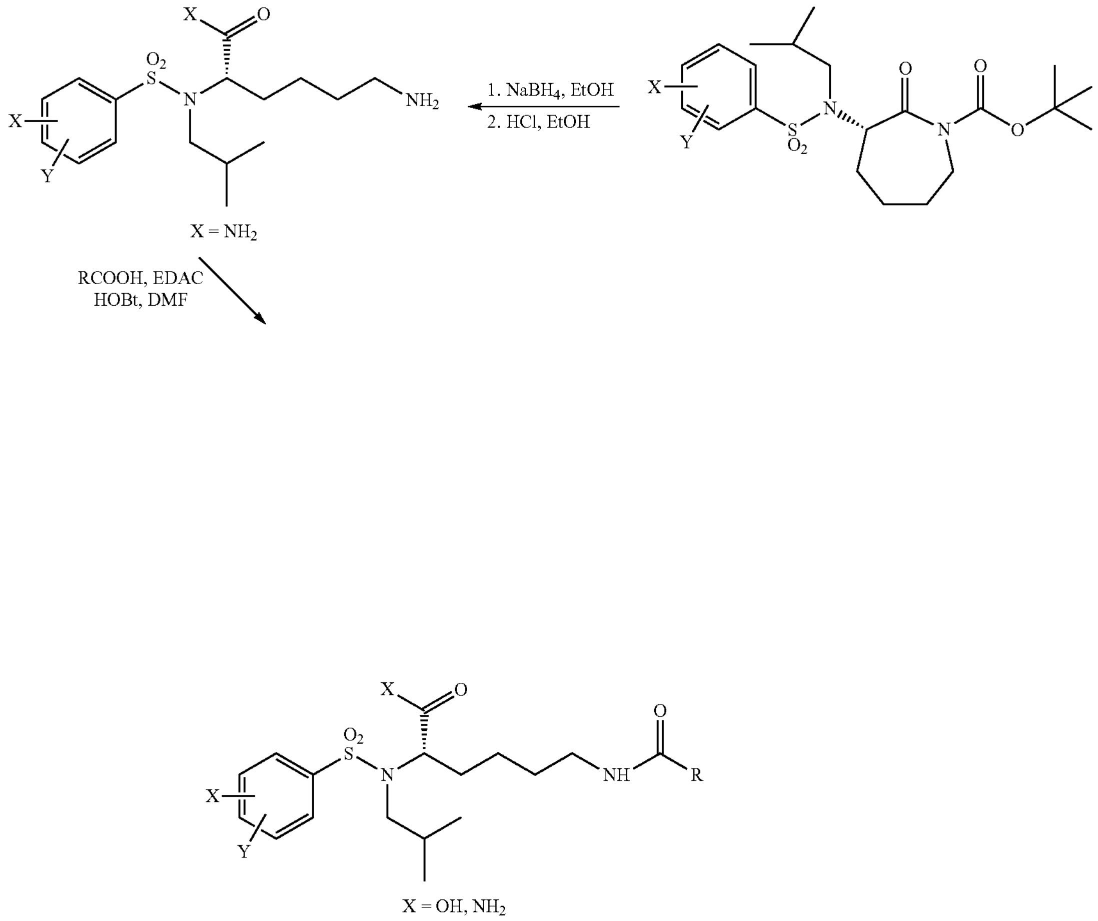
Scheme 3
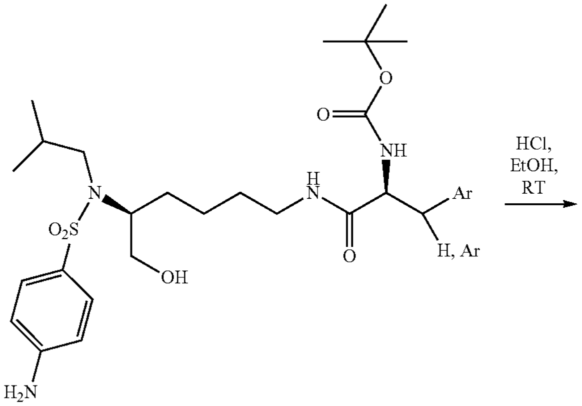
XVII
-continued
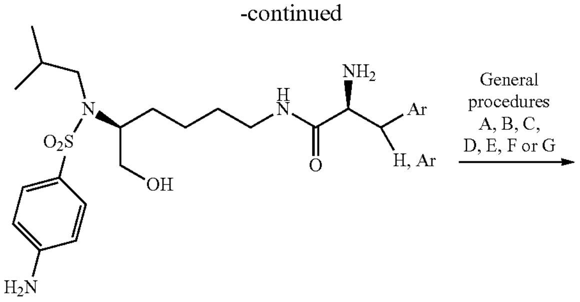
XVIII
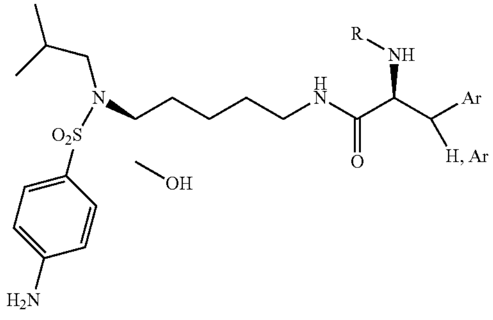
XIX Scheme 4

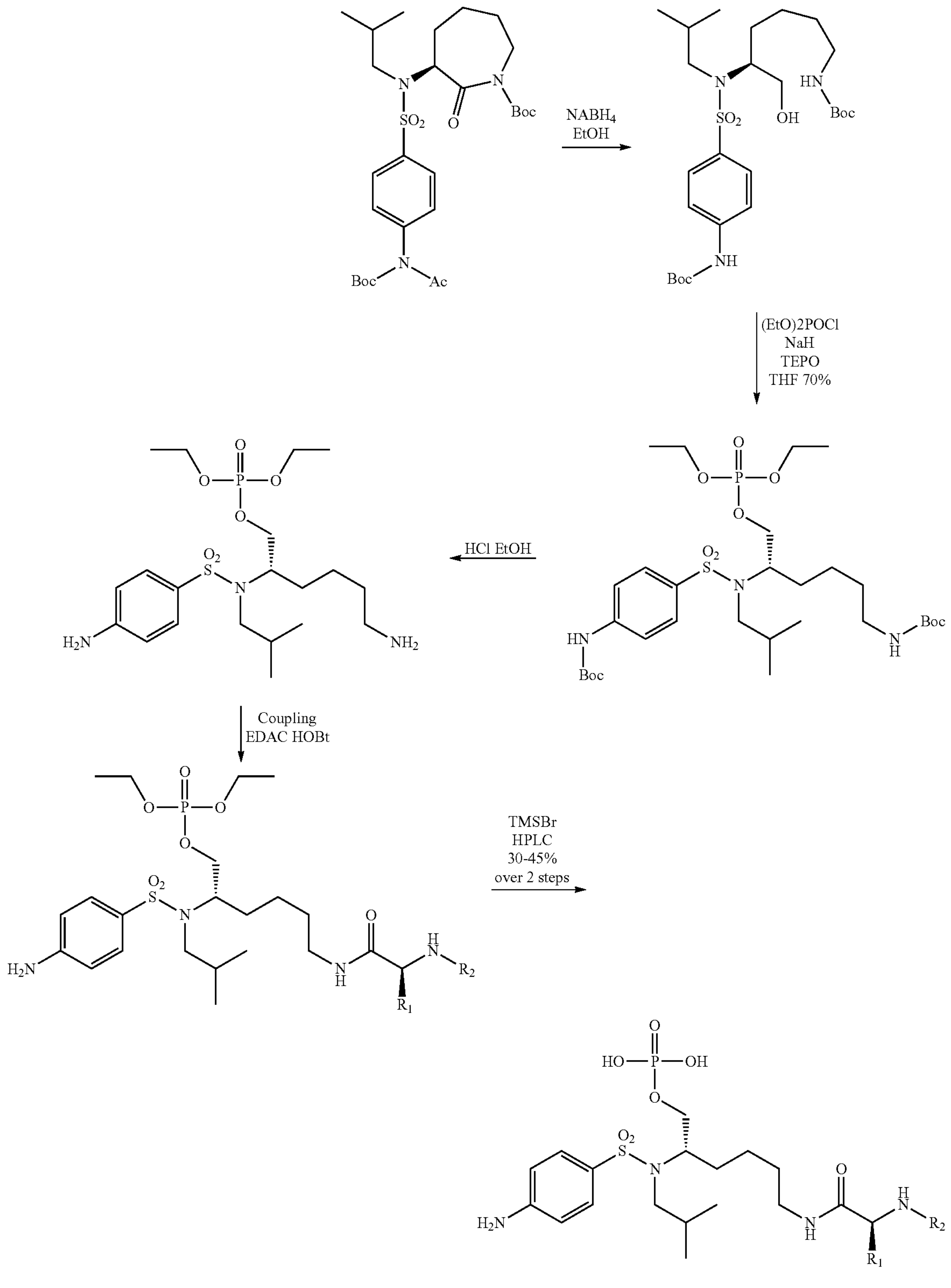

As it may be appreciated by the person skilled in the art, the above synthetic schemes are not intended to be a comprehensive list of all means by which the compound described and claimed in this application may be synthesized but only represent exemplification of synthesis methods among others. Further methods will be evident to those of ordinary skill in the art.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

In the description herein, the following abbreviations are used:

| Abbreviation | Meaning |
|---|---|
| Ac | Acetyl |
| AcOH | Acetic acid |
| APCI | Atmospheric pressure chemical ionization |
| AIDS | Acquired Immunodeficiency Syndrome |
| AZT | 3-Azido-3-deoxythymine (Zidovudine) |
| Boc | Benzyloxycarbonyl |
| t-Butyl | tert-Butyl |
| CAM | Cerium ammonium molybdate |
| DCM | Dichloromethane |
| DMAP | N,N-dimethylaminopyridine |
| DMSO | Dimethylsulfoxide |
| DMF | Dimethylformamide |
| DNA | Deoxyribonucleic acid |
| EDAC | 1-[3-(dimethylamino)propyl]-3-ethylcarbodiimide hydrochloride |
| EtOAc | Ethyl acetate |
| EtOH | Ethyl alcohol |
| g | Gram |
| h | hour |
| HIV-1, -2 | Human immunodeficiency virus type 1, type 2 |
| HOBt | 1-Hydroxybenzotriazole |
| HPLC | High performance liquid chromatography |
| HTLV-I, -II | Human T-cell lymphotropic virus type I, type II |
| IL-2 | Interleukin-2 |
| Kg | Kilogram |
| L | Liter |
| LC-MS | Liquid chromatography-mass spectrometry |
| M | Molar |
| MeOH | Methyl alcohol |
| mg | Milligram |
| mp | Melting point |
| min | Minute |
| Moc | Methoxycarbonyl |
| mol | Mole |
| mL | Milliliter |
| mmol | Millimole |
| nm | Nanometer |
| nM | Nanomolar |
| po | Orally |
| rEPO | Recombinant erythropoietin |
| TLC | Thin layer chromatography |
| 3TC | 2',3'-Dideoxy-3-thiacytidine |
| TFA | Trifluoroacetic acid |
| THF | Tetrahydrofuran |

DETAILED DESCRIPTION

Examples

This section describes the synthesis of several compounds and their prodrugs useful HIV aspartyl protease inhibitors. These examples are for the purpose of illustration only and are not to be construed as limiting the scope of the invention in any way.

Materials and Methods

Analytical thin layer chromatography (TLC) was carried out with 0.25 mm silica gel E. Merck 60 $F_{254}$ plates and eluted with the indicated solvent systems. Preparative chromatography was performed by flash chromatography, using silica gel 60 (EM Science) with the indicated solvent systems and positive air pressure to allow proper rate of elution. Detection of the compounds was carried out by exposing eluted plates (analytical or preparative) to iodine, UV light and/or treating analytical plates with a 2% solution of p-anisaldehyde in ethanol containing 3% sulfuric acid and 1% acetic acid followed by heating. Alternatively, analytical plates can be treated with a 0.3% ninhydrin solution in ethanol containing 3% acetic acid and/or a CAM solution made of 20 g $(NH_4)_6Mo_7O_{24}$ and 8.3 g $Ce(SO_4)_2$ polyhydrate in water (750 mL) containing concentrated sulfuric acid (90 mL).

Preparative HPLC were perform on a Gilson apparatus equipped with a C18 column, a 215 liquid handler module and 25 mL/min capacity head pumps. The HPLC is operated with a Gilson UniPoint System Software.

Semi-Preparative HPLC Conditions for Purification of Test Compounds:

HPLC system: 2 Gilson #305-25 mL pumps, Gilson #215 liquid handler for injection and collection and a Gilson #155 UV-Vis absorbance detector, all controlled from a Gilson Unipoint V1.91 software Column: Alltech (#96053) Hyperprep PEP, C-18, 100 Åα, 8 μm, 22×250 mm Flow: 15 mL/min Solvents: A: $H_2O$; B: $CH_3CN$ Gradient: 25% to 80% of B over 40 min Detector: absorbance; λ: 210 & 265 nm The crude material dissolved in acetonitrile to a concentration of around 50 to 80 mg/2 mL were injected in each run. Fractions were collected in amounts of 9 mL pertaining absorbance was detected at the UV detector.

Unless otherwise indicated, all starting materials were purchased from a commercial source such as Aldrich Co. or Sigma Co.

Melting points (mp) were determined on a Büchi 530 melting point apparatus in capillary tubes and were uncorrected.

Mass spectra were recorded on a Hewlett Packard LC/MSD 1100 system using APCI or electrospray sources either in negative mode or positive mode.

Nuclear magnetic resonance (NMR) spectra were recorded on a Bruker AMX-II-500 equipped with a reversed or QNP probe. Samples were dissolved in deuterochloroform ($CDCl_3$), deuteroacetone (acetone-$d_6$), deuteromethanol ($CD_3OD$) or deuterodimethylsulfoxide (DMSO-$d_6$) for data acquisition using tetramethylsilane as internal standard. Chemical shifts (*) are expressed in parts per million (ppm), the coupling constants (J) are expressed in hertz (Hz) whereas multiplicities are denoted as s for singlet, d for doublet, 2d for two doublets, dd for doublet of doublets, t for triplet, q for quartet, quint. for quintet, m for multiplet, and br s for broad singlet.

DETAILED DESCRIPTION OF THE INVENTION

General Procedures

General Procedure for the Preparation of Test Compounds

A. General Coupling Procedure with HOBt and EDAC

Method used in scheme 1 of this invention.

To the acid to be condensed (0.8 eq.) and 1-hydroxybenzotriazole (25 mg, 0.18 mmol, 1.2 eq.) in solution in 1 mL of dichloromethane and few drops of dimethylformamide, the minimum as to solubilize the reagents, was added 1-[3-(dimethylamino)propyl]-3-ethylcarbodiimide hydrochloride (EDAC) (26 mg, 0.14 mmol, 0.9 eq). The mixture was stirred for 15 min before addition of the amine ((1S)-4-amino-N-(4-amino-1-hydroxymethyl-butyl)-N-isobutyl-benzenesulfonamide (VII, example 1, step F)) (50 mg, 0.15 mmol) in 1 mL DMF. The resulting mixture was stirred for several hours, generally overnight, before pouring into an extraction funnel containing 15 mL hydrochloric acid 1.0 N and 30 mL ethyl acetate and extracted. The organic layers were washed with 20 mL of water, dried over magnesium sulfate, filtered and evaporated. The crude mixture was purified by reverse phase semi-preparative HPLC under the conditions described in the materials and methods section. The fractions containing the desired compound were combined and evaporated. The residue was taken up in a minimal amount of acetonitrile, diluted with water and lyophilized.

B. General Coupling Procedure with HOBt and EDAC

Method used in scheme 2 of this invention.

To a suitable vessel was added 100 mg N-substituted amino acids, and a 1 mL aliquot of DMF, 150 mg EDAC, 75 mg HOBt were added. After 30 min at 40° C. 1.5 eq. of the amino amide/acid, (1S)-4-amino-N-(5-amino-1-carboxylamido-pentyl)-N-isobutyl-benzenesulfonamide (step D) was added along with 100 mg N-methyl morpholine. The solution was then stirred at 23° C. for 4-12 h. A 1M $K_2CO_3$ (20 mL aliquot) is added and left for 1 h. Then, EtOAc is added (50 mL). The aqueous phase is separated and extracted with citric acid (10%) 50 mL. The organic phase was separated and evaporated. The residue was purified by semi-preparative HPLC and lyophilized.

C. Preparation of Amides and Sulphonamides Using Acid Chlorides and Sulphonyl Chlorides To the amine dissolved in dichloromethane and N,N-dimethylformamide (DMF), the minimum as to dissolve the product, were added 1.5 eq. of diisopropylethylamine and the mixture cooled in an ice bath under stirring for 10-15 min. The acid/sulphonyl chloride (1.1 eq.) was added dropwise and the reaction continued at 0° C. for 20-30 min and at room temperature an additional 2-4 hours. The reaction mixture was poured into an extraction funnel containing aqueous 1.0N sodium hydroxide and EtOAc and separated. The organic layer was washed with 1.0N hydrochloric acid, with brine, and then dried over magnesium sulfate. The crude product obtained after evaporation was generally purified by semi-preparative HPLC as described earlier (see materials and methods section).

D. Alternative Procedure for the Preparation of Amide Derivatives from Acid Chloride In a dried flask and under nitrogen atmosphere, dry acetonitrile (1 mL), triethylamine (4 eq.) and N-hydroxybenzotriazole (1.2 eq.) were added and stirred at room temperature. The corresponding acid chloride (1.1 eq.) was added slowly and the mixture was stirred for 30 minutes. The amine (product of example 8 (1 eq.) or other appropriate amine) was then added and the mixture was stirred until completion by TLC (100% EtOAc). The mixture was poured into an extracting funnel containing 50 mL of ethyl acetate. The organic layers were washed with water, saturated $NaHCO_3$ and brine, dried over sodium sulfate, filtered and evaporated. The crude mixture was purified by flash chromatography with 100% AcOEt.

E. General Procedure for the Preparation of Amide Derivatives from Acid

N-Hydroxybenzotriazole (1.9 eq.), 1-[3-(dimethylamino) propyl]-3-ethylcarbodiimide hydrochloride (EDAC) (2.5 eq.) and the corresponding carboxylic acid (0.8 eq.) were added to 1 mL of N,N-dimethylformamide and stirred at room temperature for 30-60 minutes. The amine (product of example 8 (1 eq.) or other appropriate amine) was then added and the mixture was stirred until completion by TLC (100% EtOAc). The mixture was poured into an extracting funnel with 50 mL of ethyl acetate. The organic layers were washed with water, saturated $NaHCO_3$ and brine, dried over sodium sulfate, filtered and evaporated. The crude mixture was purified by flash chromatography with 100% EtOAc.

F. General Procedure for the Preparation of Secondary Amine Derivatives from Aldehydes (5S)-2-Amino-N-{5-[(4-amino-benzenesulfonyl)-isobutyl-amino]-6-hydroxy-hexyl}-3-naphthalen-2-yl-propionamide (or the product of example 8 for the ornithine derivatives or other amine) (1.0 eq.) was added to dichloromethane (1 mL) and stirred at 0° C. The corresponding aldehyde (1.0 eq.) and acetic acid (1.0 eq.) were added to the mixture. After stirring for 10 minutes, sodium triacetoxyborohydride (1.5 eq.) was added and the mixture stirred until completion by TLC (100% EtOAc). The solvent was evaporated and the crude mixture was purified by reverse phase semi-preparative HPLC under the conditions described in the Materials and Methods section.

G. General Procedure for the Preparation of Carbamates from Alcohols

In a dried flask and under inert atmosphere, the alcohol was dissolved in dry dichloromethane (0.2M) and dissuccinimidyl carbonate (1.0 eq.) was added. The mixture was stirred at room temperature for 2-3 hours before addition of the solid amine. The mixture was stirred an additional hour and then poured in an extraction funnel containing 1.0N sodium hydroxide and ethyl acetate and extracted. The organic layer was washed with a 1.0N hydrochloric acid solution (if the alcohol moiety do not bear a basic site) and with brine, dried with magnesium sulphate, filtered and evaporated to dryness. The crude residue was then purified by semi-preparative HPLC using the conditions described in the Materials and Methods section.

EXAMPLES

Step A. Preparation of (3S)-3-isobutylamino-azepan-2-one (IV)

L-α-amino-,-caprolactam (22.0 g) was dissolved in cold dichloromethane (DCM, 200 mL). isobutyraldehyde (12.6 g) was added slowly and stirred until the heat evolved was dissipated (water forms at the surface). The cold solution was added to 46.5 g of powdered $NaBH(OAc)_3$ in DCM (0.5 L). AcOH (70 mL) was added to the solution. The slightly turbid mixture was stirred at 20° C. for 4 h. A 500 mL solution of 2M NaOH was added slowly to the turbid mixture and the pH adjust to 11 using a concentrated NaOH solution, and then the mixture stirred for a further 20 min. After extraction, the DCM layer was dried with $MgSO_4$, filtered and evaporated. The oil thus obtained crystallizes slowly on standing (27.8 g, 85%) and was used without further purification in the next step.

$^1$H NMR ($CDCl_3$): δ 0.93 (d, J=6.5, 3H), 0.97 (d, J=6.5, 3H), 1.39 (t, J=9.8, 1H), 1.47 (m, 1H), 1.78-1.65 (m, 2H), 2.00-1.93 (m, 2H), 2.32-2.2 (m, 2H), 2.38 (t, J=9.7, 1H), 3.16 (m, 3H), 6.62 (s, 1H (NH)). mp 52-54° C. (hexanes).

A small sample was converted to the S-methyl benzyl urea by adding the solid to a solution of S-methyl benzyl isocyanate in MeCN. NMR gives 98% ee

Step B. Preparation of Nα-isobutyl-Nα-(4-acetamidobenzenesulfonyl)-L-α-amino-,-caprolactam (V)

Nα-isobutyl-L-α-amino-,-caprolactam (IV) (4.1 g free base) was dissolved in DCM (200 mL) and treated with 4.0 g triethylamine, followed by 4-acetamidobenzenesulfonyl chloride (5.2 g). A 0.1 g portion of dimethylaminopyridine was added and the mixture was stirred 5 h. The resulting thick slurry was poured into 500 mL 0.5 M HCl and shaken vigorously. The solid in the biphasic solution was filtered out and washed with cold acetone to give 7.3 g (87%) of clean product.

$^1$H NMR (DMSO-$d_6$): δ 0.93 (d, J=6.0, 3H), 0.96 (d, J=6.0, 3H), 1.39 (t, J=12.0, 1H), 1.85-1.65 (m, 3H), 2.08-2.18 (m and s, 6H), 2.90-2.97 (m, 1H), 3.00-3.06 (m, 2H), 3.35 (dd, J=14.2, 8.5, 1H), 4.65 (d, J=8.7, 1H), 6.3 (s, 1H), 7.42 (d, J=8.8, 2H), 7.6 (d, J=8.8, 2H). mp 230-233° C. (EtOH).

Step C. Preparation of (3S)-3-{[4-(acetyl-tert-butoxycarbonyl-amino)-benzenesulfonyl]-isobutyl-amino}-2-oxo-azepane-1-carboxylic acid tert-butyl ester (Boc activation) (VI)

4.2 g of Nα-isobutyl-Nα-(4-acetamidobenzenesulfonyl)-L-α-amino-,-caprolactam (V) was suspended in 30 mL MeCN and briefly sonicated to break up any large chunks. To this white suspension was added 6.7 g (3 eq.) of di-tert-butyl pyrocarbonate in 10 mL MeCN. The suspension was stirred with a magnetic bar and a 120 mg portion of DMAP was added. The solution becomes a clear light yellow after a few minutes. TLC (EtOAc) reveals 1 product Rf 0.9 (starting material Rf at 0.4). The solution is poured in distilled water 20 mL and extracted with ether, dried with $Na_2SO_4$ and evaporated yielding 6.90 g. A sample was recrystallized from hexanes.

$^1$H NMR (DMSO-$d_6$σ 0.68 (d, J=6.0, 3H), 0.85 (d, J=6.0, 3H), 1.39 (s, 10H), 1.47 (s, 9H), 1.85-1.65 (m, 3H), 2.15 (s, 3H), 2.80 (q, J=4, 1H), 3.10-3.36 (m, 2H), 4.01 (d, J=8.0, 1H), 4.85 (d, J=8.7, 1H), 7.32 (d, J=8.8, 2H), 7.87 (d, J=8.8, 2H). mp 123-124° C.

Step D. Preparation of (1S)-4-amino-N-(5-amino-1-hydroxymethyl-pentyl)-N-isobutyl-benzenesulfonamide (VII-deprotected) (reductive ring opening and deprotection)

A 3.0 g portion of (3S)-3-{[4-(acetyl-tert-butoxycarbonyl-amino)-benzenesulfonyl]-isobutyl-amino}-2-oxo-azepane-1-carboxylic acid tert-butyl ester (VI, step C) is dissolved in 40 mL EtOH followed by 750 mg $NaBH_4$. Brief heating with a heat gun gives a clear solution. TLC reveals one streaky spot after 20 min (EtOAc). The solution is concentrated to a paste, poured in 40 mL 1N NaOH and extracted with ethyl acetate, the organic phase dried with $NaSO_4$ and evaporated to give 2.8 g of product intermediate (VII); (1S)-{4-[(5-tert-butoxycarbonylamino-1-hydroxymethyl-pentyl)-isobutyl-sulfamoyl]-phenyl}-carbamic acid tert-butyl ester (VII).

The above product intermediate is dissolved in 5 mL EtOH and 5 mL 12 N HCl is added. Vigorous gas evolution is observed for a few minutes. After 2 h the solution is evaporated and rendered basic with concentrated KOH and extracted with EtOAc yielding 1.75 g of a white powder.

$^1$H NMR (DMSO-$d_6$): σ 0.82 (m, 6H), 0.97-1.12 (m, 2H), 1.15-1.30 (m, 3H), 1.57 (m, 1H), 1.84 (m, 1H), 2.40 (t, J=7.8, 2H), 2.75 (m, 1H), 2.85 (m, 1H), 3.21 (m, 1H), 3.44 (d, J=6.4, 2H), 5.92 (br s, 2H), 6.59 (d, J=8.0, 2H), 7.39 (d, J=8.0, 2H).

Step A

The preparation of the title is based on scheme 4 of this invention.

(1S,5S)-(1-{5-[(4-amino-benzenesulfonyl)-isobutyl-amino]-6-hydroxy-hexylcarbamoyl}-2-naphthalen-2-yl-ethyl)-carbamic acid tert-butyl ester (698 mg, 1.089 mmol) was added to 6 mL of ethanol and 6 mL of HCl. The mixture was stirred at room temperature until completion by TLC. The ethanol was evaporated and the acidic mixture was poured into an extracting funnel containing 75 mL of ethyl acetate and 50 mL of HCl 1M and separated. The aqueous layer was washed with ethyl acetate. The aqueous phase was basified with pellets of NaOH and poured into an extracting funnel. The organic layer was washed with NaOH 1M and brine, dried over sodium sulfate, filtered, evaporated and dried under vacuum to give 544 mg (92%) of a yellow solid (Rf=0, 100% EtOAc, indicator: ninhydrin).

Step A, Preparation of Nα-isobutyl-Nα-(3,4-methylenedioxybenzenesulfonyl)-L-α-amino-,-caprolactam (2S)-3-Isobutylamino-azepan-2-one (example 28, step A) 1.0 g was dissolved in DCM (20.0 mL) and treated with 2 ml triethylamine followed by the addition of 3,4-methylenedioxybenzenesulfonyl chloride (900 mg). A 0.05 g portion of DMAP was added and the mixture was stirred 5 h. The resulting solution was poured into mL 0.5 M HCl and shaken vigorously. The organic phase was dried and evaporated to give (1.30 mg) of clean product.

$^1$H NMR (DMSO-$d_6$): * 0.93 (d, J=6.0, 3H), 0.96 (d, J=6.0, 3H), 1.26-1.47 (m, 1H), 1.85-1.65 (m, 3H), 2.08-2.28 (m and s, 6H), 2.97-3.07 (m, 1H), 3.11-3.33 (m, 3H), 4.65 (d, J=9.0, 1H), 6.02 (s, 2H), 6.88 (d, J=6.6, 1H), 7.14 (s, 1H), 7.30 (d, J=6.7 1H).

Step B

Specific Examples for the Preparation of Derivatives of General Formula I

The following prodrugs were prepared from L-lysine derivatives using the procedures summarized herein.

Example 1

Preparation of (1S,5S)-[1-{5-[(4-amino-benzenesulfonyl)-isobutyl-amino]-6-phosphonooxy-hexylcarbamoyl}-2-(2-bromo-phenyl)-ethyl]-carbamic acid methyl ester Step A. Preparation of (2S)-3-(2-bromo-phenyl)-2-methoxycarbonylamino-propionic acid (or L-Moc-2-bromophenylalanine)

1.0 g L-2-bromophenylalanine (Peptech Corp.) is dissolved in 6 mL 1M $K_2CO_3$ followed by 0.77 g methoxycarbonyloxysuccinimide in 20 mL acetone. The resulting clear biphasic solution is stirred for 4 h, then concentrated to 10 mL. The resulting basic solution is extracted with ether and the aqueous phase rendered acidic with 6 M HCl. The oily precipitate is extracted with EtOAc (2×20 mL) and evaporated to yield 1.16 g of a clear oil which crystallizes upon standing.

$^1$H NMR ($CD_3OD$): δ 2.94-3.02 (m, 1H), 3.30-3.36 (m, 1H), 3.51 (s, 3H) 4.52 (t, J=7.6, 1H), 7.04 (t, J=6.8 1H), 7.20-7.26 (m, 2H), 7.52 (d, J=7.0, 2H).

Step B. Preparation of (1S,5S)-[1-{5-[(4-amino-benzenesulfonyl)-isobutyl-amino]-6-phosphonooxy-hexylcarbamoyl}-2-(2-bromo-phenyl)-ethyl]-carbamic acid methyl ester This compound was prepared as for the preparation of the product of example 3 (step D) with 100 mg of L-Moc-2-bromophenylalanine (step A of this example). The resulting precipitated residue was further purified by reverse phase preparative HPLC. Yields 25 mg of the title compound.

LC-MS: 693.1 $(M+H)^+$, 95% pure.

$^1H$ NMR ($CD_3OD$): δ 0.89-0.98 (m, 7H), 1.00-1.15 (m, 2H), 1.26-1.35 (m, 2H), 1.45-1.52 (m, 1H), 1.62-1.70 (m, 1H), 1.88-1.95 (m, 1H), 2.74-2.98 (m, 3H), 2.98-3.16 (m, 3H), 3.20-3.29 (m, 1H), 3.56 (s, 3H), 3.67-3.74 (m, 1H), 3.81-3.89 (m, 1H), 3.99-4.05 (m, 1H), 4.39 (t, J=7.0, 1H), 6.75 (d, J=8.0, 2H), 7.10-7.17 (m, 1H), 7.24 (s, 1H), 7.50 (d, J=8.0, 2H), 7.58-7.61 (m, 1H).

$^{31}P$ NMR ($CD_3OD$): δ 2.75

Example 2

Preparation of (2S,2S) phosphoric acid mono-(2-[(4-aminobenzenesulfonyl)-isobutyl-amino]-6-{3-(2-bromo-phenyl)-2-[(2-methyl-pyridine-3-carbonyl)-amino]-propionylamino}-hexyl)ester The title derivative was prepared as for the synthesis of the product of example 3 (step D) with 100 mg of 3-(2-bromo-phenyl)-2-[(2-methyl-pyridine-3-carbonyl)-amino]-propionic acid. Yields 70 mg of the title compound. The 3-(2-bromo-phenyl)-2-[(2-methyl-pyridine-3-carbonyl)-amino]-propionic acid starting material was easily prepared from the coupling of L-2-bromophenylalanine (Peptech Corp.) and 2-methyl-nicotinoyl chloride.

LC-MS: 769.6 $(M+H)^+$, 95% pure.

$^1H$ NMR ($CD_3OD$): δ 0.83-0.99 (m, 8H), 1.00-1.15 (m, 2H), 1.26-1.35 (m, 2H), 1.45-1.52 (m, 1H), 1.62-1.70 (m, 1H), 1.88-1.95 (m, 1H), 2.84-2.98 (m, 2H), 2.98-3.86 (m, 3H), 3.20-3.29 (m, 1H), 3.56 (s, 3H), 3.67-3.69 (m, 1H), 3.81-3.89 (m, 1H), 3.99-4.05 (m, 1H), 4.99 (t, J=7.0, 1H), 6.68 (d, J=8.0, 2H), 7.03-7.32 (m, 4H), 7.50 (d, J=8.0, 1H), 7.57 (t, J=7.8, 1H), 7.71 (t, J=7.8, 1H), 8.43 (d, J=7.8 1H).

$^{31}P$ NMR ($CD_3OD$): δ 2.68

Example 3

Preparation of (2S,2S) phosphoric acid mono-(2-[(4-aminobenzenesulfonyl)-isobutyl-amino]-6-{3-(2-bromo-phenyl)-2-[(pyridine-4-carbonyl)-amino]-propionylamino}-hexyl)ester This compound was done as for the preparation of the product of example 3 (step D) with 100 mg of L-3-(2-bromo-phenyl)-2-[(pyridine-4-carbonyl)-amino]-propionic acid. The precipitated residue was further purified by reverse phase preparative HPLC. Yields 65 mg of the desired material. The L-3-(2-bromo-phenyl)-2-[(pyridine-4-carbonyl)-amino]-propionic acid starting material was easily prepared from the combination of L-2-bromophenylalanine (Peptech Corp.) and isonicotinoyl chloride mono hydrochloride (Aldrich).

LC-MS: 755.8 $(M+H)^+$, 95% pure.

$^1H$ NMR ($CD_3OD$): δ 0.83-0.99 (m, 8H), 1.00-1.15 (m, 2H), 1.26-1.35 (m, 2H), 1.45-1.52 (m, 1H), 1.62-1.70 (m, 1H), 1.88-1.95 (m, 1H), 2.84-2.98 (m, 2H), 2.98-3.86 (m, 3H), 3.20-3.29 (m, 1H), 3.56 (s, 3H), 3.67-3.69 (m, 1H), 3.81-3.89 (m, 1H), 3.99-4.05 (m, 1H), 4.99 (t, J=7.0, 1H), 6.68 (d, J=8.0, 2H), 7.03-7.32 (m, 4H), 7.50 (d, J=8.0, 1H), 7.70 (d, J=7.8, 2H), 8.73 (d, J=7.8 2H).

$^{31}P$ NMR ($CD_3OD$): δ 3.28

Example 4

Preparation of (1S,5S)-[1-{5-[(4-amino-benzene-sulfonyl)-isobutyl-amino]-6-phosphonooxy-hexyl-carbamoyl}-2-(2-fluoro-phenyl)-ethyl]-carbamic acid methyl ester The title compound was synthesized as for the preparation of the product of example 3 (step D) with 100 mg of L-3-(2-fluoro-phenyl)-2-methoxycarbonylamino-propionic acid (or L-Moc-2-fluorophenylalanine). Yields 14.5 mg 35% of the desired material. The L-3-(2-fluoro-phenyl)-2-methoxycarbonylamino-propionic acid starting material was easily prepared from the combination of L-2-fluorophenylalanine (Peptech Corp.) and methoxycarbonyloxysuccinimide as in example 4 (step A).

LC-MS: 647.2 $(M+H)^+$, 95% pure.

$^1H$ NMR ($CD_3OD$): δ 0.90 (d, J=3.5, 6H), 0.95-1.01 (m, 1H), 1.02-1.11 (m, 1H), 1.25-1.32 (m, 2H), 1.40-1.49 (m, 1H), 1.56-1.67 (m, 1H), 1.86-1.95 (m, 1H), 2.82-2.90 (m, 1H), 2.90-2.96 (m, 2H), 2.98-3.03 (m, 1H), 3.08-3.14 (m, 2H), 3.59 (s, 3H), 3.74-3.76 (m, 1H), 3.88-3.92 (m, 1H), 4.02-4.06 (m, 1H), 4.33-4.35 (m, 1H), 6.74 (d, J=8.2, 2H), 7.04-7.12 (m, 2H), 7.25-7.30 (m, 2H), 7.53 (d, J=8.2, 2H).

$^{31}P$ NMR ($CD_3OD$): δ 2.75

Example 5

Preparation of (1S,5S) [1-{5-[(4-amino-benzene-sulfonyl)-isobutyl-amino]-6-phosphonooxy-hexyl-carbamoyl}-2-(2-chloro-phenyl)-ethyl]-carbamic acid methyl ester This derivative was made as for the preparation of the product of example 3 (step D) with 100 mg of L-3-(2-chloro-phenyl)-2-methoxycarbonylamino-propionic acid (or L-Moc-2-chlorophenylalanine). Yields 71 mg of the desired material. The L-3-(2-chloro-phenyl)-2-methoxycarbonylamino-propionic acid starting material was easily prepared from the combination of L-2-chlorophenylalanine (Peptech Corp.) and methoxycarbonyloxysuccinimide as in example 4 (step A).

LC-MS: 664.3 $(M+H)^+$, 95% pure.

$^1H$ NMR ($CD_3OD$): δ 0.89-0.98 (m, 8H), 1.00-1.15 (m, 2H), 1.26-1.35 (m, 2H), 1.45-1.52 (m, 1H), 1.62-1.70 (m, 1H), 1.88-1.95 (m, 1H), 2.84-2.98 (m, 2H), 2.98-3.06 (m, 3H), 3.20-3.29 (m, 1H), 3.56 (s, 3H), 3.67-3.69 (m, 1H), 3.81-3.89 (m, 1H), 3.99-4.05 (m, 1H), 4.39 (t, J=7.0, 1H), 7.05 (d, J=8.0, 2H), 7.16-7.25 (m, 3H), 7.34 (s, 1H), 7.75 (d, J=8.0, 2H).

$^{31}P$ NMR ($CD_3OD$): δ 2.47

Example 6

Preparation of (1S,5S) [1-{5-[(4-amino-benzene-sulfonyl)-isobutyl-amino]-6-phosphonooxy-hexyl-carbamoyl}-2-(4-bromo-phenyl)-ethyl]-carbamic acid methyl ester This derivative was synthesized using the procedure described for the preparation of (1S,5S)-[1-{5-[(4-amino-benzenesulfonyl)-isobutyl-amino]-6-phosphonooxy-hexyl-carbamoyl}-2-(2-bromo-phenyl)-ethyl]-carbamic acid methyl ester (example 4, steps A and B) using L-4-bromophenylalanine (Peptech Corp.) instead of L-2-bromophenylalanine. The desired material was obtained in 28% yield (25 mg)

LC-MS: 707.0 $(M+H)^+$, 95% pure.

$^1H$ NMR ($CD_3OD$): δ 0.90 (d, J=5.9, 6H), 1.00-1.17 (m, 2H), 1.20-1.30 (m, 2H), 1.39-1.50 (m, 1H), 1.55-1.69 (m, 1H), 1.86-1.99 (m, 1H), 2.79-2.90 (m, 2H), 2.91-3.11 (m, 4H), 3.59 (s, 3H), 3.75-3.79 (m, 1H), 3.86-3.92 (m, 1H), 4.02-4.08 (m, 1H), 4.20-4.30 (m, 1H), 6.76 (d, J=8.2, 2H), 7.15 (d, J=7.8, 2H), 7.42 (d, J=7.8, 2H), 7.54 (d, J=8.2, 2H).

$^{31}P$ NMR ($CD_3OD$): δ 2.74

Example 7

This compound was prepared based on Scheme 2

Preparation of (1S)-4-amino-N-(5-amino-1-carboxamido-pentyl)-N-isobutyl-benzenesulfonamide (reductive ring opening and deprotection)

A 3.0 g portion of (3S)-3-{[4-(acetyl-tert-butoxycarbonyl-amino)-benzenesulfonyl]-isobutyl-amino}-2-oxo-azepane-1-carboxylic acid tert-butyl ester (VI, step C) is dissolved in 40 mL EtOH followed by 1 mL $NH_4OH_{conc}$. Brief heating with a heat gun gives a clear solution. TLC reveals one streaky spot after 20 min (EtOAc). The solution is concentrated to a paste, poured in 40 mL 1N NaOH and extracted with ethyl acetate, the organic phase dried with $NaSO_4$ and evaporated to give 2.8 g of product intermediate; (1S)-{4-[(5-tert-butoxycarbonylamino-1-hydroxymethyl-pentyl)-isobutyl-sulfamoyl]-phenyl}-carbamic acid tert-butyl ester (VII).

The above product intermediate is dissolved in 5 mL EtOH and 5 mL 12 N HCl is added. Vigorous gas evolution is observed for a few minutes. After 2 h the solution is evaporated and rendered basic with concentrated KOH and extracted with EtOAc yielding 1.75 g of a white powder.

100 mg portion of the above was added to a solution of 100 mg Moc-Dip in 2 mL DMF containing 2 eq of EDAC and 1 eq HOBt. The solution was reacted for 30 min and poured into 1 M K2CO3. The turbid solution was extracted with EtOAc and the organic phase dried with Na2SO4 the evaporated to dryness. The residue was then purified by RP-HPLC.

LC-MS: 638.3 $(M+H)^+$, 95% pure

Example 8

This compound was prepared based on Scheme 2

As in example 7 using Acetyl-DIP.

LC-MS: 622.4 $(M+H)^+$, 95% pure

Example 9

This compound was prepared based on Scheme 2

LC-MS: 667.4 $(M+H)^+$, 95% pure

Example 10

This compound was prepared based on Scheme 2

LC-MS: 639.2 $(M+H)^+$, 95% pure

Example 11

This compound was prepared based on Scheme 1 and 3

The compound was prepared from general procedure A using (2S)-2-tert-butoxycarbonylamino-2-naphthyl-propionic acid and (1S)-4-amino-N-(5-amino-1-hydroxymethyl-pentyl)-N-isobutyl-benzenesulfonamide (above) but the product was purified by flash chromatography yielding 49% of the Boc derivative. This product was treated with trifluoroacetic acid to give the amine in 96% yield using the same conditions as described for the preparation of (2S,4S)-2-amino-N-{4-[(4-amino-benzenesulfonyl)-isobutyl-amino]-5-hydroxy-pentyl}-2-naphthyl-propionamide. The product was used without further purification. The product was reacted with benzene sulfonyl chloride using general procedure C.

LC-MS: 682.1 $(M+H)^+$, 95% pure

Example 12

This compound was prepared based on Scheme 1 and 3

Prepared as in example 11 using 2-thiophene-sulphonyl chloride through general procedure C.

LC-MS: 688.1 $(M+H)^+$, 95% pure

Example 13

This compound was prepared based on Scheme 1

LC-MS: 594.4 $(M+H)^+$, 95% pure

Example 14

This compound was prepared based on Scheme 1

LC-MS: 623.4 $(M+H)^+$, 95% pure

Example 15

This compound was prepared based on Scheme 1 and 3

LC-MS: 681.8 $(M+H)^+$, 95% pure

Example 16

This compound was prepared based on Scheme 1

LC-MS: 697.9 $(M+H)^+$, 95% pure

Example 17

This compound was prepared based on Scheme 1

LC-MS: 710.8 $(M+H)^+$, 95% pure

Example 18

This compound was prepared based on Scheme 1 and 3

The compound was prepared from general procedure A using (2S)-2-tert-butoxycarbonylamino-2-bromophenyl-propionic acid and (1S)-4-amino-N-(5-amino-1-hydroxymethyl-pentyl)-N-isobutyl-benzenesulfonamide (above) but the product was purified by flash chromatography. This product was treated with trifluoroacetic acid to give the amine in 96% yield using the same conditions as described for the preparation of (2S,4S)-2-amino-N-{4-[(4-amino-benzenesulfonyl)-isobutyl-amino]-5-hydroxy-pentyl}-2bromophenyl-propionamide. The product was used without further purification. The product was reacted with 3-hydroxy-2-methyl benzoic acid using general procedure E.

LC-MS: 704.8 $(M+H)^+$, 95% pure

Example 19

This compound was prepared based on Scheme 1 and 3

As in example 18 using 6-hydroxy-2-picolinic acid through general procedure E

LC-MS: 691.8 $(M+H)^+$, 95% pure

Example 20

This compound was prepared based on Scheme 1 and 3

The compound was prepared from general procedure A using (2S)-2-tert-butoxycarbonylamino-(2-methyl-phenyl)-propionic acid and (1S)-4-amino-N-(5-amino-1-hydroxymethyl-pentyl)-N-isobutyl-benzenesulfonamide (above) but the product was purified by flash chromatography. This product was treated with trifluoroacetic acid to give the amine in 96% yield using the same conditions as described for the preparation of (2S,4S)-2-amino-N-{4-[(4-amino-benzenesulfonyl)-isobutyl-amino]-5-hydroxy-pentyl}-(2-methyl-phenyl)propionamide. The product was used without further purification. The product was reacted with nicotinic acid using general procedure E.

LC-MS: 610.8 $(M+H)^+$, 95% pure

Example 21

This compound was prepared based on Scheme 1 and 3

As in example 20 using 6-methyl-nicotinic acid through general procedure E

LC-MS: 624.8 $(M+H)^+$, 95% pure

Example 22

This compound was prepared based on Scheme 1 and 3

As in example 20 using 4-picolinic acid through general procedure E

LC-MS: 610.8 $(M+H)^+$, 95% pure

Example 23

This compound was prepared based on Scheme 1 and 3

As in example 20 using 2-hydroxy-3-methyl benzoic acid through general procedure E LC-MS: $(M+H)^+$, 95% pure Example 24

This compound was prepared based on Scheme 1 and 3

The compound was prepared from general procedure A using (2S)-2-tert-butoxycarbonylamino-(cyclohexyl)-propionic acid and (1S)-4-amino-N-(5-amino-1-hydroxymethyl-pentyl)-N-isobutyl-benzenesulfonamide (above) but the product was purified by flash chromatography. This product was treated with trifluoroacetic acid to give the amine in 96% yield using the same conditions as described for the preparation of (2S,4S)-2-amino-N-{4-[(4-amino-benzenesulfonyl)-isobutyl-amino]-5-hydroxy-pentyl}-(cyclohexyl)propionamide. The product was used without further purification. The product was reacted with methyl chloroformate using general procedure C.

LC-MS: 639.8 $(M+H)^+$, 95% pure

Example 25

This compound was prepared based on Scheme 1 and 3

As in example 24 using nicotinic acid through general procedure E

LC-MS: 602.8 $(M+H)^+$, 95% pure

Example 26

This compound was prepared based on Scheme 1 and 3

As in example 24 using 6-methylnicotinic acid through general procedure E

LC-MS: 616.8 $(M+H)^+$, 95% pure

Example 27

This compound was prepared based on Scheme 1

LC-MS: $(M+H)^+$, 95% pure

Example 28

This compound was prepared based on Scheme 1

Preparation of (1S)-benzo[1,3]dioxole-5-sulfonic acid (5-amino-1-hydroxymethyl-pentyl)-isobutyl-amide This compound was prepared from Nα-isobutyl-Nα-(3,4-methylenedioxybenzenesulfonyl)-L-α-amino-,-caprolactam (step A) in a three step reaction sequence (Boc activation, reductive ring opening and deprotection) as described for the preparation of (1S)-4-amino-N-(5-amino-1-hydroxymethyl-pentyl)-N-isobutyl-benzenesulfonamide (example 28, steps C and D). The final product was obtained in 75% yield and was used as such in the next step.

LC-MS: 717.8 $(M+H)^+$, 95% pure

Example 29

This compound was prepared based on Scheme 1 and 3

The compound was prepared from general procedure A using (2S)-2-tert-butoxycarbonylamino-2-chlorophenyl-propionic acid and (1S)-4-amino-N-(5-amino-1-hydroxymethyl-pentyl)-N-isobutyl-benzenesulfonamide (above) but the product was purified by flash chromatography. This product was treated with trifluoroacetic acid to give the amine in 96% yield using the same conditions as described for the preparation of (2S,4S)-2-amino-N-{4-[(4-amino-benzenesulfonyl)-isobutyl-amino]-5-hydroxy-pentyl}-2-chlorophenyl-propionamide. The product was used without further purification. The product was reacted with 4-picolinic acid using general procedure E.

LC-MS: 630.2 $(M+H)^+$, 95% pure

Example 30

This compound was prepared based on Scheme 1 and 3

As in example 29 using 2-methylnicotinic acid through general procedure E

LC-MS: 645.2 $(M+H)^+$, 95% pure

Example 31

This compound was prepared based on Scheme 1

LC-MS: 727.2 $(M+H)^+$, 95% pure

Example 32

This compound was prepared based on Scheme 1

LC-MS: 652.3 $(M+H)^+$, 95% pure

Example 33

This compound was prepared based on Scheme 1

Preparation of (3S)-3-(4-pyridylmethyl)lamino-azepan-2-one intermediate was effected as in the synthesis (3S)-3-isobutylamino-azepan-2-one using pyridine-4 carbaldehyde.

LC-MS: 660.3 $(M+H)^+$, 95% pure

Example 34

This compound was prepared based on Scheme 1

LC-MS: 707.3 $(M+H)^+$, 95% pure

Example 35

This compound was prepared based on Scheme 1

LC-MS: 681.8 $(M+H)^+$, 95% pure

Example 36

This compound was prepared based on Scheme 1 and 3

As in example 18 using 3-methyl-2 picolinic acid through general procedure E

LC-MS: 689.3 $(M+H)^+$, 95% pure

Example 37

This compound was prepared based on Scheme 1 and 3

As in example 18 using 3-hydroxy-4-methyl benzoic acid through general procedure E LC-MS: 704.3 $(M+H)^+$, 95% pure Example 38

This compound was prepared based on Scheme 1 and 3

As in example 18 using 4-pyridine carbinol acid through general procedure G

LC-MS: 705.3 $(M+H)^4$, 95% pure

Example 39

This compound was prepared based on Scheme 1 and 3

As in example 18 using 2-methyl nicotinic acid through general procedure E

LC-MS: 689.3 $(M+H)^+$, 95% pure

Example 40

This compound was prepared based on Scheme 1 and 3

As in example 18 using 6-methyl nicotinic acid through general procedure E

LC-MS: 689.3 $(M+H)^+$, 95% pure

Example 41

This compound was prepared based on Scheme 1 and 3

As in example 18 using 3,4 methylene dioxybenzoic acid through general procedure E LC-MS: 718.3 $(M+H)^+$, 95% pure Example 42

This compound was prepared based on Scheme 1 and 3

As in example 18 using 4-picolinic acid through general procedure E

LC-MS: 675.3 $(M+H)^+$, 95% pure

Example 43

This compound was prepared based on Scheme 1 and 3

As in example 18 using 5-methyl-pyrazine carboxylic acid through general procedure E LC-MS: 690.3 $(M+H)^+$, 95% pure Example 44

This compound was prepared based on Scheme 1 and 3

As in example 18 using 2-pyrazine carboxylic acid through general procedure E

LC-MS: 676.3 $(M+H)^+$, 95% pure

Example 45

This compound was prepared based on Scheme 1 and 3

As in example 18 using 2-pyridine carboxylic acid through general procedure E

LC-MS: 675.3 $(M+H)^+$, 95% pure

Example 46

This compound was prepared based on Scheme 1 and 3

As in example 18 using nicotinic acid through general procedure E

LC-MS: 675.3 $(M+H)^+$, 95% pure

Enzymatic Assay for Determining the Inhibition Constant (Ki) of Synthetic Compounds Targeting the HIV Protease This is a fluorometric assay based on the cleavage by protease of a substrate carrying a donor group (EDANS) and an acceptor group (DABCYL) on each side of the cleavage site, interacting together through fluorescence resonance energy transfer (FRET) as described by Matayoshi et al. (Science 247:954-954, 1990).

After calculation of Vo and Vi, the inhibition constant (Ki) of the compound is determined using the equation of Henderson:

$$\frac{Vo}{Vi} = 1 + \frac{[I]}{Ki_{app}}$$

Where $$Ki = \frac{Ki_{app}}{\frac{1 + [S]}{Km}}$$

where Vo=the enzyme's initial velocity

Vi=the enzyme velocity in the presence of the inhibitory compound,

[I]=inhibitor concentration, [S]=substrate concentration, Km=Michaelis-Menten constant and $Ki_{app}$=apparent Ki Graphs are traced and the Ki determined using GraphPad Prism software v. 3.0.

Anti-Viral and Cytotoxicity Assays In Vitro

To evaluate the $EC_{50}$ of our compounds, various drug concentrations are incubated with the infected cell for six days and then the metabolic activity of the cells is monitored by the MTT assay. (See A. J. Japour et al., Antimicrobial Agents and Chemotherapy, 37, 1095-1101, 1993 and R. Pauwels et al. Journal of Virological Methods, 20, 309-321, 1988)

We use the laboratory viral strain NL4.3 as wild type virus and the cell line used is MT-4 which is a T-cell line highly sensitive to HIV-1. We also use some WT clinical strains. To address the resistance issue we assay the inhibitors with NL4.3 mutants which are designed to be resistant to specific commercially available inhibitors.

The same MTT assay is used to evaluate the $CCIC_{50}$ (cell culture of $IC_{50}$) of our compounds except that the virus is omitted.

The compounds listed in Table 1 were prepared as indicated above. The numbers of the compounds listed in Table 1 (Ex. No.) corresponds to the example numbers presented above.

The activities of the compounds are listed in Table 2, demonstrating their potential usefulness. The $CCIC_{50}$ are not shown in the table but it was found that the average $CCIC_{50}$ for HIV protease inhibitors of the invention was 30+/−20 M with a range of 6 to 100 μM. Ki, $IC_{50}$ and $EC_{50}$ results for compounds of formula I are presented in Table 2, illustrating their potential usefulness.

TABLE 1

Structures of exemplary embodiments of HIV aspartyl protease inhibitors in accordance with this invention

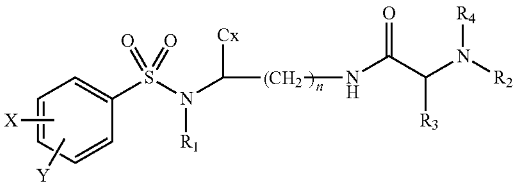
I

| Ex. - No. | X | Y | $R_1$ | Cx | $R_2$ | $R_3$ | $R_4$ | n | D, L, DL R, S, RS |
|---|---|---|---|---|---|---|---|---|---|
| 1 | H | 4-$NH_2$ | Iso-butyl- | —$CH_2O$—$(HO)_2P(O)$ | $CH_3O$—CO | 2-$BrC_6H_4CH_2$ | H | 4 | S, S |
| 2 | H | 4-$NH_2$ | Iso-butyl- | —$CH_2O$—$(HO)_2P(O)$ | 2-$CH_3$-3-pyridyl-CO | 2-$BrC_6H_4CH_2$ | H | 4 | S, S |
| 3 | H | 4-$NH_2$ | Iso-butyl- | —$CH_2O$—$(HO)_2P(O)$ | 4-Pyridyl-CO | 2-$BrC_6H_4CH_2$ | H | 4 | S, S |
| 4 | H | 4-$NH_2$ | Iso-butyl- | —$CH_2O$—$(HO)_2P(O)$ | $CH_3O$—CO | 2-$FC_6H_4CH_2$ | H | 4 | S, S |
| 5 | H | 4-$NH_2$ | Iso-butyl- | —$CH_2O$—$(HO)_2P(O)$ | $CH_3O$—CO | 2-$ClC_6H_4CH_2$ | H | 4 | S, S |
| 6 | H | 4-$NH_2$ | Iso-butyl- | —$CH_2O$—$(HO)_2P(O)$ | $CH_3O$—CO | 4-$BrC_6H_4CH_2$ | H | 4 | S, S |
| 7 | H | 4-$NH_2$ | Iso-butyl- | —$CONH_2$ | $CH_3O$—CO | $(C_6H_5)_2CH$ | H | 4 | S, S |
| 8 | H | 4-$NH_2$ | Iso-butyl- | —$CONH_2$ | $CH_3$—CO | $(C_6H_5)_2CH$ | H | 4 | S, S |
| 9 | H | 4-$NH_2$ | Iso-butyl- | —$CONH_2$ | 4-Morpholine-CO | Naphthyl-1-$CH_2$ | H | 4 | S, S |
| 10 | H | 4-$NH_2$ | Iso-butyl- | —COOH | $CH_3O$—CO | $(C_6H_5)_2CH$ | H | 4 | S, S |
| 47 | H | 4-$NH_2$ | Iso-butyl- | —$CH_2OH$ | 3-O—$CF_3$-Benzenesulfonyl | Naphthyl-2-$CH_2$ | H | 4 | |
| 48 | H | 4-$NH_2$ | Iso-butyl- | —$CH_2OH$ | 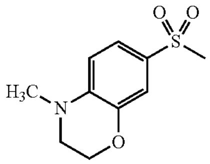 | Naphthyl-2-$CH_2$ | H | 4 | |
| 49 | H | 4-$NH_2$ | Iso-butyl- | —$CH_2OH$ | 2F-,4F-Benzenesulfonyl | Naphthyl-2-$CH_2$ | H | 4 | |
| 50 | H | 4-$NH_2$ | Iso-butyl- | —$CH_2OH$ | 3-MeO-4-MeO-benzenesulfonyl | Naphthyl-2-$CH_2$ | H | 4 | |
| 51 | H | 4-$NH_2$ | Iso-butyl- | —$CH_2OH$ | 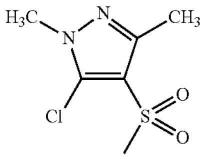 | Naphthyl-2-$CH_2$ | H | 4 | |
| 52 | H | 4-$NH_2$ | Iso-butyl- | —$CH_2OH$ | 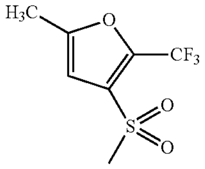 | Naphthyl-2-$CH_2$ | H | 4 | |
| 53 | H | 4-$NH_2$ | Iso-butyl- | —$CH_2OH$ | 4 -CN-Benzenesulfonyl | Naphthyl-2-$CH_2$ | H | 4 | |
| 54 | H | 4-$NH_2$ | Iso-butyl- | —$CH_2OH$ | 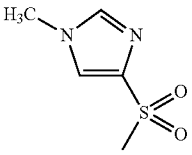 | Naphthyl-2-$CH_2$ | H | 4 | |

TABLE 1-continued

Structures of exemplary embodiments of HIV aspartyl protease inhibitors in accordance with this invention

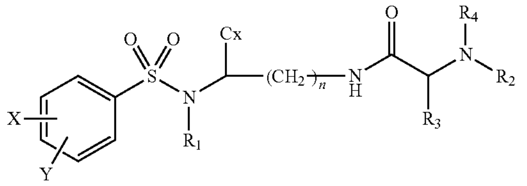

I

| | | | | | | | | |
|---|---|---|---|---|---|---|---|---|
| 55 | H | 4-$NH_2$ | Iso-butyl- | —$CH_2OH$ | 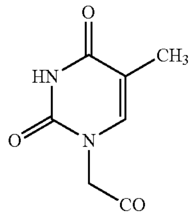 | Naphthyl-2-$CH_2$ | H | 4 |
| 56 | H | 4-$NH_2$ | Iso-butyl- | —$CH_2OH$ | 2-Pyridyl-$CH_2$— | Naphthyl-2-$CH_2$ | H | 4 |
| 57 | H | 4-$NH_2$ | Iso-butyl- | —$CH_2OH$ | Thiophene 2-$SO_2$ | $(C_6H_5)_2CH$ | H | 4 |
| 58 | H | 4-$NH_2$ | Iso-butyl- | —$CH_2OH$ | benzenesulfonyl | $(C_6H_5)_2CH$ | H | 4 |
| 59 | 4-F | 3-$NH_2$ | Iso-butyl- | —$CH_2OH$ | benzenesulfonyl | Naphthyl-2-$CH_2$ | H | 4 |
| 60 | 4-F | 3-$NH_2$ | Iso-butyl- | —$CH_2OH$ | Thiophene 2-$SO_2$ | Naphthyl-2-$CH_2$ | H | 4 |
| 61 | H | 4-$NH_2$ | Iso-butyl- | —$CH_2OH$ | 3-Picolyl-NH—CO | $(C_6H_5)_2CH$ | H | 4 |
| 62 | H | 4-$NH_2$ | Iso-butyl- | —$CH_2OH$ | 4-Picolyl-NH—CO | $(C_6H_5)_2CH$ | H | 4 |

| Ex. No. | X/Y | $R_1$ | Cx | $R_2$ | $R_3$ | $R_4$ | n | D, L, DL R, S, RS |
|---|---|---|---|---|---|---|---|---|
| 11 | 4-$NH_2$/H | i-$C_4H_9$ | —CH2OH | C6H5SO2 | Naphthyl-2-$CH_2$ | H | 4 | S, S |
| 12 | 4-$NH_2$/H | i-$C_4H_9$ | —CH2OH | Thiophene 2-SO2 | Naphthyl-1-$CH_2$ | H | 4 | S, S |
| 13 | 4-OCH2CH2-3 | i-$C_4H_9$ | —CH2OH | $CH_3O$—CO | 2-F-Phenyl-CH2 | H | 4 | S, RS |
| 14* | 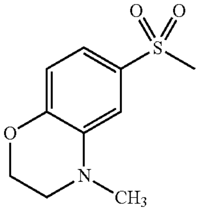 | i-$C_4H_9$ | —CH2OH | $CH_3O$—CO | 2-F-phenyl-CH2 | H | 4 | S, S |
| 15 | 4-OCH2CH2-3 | i-$C_4H_9$ | —CH2OH | 4-Morpholine-CO | Naphthyl-1-$CH_2$ | H | 4 | S, S |
| 16 | 4-OCH2CH2O-3 | i-$C_4H_9$ | —CH2OH | 4-Morpholine-CO | Naphthyl-1-$CH_2$ | H | 4 | S, S |
| 17 | 4-OCH2CH2-3 | i-$C_4H_9$ | —CH2OH | 4-Morpholine-CO | 2-Br$C_6H_4CH_2$ | H | 4 | S, S |
| 18 | 4-$NH_2$/H | i-$C_4H_9$ | —CH2OH | 3-OH—2Me—Ph—CO | 2-Br$C_6H_4CH_2$ | H | 4 | S, S |
| 19 | 4-$NH_2$/H | i-$C_4H_9$ | —CH2OH | 6-OH picoloyl | 2-Br$C_6H_4CH_2$ | H | 4 | S, S |
| 20 | 4-$NH_2$/H | i-$C_4H_9$ | —CH2OH | nicotinoyl | 2-Me—$C_6H_4CH_2$ | H | 4 | S, S |
| 21 | 4-$NH_2$/H | i-$C_4H_9$ | —CH2OH | 6-Me-Nicotinoyl | 2-Me—$C_6H_4CH_2$ | H | 4 | S.S |
| 22 | 4-$NH_2$/H | i-$C_4H_9$ | —CH2OH | 4-Pyridyl-CO | 2-Me—$C_6H_4CH_2$ | H | 4 | S, S |
| 23 | 4-$NH_2$/H | i-$C_4H_9$ | —CH2OH | 2-OH-3-Me-Phenyl-CO | 2-Me—$C_6H_4CH_2$ | H | 4 | S, S |
| 63 | 4-$NH_2$/H | i-$C_4H_9$ | —CH2OH | 3-OH-4-Me-Phenyl-CO | 2-Me—$C_6H_4CH_2$ | H | 4 | S, S |
| 24 | 4-$NH_2$/H | i-$C_4H_9$ | —CH2OH | $CH_3O$—CO | Cyclohexl-$CH_2$ | H | 4 | S, S |
| 25 | 4-$NH_2$/H | i-$C_4H_9$ | —CH2OH | Nicotinoyl | Cyclohexl-$CH_2$ | H | 4 | S, S |
| 26 | 4-$NH_2$/H | i-$C_4H_9$ | —CH2OH | 6-Me-Nicotinoyl | Cyclohexl-$CH_2$ | H | 4 | S, S |
| 27 | 8-quinoline sulfonyl | i-$C_4H_9$ | —CH2OH | $CH_3O$—CO | $(C_6H_5)_2CH$ | H | 4 | S, S |
| 28 | 3,4 methylene dioxy | i-$C_4H_9$ | —CH2OH | 6-OH-picoloyl | $(C_6H_5)_2CH$ | H | 4 | S, S |
| 29 | 4-$NH_2$/H | i-$C_4H_9$ | —CH2OH | 4-Pyridyl-CO | 2-Cl-Phenyl-$CH_2$ | H | 4 | S, S |
| 30 | 4-$NH_2$/H | i-$C_4H_9$ | —CH2OH | 2-Me-nicotinoyl | 2-Cl-Phenyl-$CH_2$ | H | 4 | S, S |
| 31 | 3,4(—OCH2CH2O—) | i-$C_4H_9$ | —CH2OH | 4-Morpholine-CO | (2-Br-Phenyl-$CH_2$ | H | 4 | S, S |
| 32 | 4-OCH2CH2-3 | i-$C_4H_9$ | —CH2OH | $CH_3O$—CO | $(C_6H_5)_2CH$ | H | 4 | S, S |
| 33 | 4-$NH_2$/H | CH2-3-Pyridyl | —CH2OH | $CH_3O$—CO | $(C_6H_5)_2CH$ | H | 4 | |
| 34 | 4-OCH2CH2-3 | i-$C_4H_9$ | —CH2OH | 4-Morpholine-CO | $(C_6H_5)_2CH$ | H | 4 | S, S |

TABLE 1-continued

Structures of exemplary embodiments of HIV aspartyl protease inhibitors in accordance with this invention

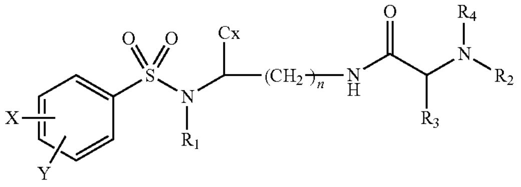

I

| | | | | | | | | |
|---|---|---|---|---|---|---|---|---|
| 35* | 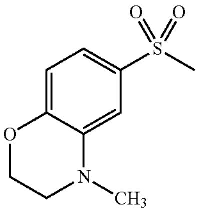 | i-$C_4H_9$ | —CH2OH | H | $(C_6H_5)_2CH$ | H | 4 | S, S |
| 36 | 4-$NH_2$/H | i-$C_4H_9$ | —CH2OH | 3- Me-2-pyridyl-CO | (2-Br-Phenyl-$CH_2$ | H | 4 | S, S |
| 37 | 4-$NH_2$/H | i-$C_4H_9$ | —CH2OH | 3-OH-4-Me-Phenyl-CO | (2-Br-Phenyl-$CH_2$ | H | 4 | S, S |
| 38 | 4-$NH_2$/H | i-$C_4H_9$ | —CH2OH | 4-PicolylO—CO | (2-Br-Phenyl-$CH_2$ | H | 4 | S, S |
| 39 | 4-$NH_2$/H | i-$C_4H_9$ | —CH2OH | 2-Me-Nicotinoyl | (2-Br-Phenyl-$CH_2$ | H | 4 | S, S |
| 40 | 4-$NH_2$/H | i-$C_4H_9$ | —CH2OH | 6-Me-Nicotinoyl | (2-Br-Phenyl-$CH_2$ | H | 4 | S, S |
| 41 | 4-$NH_2$/H | i-$C_4H_9$ | —CH2OH | piperonoyl | (2-Br-Phenyl-$CH_2$ | H | 4 | S, RS |
| 42 | 4-$NH_2$/H | i-$C_4H_9$ | —CH2OH | 4-Pyridyl-CO | (2-Br-Phenyl-$CH_2$ | H | 4 | S, S |
| 43 | 4-$NH_2$/H | i-$C_4H_9$ | —CH2OH | 5-Me-2-Piperazinoly | (2-Br-Phenyl-$CH_2$ | H | 4 | S, S |
| 44 | 4-$NH_2$/H | i-$C_4H_9$ | —CH2OH | 2-piperazine-CO | (2-Br-Phenyl-$CH_2$ | H | 4 | S, S |
| 45 | 4-$NH_2$/H | i-$C_4H_9$ | —CH2OH | 2-pyridine-CO | ((2-Br-Phenyl-$CH_2$ | H | 4 | S, S |
| 46 | 4-$NH_2$/H | i-$C_4H_9$ | —CH2OH | nicotinoyl | (2-Br-Phenyl-$CH_2$ | H | 4 | S, S |

*corresponds to R8 in formula II

TABLE 2

Exemplary embodiments of further HIV aspartyl protease inhibitors.

| Object ID | Structure | $KI_{—CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
|---|---|---|---|---|---|
| EX. 11 | 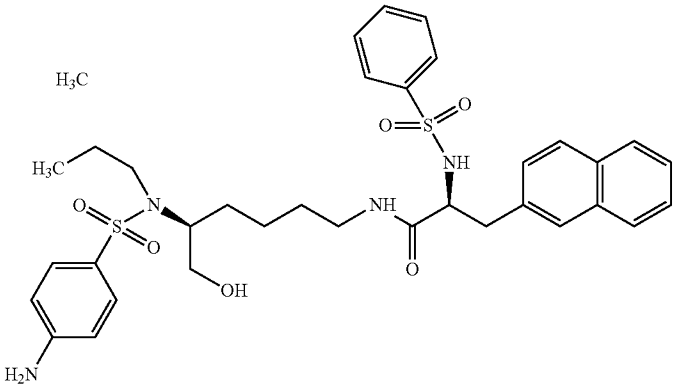 | 16.5 | | | 3200 |

TABLE 2-continued
| Object ID | Structure | KI_CALC ENZYME HIV-1 Protease nM | KI_GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| Exemplary embodiments of further HIV aspartyl protease inhibitors. | | | | | |
| EX. 12 | 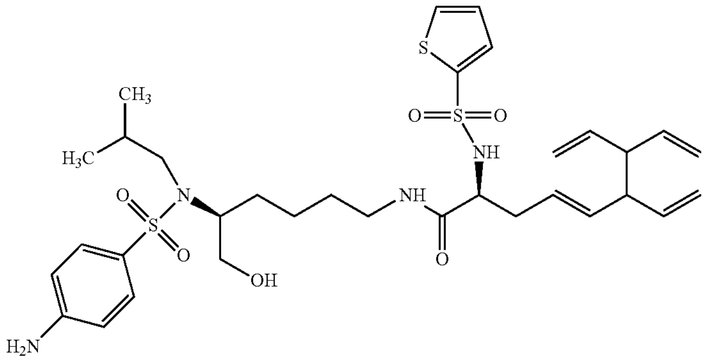 [SMILES: C=CC(C=C)C(C=C)/C=C/C[C@H](NS(=O)(=O)c1cccs1)C(=O)NCCCC[C@@H](CO)N(CC(C)C)S(=O)(=O)c1ccc(N)cc1] | 7.9 | | | 3000 |
| EX 47 | 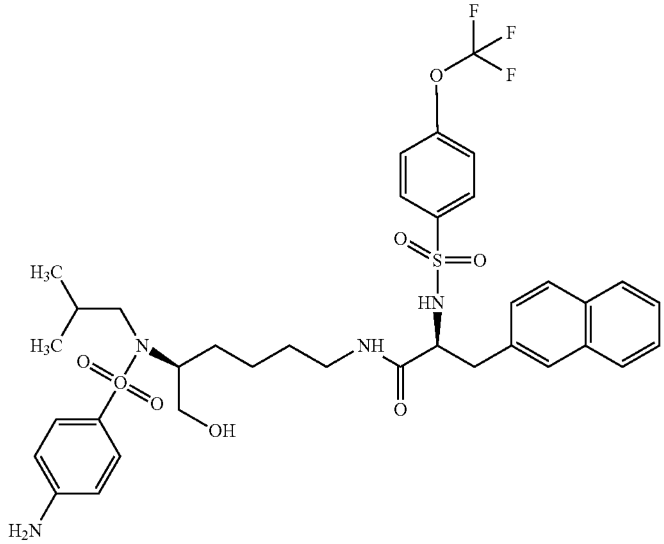 | 55.7 | | | |
| EX 48 | 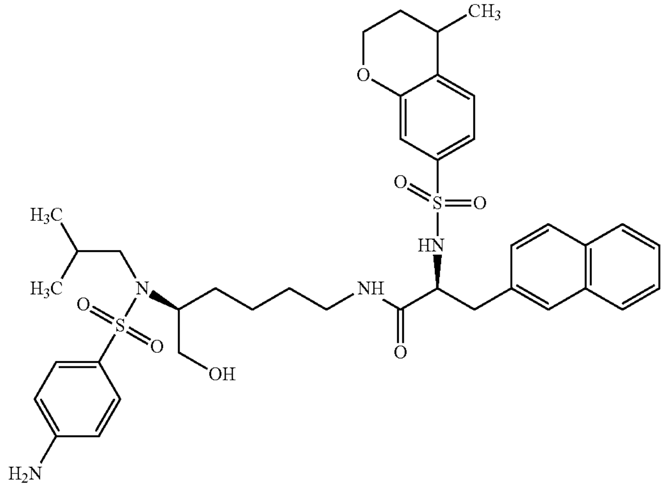 [SMILES: CC(C)CN([C@H](CO)CCCCNC(=O)[C@H](Cc1ccc2ccccc2c1)NS(=O)(=O)c1ccc2c(c1)OCCC2C)S(=O)(=O)c1ccc(N)cc1] | 5.1 | | 4.95 | 0.162 |

TABLE 2-continued
| Exemplary embodiments of further HIV aspartyl protease inhibitors. | | | | | |
|---|---|---|---|---|---|
| Object ID | Structure | $KI_{—CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
| EX 49 | 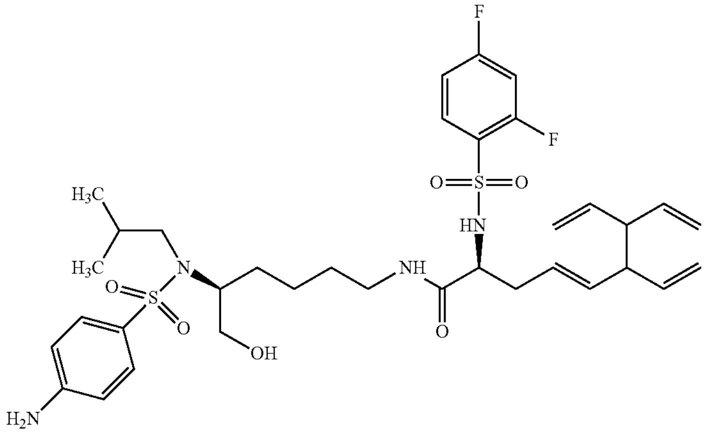 [SMILES: C=CC(C=C)C(C=C)/C=C/C[C@H](NS(=O)(=O)c1ccc(F)cc1F)C(=O)NCCCC[C@@H](CO)N(CC(C)C)S(=O)(=O)c1ccc(N)cc1] | 54.6 | | | |
| EX 50 | 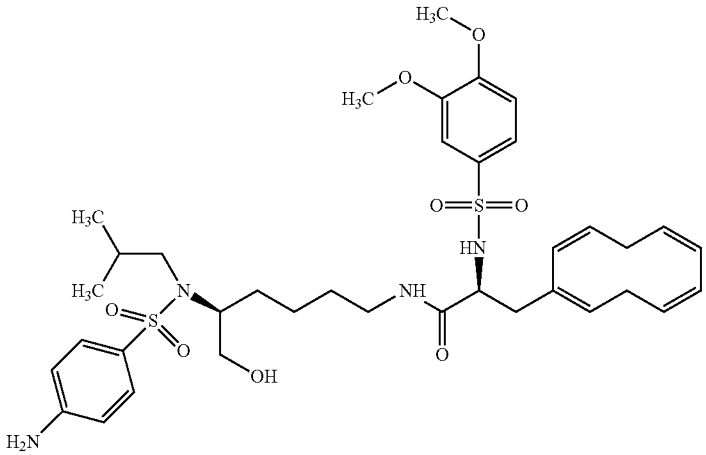 [SMILES: COc1ccc(S(=O)(=O)N[C@@H](CC2=C/C/C=C\C=C/C/C=C\2)C(=O)NCCCC[C@@H](CO)N(CC(C)C)S(=O)(=O)c2ccc(N)cc2)cc1OC] | 12.5 | | | |
| EX 51 | 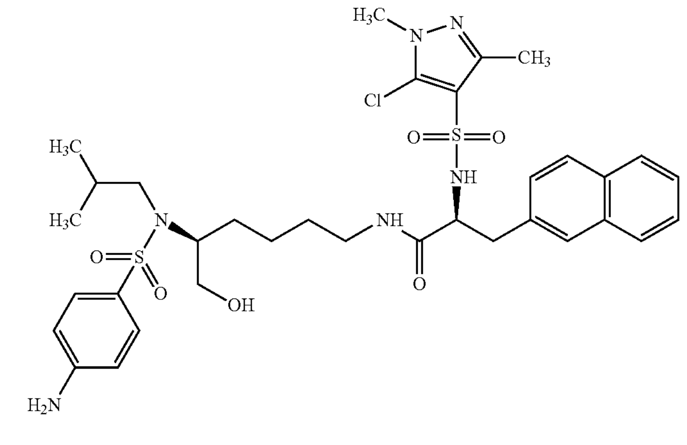 [SMILES: Cc1nn(C)c(Cl)c1S(=O)(=O)N[C@@H](Cc1ccc2ccccc2c1)C(=O)NCCCC[C@@H](CO)N(CC(C)C)S(=O)(=O)c1ccc(N)cc1] | 26.2 | | | |

TABLE 2-continued
| Object ID | Structure | KI_CALC ENZYME HIV-1 Protease nM | KI GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| Exemplary embodiments of further HIV aspartyl protease inhibitors. | | | | | |
| EX 52 | 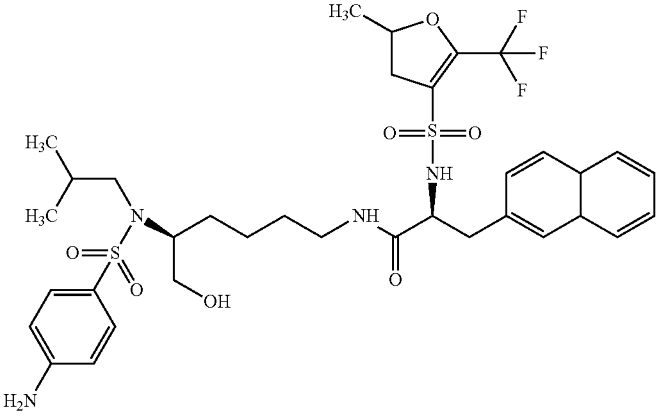 [SMILES: CC(C)CN([C@H](CO)CCCCNC(=O)[C@H](CC1=CC2C=CC=CC2C=C1)NS(=O)(=O)C1=C(C(F)(F)F)OC(C)C1)S(=O)(=O)c1ccc(N)cc1] | 247.9 | | | |
| EX 53 | 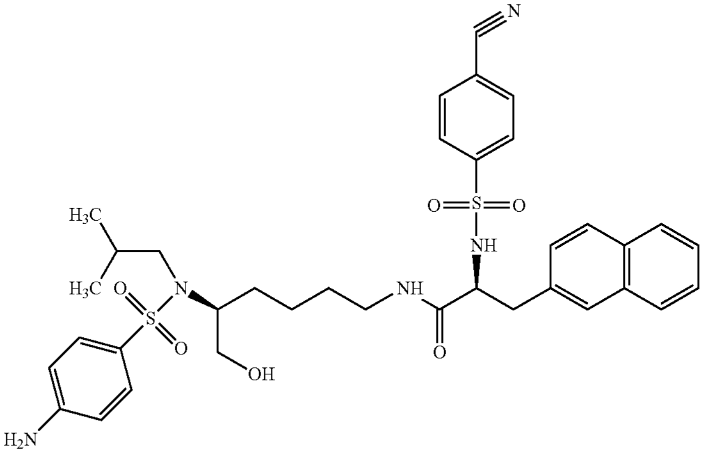 [SMILES: CC(C)CN([C@H](CO)CCCCNC(=O)[C@H](Cc1ccc2ccccc2c1)NS(=O)(=O)c1ccc(C#N)cc1)S(=O)(=O)c1ccc(N)cc1] | 37.4 | | | |
| EX 54 | 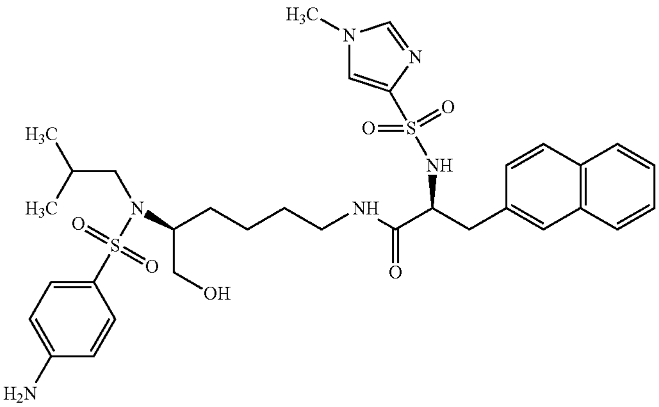 [SMILES: CC(C)CN([C@H](CO)CCCCNC(=O)[C@H](Cc1ccc2ccccc2c1)NS(=O)(=O)c1cn(C)cn1)S(=O)(=O)c1ccc(N)cc1] | 11.4 | | | |

TABLE 2-continued
Exemplary embodiments of further HIV aspartyl protease inhibitors.
| Object ID | Structure | $KI_{CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
|---|---|---|---|---|---|
| EX 55 | 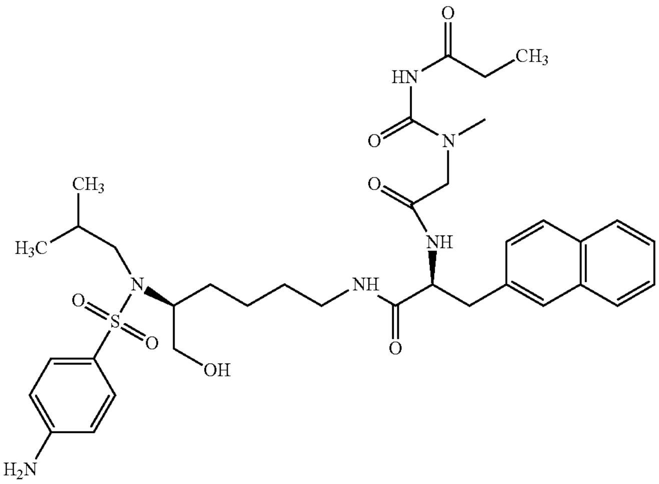 [SMILES: CCC(=O)NC(=O)N(C)CC(=O)N[C@@H](Cc1ccc2ccccc2c1)C(=O)NCCCC[C@@H](CO)N(CC(C)C)S(=O)(=O)c1ccc(N)cc1] | <3.8 | 0.788 | 0.878 | 1375 |
| EX 56 | 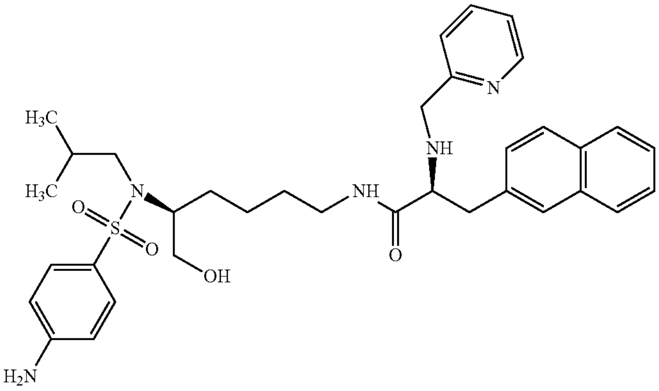 [SMILES: CC(C)CN([C@H](CO)CCCCNC(=O)[C@H](Cc1ccc2ccccc2c1)NCc1ccccn1)S(=O)(=O)c1ccc(N)cc1] | 4.9 | | 5.898 | >50000 |
| EX 57 | 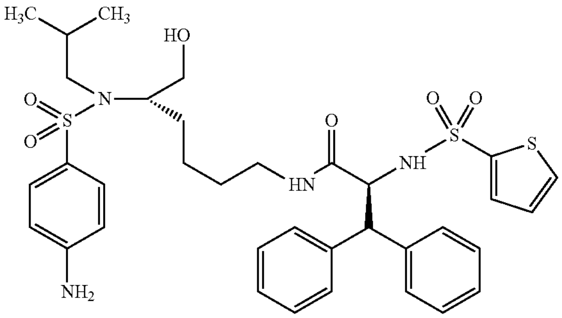 [SMILES: CC(C)CN([C@H](CO)CCCCNC(=O)[C@@H](NS(=O)(=O)c1cccs1)C(c1ccccc1)c1ccccc1)S(=O)(=O)c1ccc(N)cc1] | <3.8 | 0.541 | 0.601 | 64 |

TABLE 2-continued
| Object ID | Structure | KI__CALC ENZYME HIV-1 Protease nM | KI_GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| Exemplary embodiments of further HIV aspartyl protease inhibitors. | | | | | |
| EX 58 | 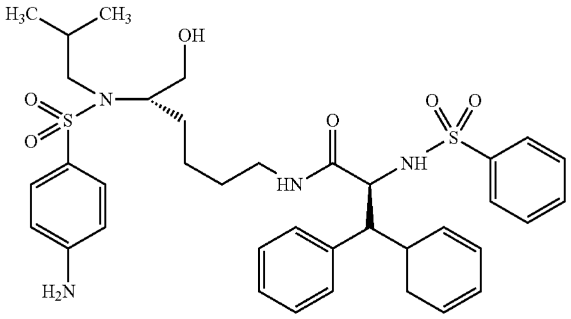 | <3.8 | 0.492 | 0.436 | 61 |
| EX 59 | 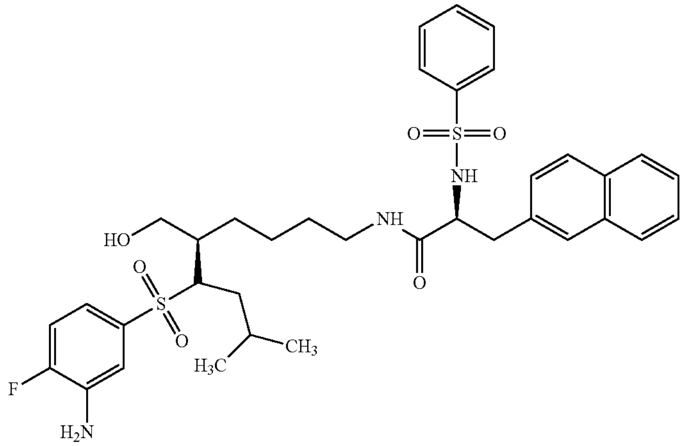 [SMILES: CC(C)CC([C@@H](CO)CCCCNC(=O)[C@H](Cc1ccc2ccccc2c1)NS(=O)(=O)c1ccccc1)S(=O)(=O)c1ccc(F)c(N)c1] | 24.6 | | | |
| EX 60 | 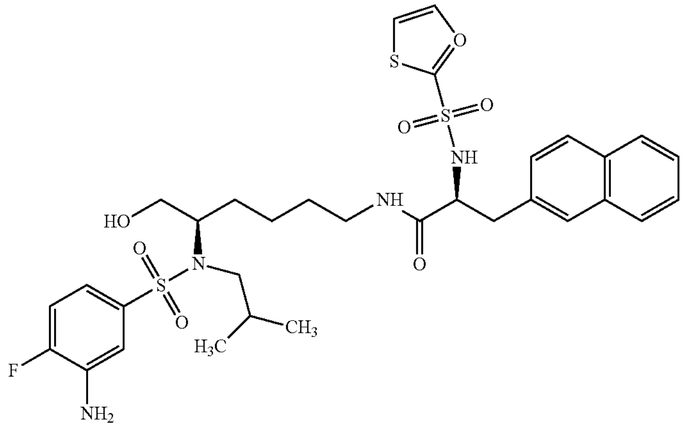 | 10.5 | | | >50000 |

TABLE 2-continued
Exemplary embodiments of further HIV aspartyl protease inhibitors.
| Object ID | Structure | KI_CALC ENZYME HIV-1 Protease nM | KI GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 61 | 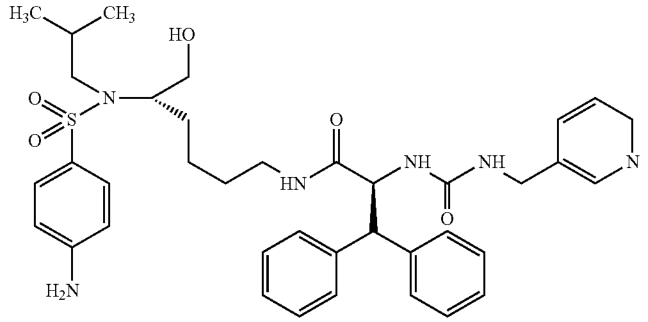 [SMILES: CC(C)CN([C@H](CO)CCCCNC(=O)[C@@H](NC(=O)NCC1=CNCC=C1)C(c1ccccc1)c1ccccc1)S(=O)(=O)c1ccc(N)cc1] | <3.8 | 0.473 | 0.465 | 171 |
| EX 62 | 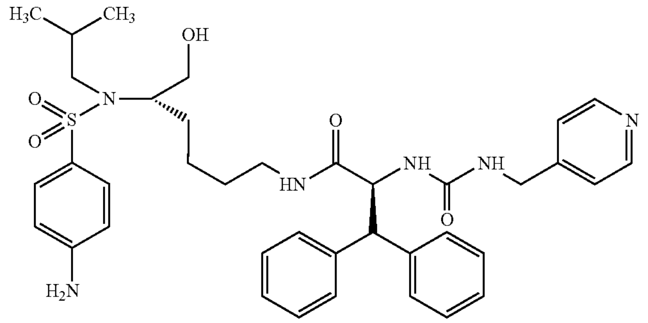 [SMILES: CC(C)CN([C@H](CO)CCCCNC(=O)[C@@H](NC(=O)NCc1ccncc1)C(c1ccccc1)c1ccccc1)S(=O)(=O)c1ccc(N)cc1] | <3.8 | 0.443 | 0.51 | 170 |
| EX. 7 | 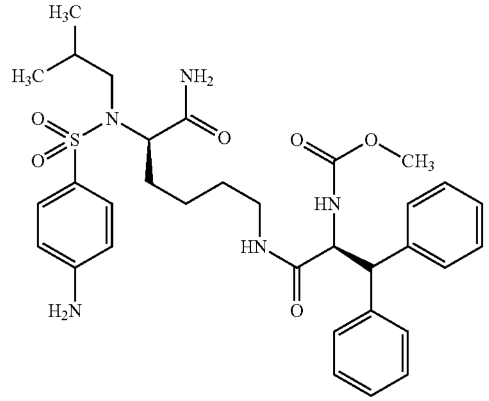 [SMILES: COC(=O)N[C@H](C(=O)NCCCC[C@H](C(N)=O)N(CC(C)C)S(=O)(=O)c1ccc(N)cc1)C(c1ccccc1)c1ccccc1] | | 0.049<br>0.042 | 0.652<br>0.507 | 30 |
| EX. 33 | 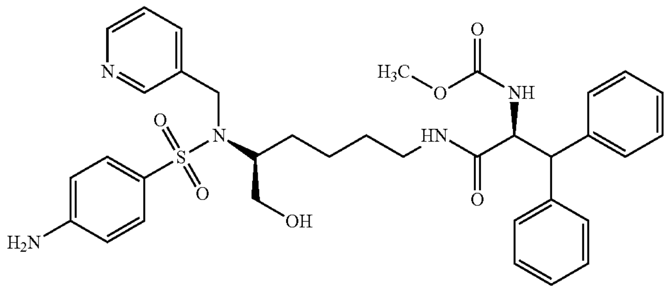 | <3.8 | | 1.007 | 196 |

TABLE 2-continued
Exemplary embodiments of further HIV aspartyl protease inhibitors.
| Object ID | Structure | $KI_{\_CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
|---|---|---|---|---|---|
| EX. 8 | 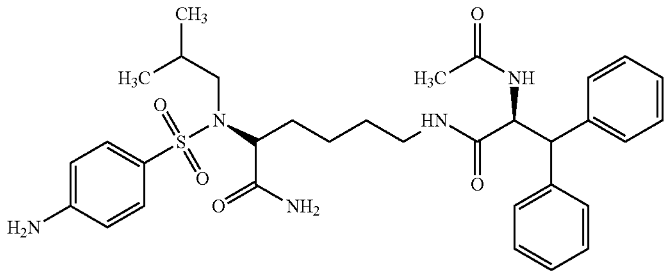 | <3.8 | | 1.073 | 238 |
| EX. 9 | 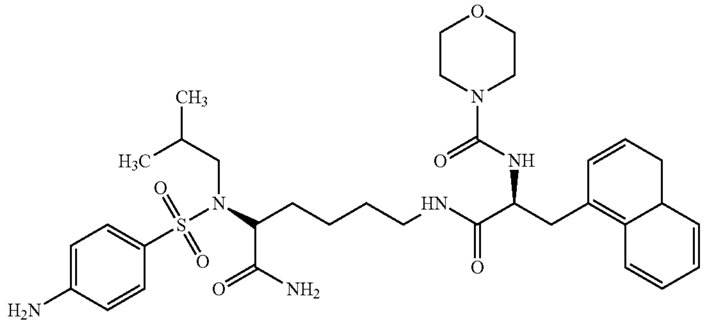 | <3.8 | 0.572 | 0.58 | 70 |
| EX. 10 | 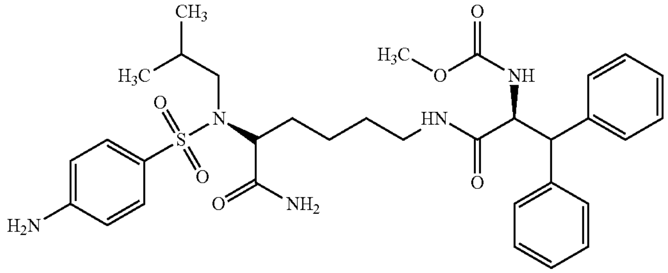 | | 0.79 | 1.08 | >50000 |
| EX. 44 | 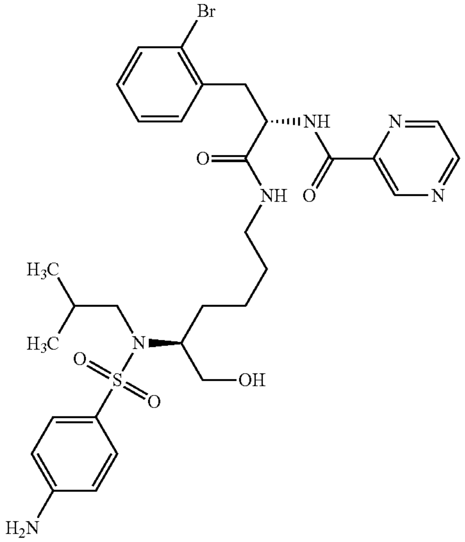 [SMILES: CC(C)CN([C@H](CO)CCCCNC(=O)[C@H](Cc1ccccc1Br)NC(=O)c1cnccn1)S(=O)(=O)c1ccc(N)cc1] | | 0.318 | 0.471 | 60 |

TABLE 2-continued
Exemplary embodiments of further HIV aspartyl protease inhibitors.
| Object ID | Structure | $KI_{\_CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
| --- | --- | --- | --- | --- | --- |
| EX. 45 | 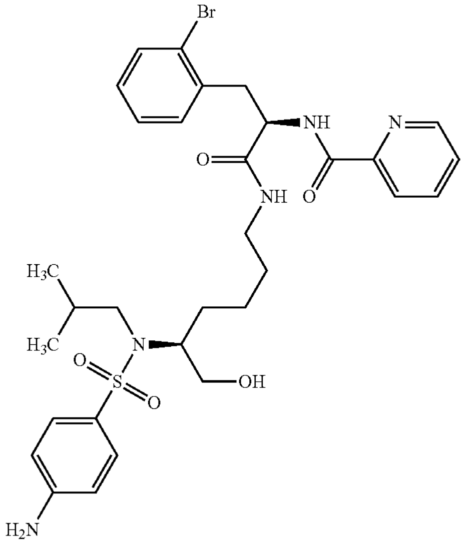 [SMILES: CC(C)CN([C@H](CO)CCCCNC(=O)[C@@H](Cc1ccccc1Br)NC(=O)c1ccccn1)S(=O)(=O)c1ccc(N)cc1] | | 0.429 | 0.615 | 197 |
| EX. 46 | 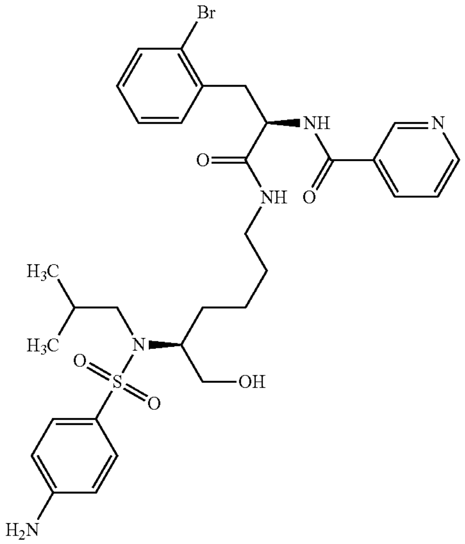 [SMILES: CC(C)CN([C@H](CO)CCCCNC(=O)[C@@H](Cc1ccccc1Br)NC(=O)c1cccnc1)S(=O)(=O)c1ccc(N)cc1] | | 0.119 | 0.372 | 58 |

TABLE 2-continued
| Exemplary embodiments of further HIV aspartyl protease inhibitors. | | | | | |
|---|---|---|---|---|---|
| Object ID | Structure | KI_CALC ENZYME HIV-1 Protease nM | KI GRAPHIC ENZYME HIV-1 Protease nM | IC50 ENZYME HIV-1 Protease nM | ANTI-HIV-EC50 VIRAL STRAIN NL4-3 nM |
| EX. 41 | 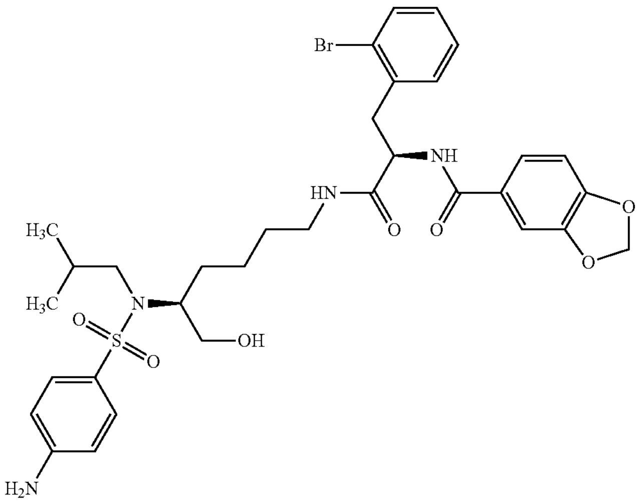 [SMILES: CC(C)CN([C@H](CO)CCCCNC(=O)[C@@H](Cc1ccccc1Br)NC(=O)c1ccc2c(c1)OCO2)S(=O)(=O)c1ccc(N)cc1] | | 0.05 | 0.336 | 43 |
| EX. 42 | 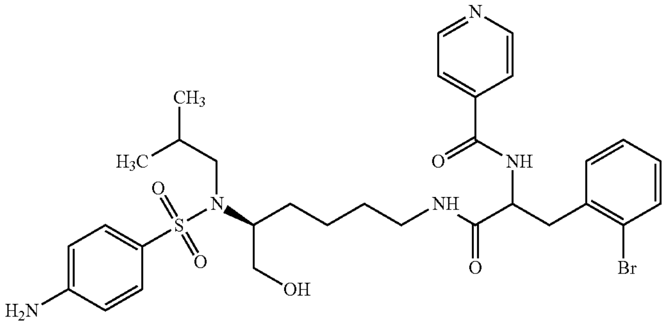 [SMILES: CC(C)CN([C@H](CO)CCCCNC(=O)C(Cc1ccccc1Br)NC(=O)c1ccncc1)S(=O)(=O)c1ccc(N)cc1] | <3.8 | 0.182 | 0.618 | 40 |
| EX. 39 | 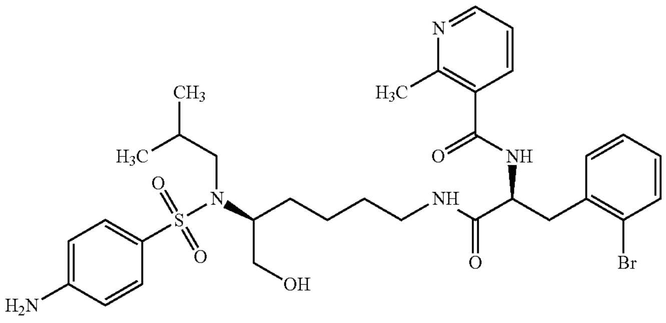 [SMILES: Cc1ncccc1C(=O)N[C@@H](Cc1ccccc1Br)C(=O)NCCCC[C@@H](CO)N(CC(C)C)S(=O)(=O)c1ccc(N)cc1] | <3.8 | 0.183 | 0.58 | 70 |

TABLE 2-continued
Exemplary embodiments of further HIV aspartyl protease inhibitors.
| Object ID | Structure | $KI_{\_CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
|---|---|---|---|---|---|
| EX. 40 | 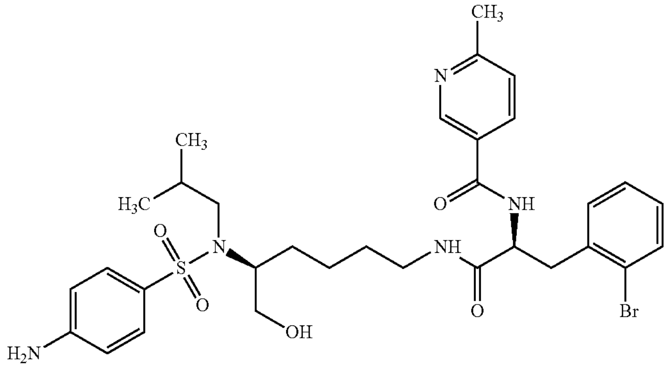 [SMILES: Cc1ccc(C(=O)N[C@@H](Cc2ccccc2Br)C(=O)NCCCC[C@@H](CO)N(CC(C)C)S(=O)(=O)c2ccc(N)cc2)cn1] | <3.8 | 0.217 | 0.567 | 55 |
| EX. 43 | 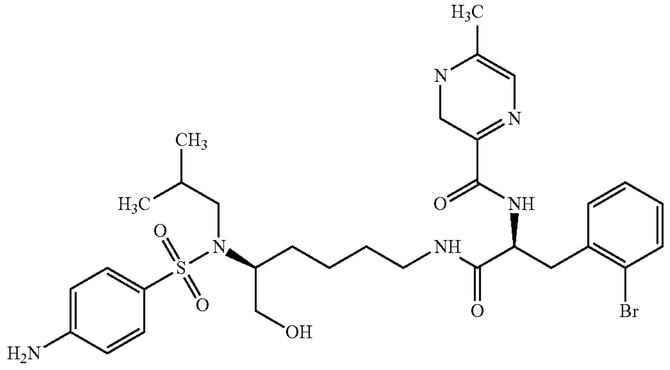 [SMILES: CC1=CN=C(C(=O)N[C@@H](Cc2ccccc2Br)C(=O)NCCCC[C@@H](CO)N(CC(C)C)S(=O)(=O)c2ccc(N)cc2)CN1] | <3.8 | 0.491 | 0.836 | 135 |
| EX. 2 This compound is the prodrug of EX 39 | 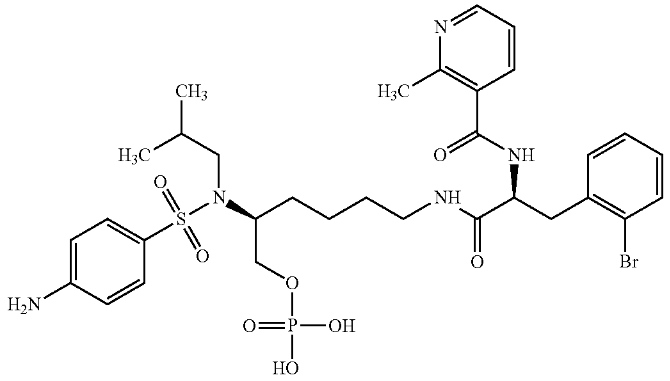 [SMILES: Cc1ncccc1C(=O)N[C@@H](Cc1ccccc1Br)C(=O)NCCCC[C@@H](COP(=O)(O)O)N(CC(C)C)S(=O)(=O)c1ccc(N)cc1] | >300.0 | | | |
| EX. 1 This compound is a prodrug of an active compound described in WO02/064551 | 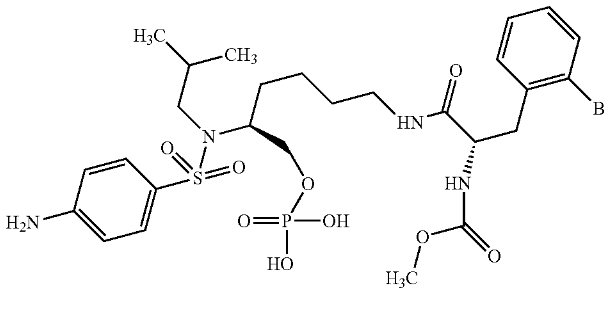 | >300.0 | | | |

TABLE 2-continued
| Exemplary embodiments of further HIV aspartyl protease inhibitors. | | | | | |
|---|---|---|---|---|---|
| Object ID | Structure | KI—CALC ENZYME HIV-1 Protease nM | KIGRAPHIC ENZYME HIV-1 Protease nM | IC50 ENZYME HIV-1 Protease nM | ANTI-HIV-EC50 VIRAL STRAIN NL4-3 nM |
| EX 3 This compound is a prodrug of EX 42 | 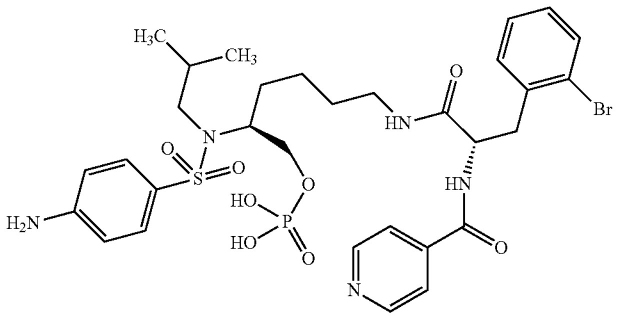 [SMILES: CC(C)CN([C@@H](CCCCNC(=O)[C@H](Cc1ccccc1Br)NC(=O)c1ccncc1)COP(=O)(O)O)S(=O)(=O)c1ccc(N)cc1] | >300.0 | | | |
| EX 4 Prodrug | 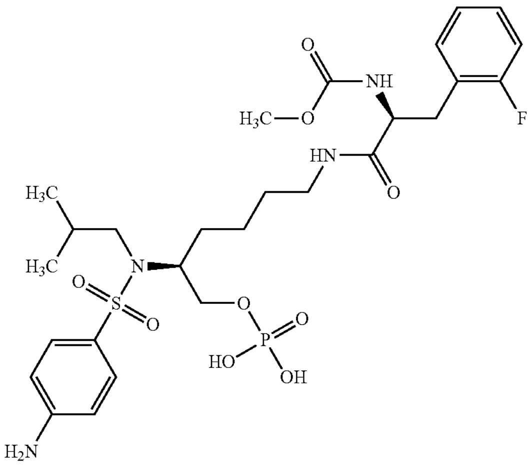 [SMILES: COC(=O)N[C@@H](Cc1ccccc1F)C(=O)NCCCC[C@@H](COP(=O)(O)O)N(CC(C)C)S(=O)(=O)c1ccc(N)cc1] | >300.0 | | | |
| EX 6 This compound is a prodrug of an active compound described in WO02/064551 | 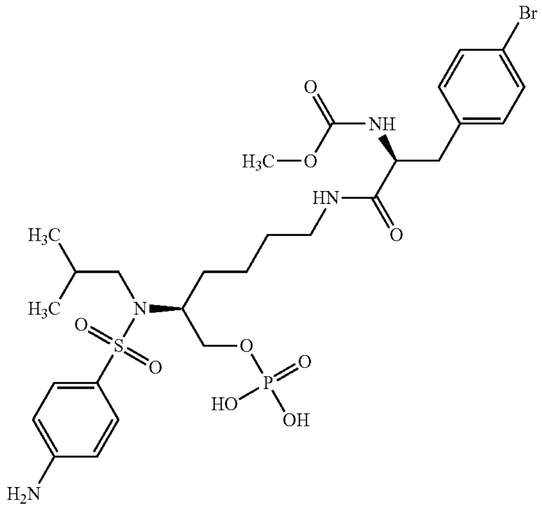 [SMILES: COC(=O)N[C@@H](Cc1ccc(Br)cc1)C(=O)NCCCC[C@@H](COP(=O)(O)O)N(CC(C)C)S(=O)(=O)c1ccc(N)cc1] | >300.0 | | | |

TABLE 2-continued
Exemplary embodiments of further HIV aspartyl protease inhibitors.
| Object ID | Structure | KI—CALC ENZYME HIV-1 Protease nM | KIGRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 36 | 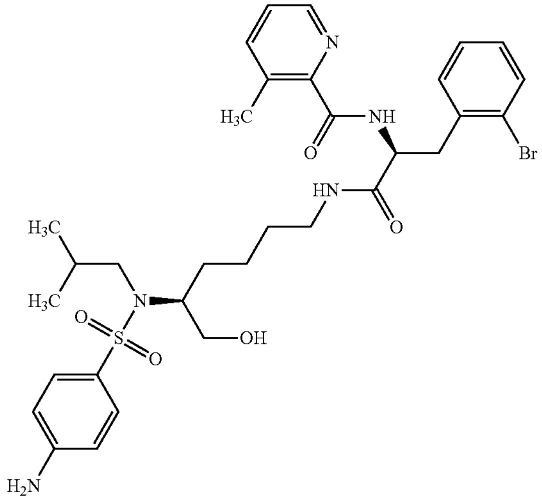 [SMILES: Cc1cccnc1C(=O)N[C@@H](Cc1ccccc1Br)C(=O)NCCCC[C@@H](CO)N(CC(C)C)S(=O)(=O)c1ccc(N)cc1] | <3.8 | 0.267 | 0.503 | 204 |
| EX 37 | 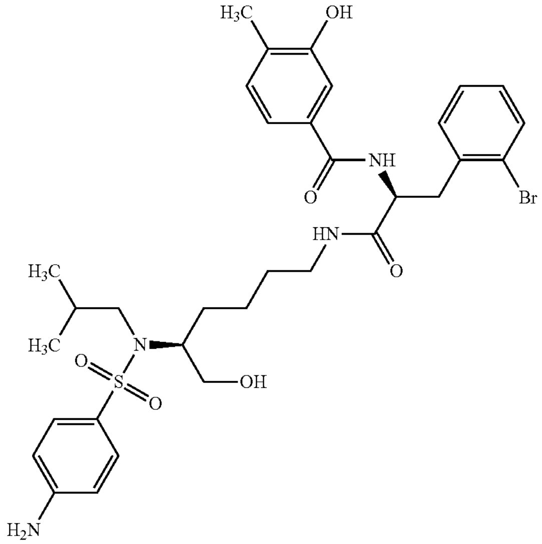 [SMILES: Cc1ccc(C(=O)N[C@@H](Cc2ccccc2Br)C(=O)NCCCC[C@@H](CO)N(CC(C)C)S(=O)(=O)c2ccc(N)cc2)cc1O] | <3.8 | 0.224 | 0.683 | 60 |
| EX 5 prodrug | 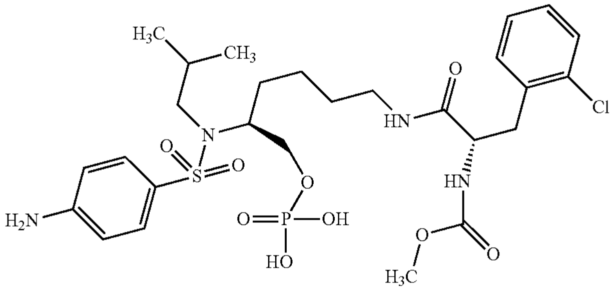 [SMILES: COC(=O)N[C@@H](Cc1ccccc1Cl)C(=O)NCCCC[C@@H](COP(=O)(O)O)N(CC(C)C)S(=O)(=O)c1ccc(N)cc1] | 91 | | | |

TABLE 2-continued
Exemplary embodiments of further HIV aspartyl protease inhibitors.
| Object ID | Structure | KI_CALC ENZYME HIV-1 Protease nM | KI_GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 38 | 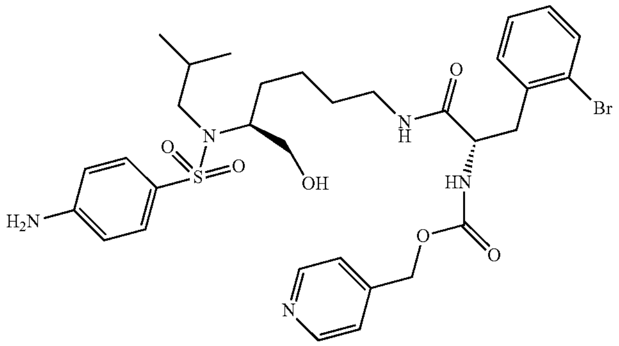 [SMILES: CC(C)CN([C@H](CO)CCCCNC(=O)[C@H](Cc1ccccc1Br)NC(=O)OCc1ccncc1)S(=O)(=O)c1ccc(N)cc1] | | 0.27 | 0.92 | 248 |
| EX 18 | 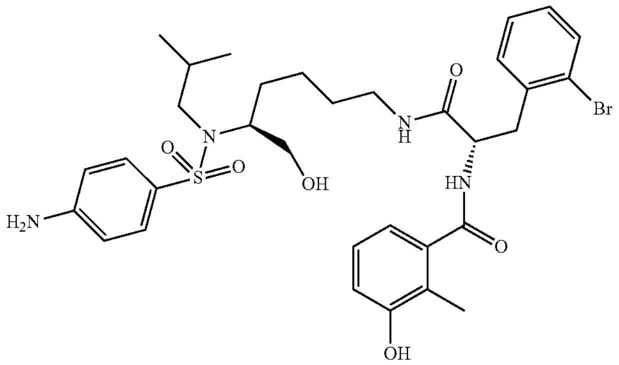 [SMILES: Cc1c(O)cccc1C(=O)N[C@@H](Cc1ccccc1Br)C(=O)NCCCC[C@@H](CO)N(CC(C)C)S(=O)(=O)c1ccc(N)cc1] | | 0.26 | 0.6 | 136 |
| EX 19 | 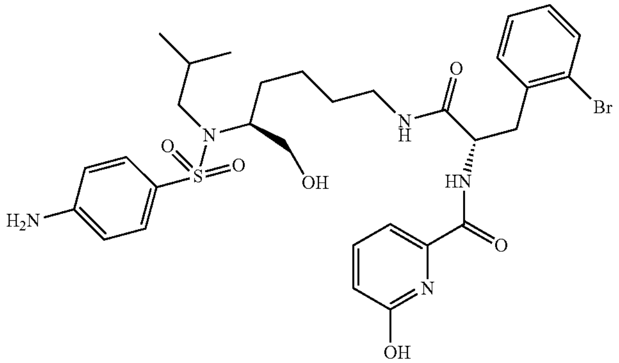 [SMILES: CC(C)CN([C@H](CO)CCCCNC(=O)[C@H](Cc1ccccc1Br)NC(=O)c1cccc(O)n1)S(=O)(=O)c1ccc(N)cc1] | | 0.27 | 0.29 | 99 |
| EX 13 | 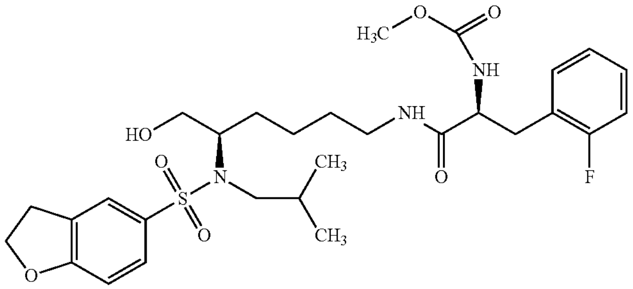 [SMILES: COC(=O)N[C@@H](Cc1ccccc1F)C(=O)NCCCC[C@H](CO)N(CC(C)C)S(=O)(=O)c1ccc2c(c1)CCO2] | 9.2 | | | 2135 |

TABLE 2-continued
Exemplary embodiments of further HIV aspartyl protease inhibitors.
| Object ID | Structure | KI_CALC ENZYME HIV-1 Protease nM | KI GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 14 | 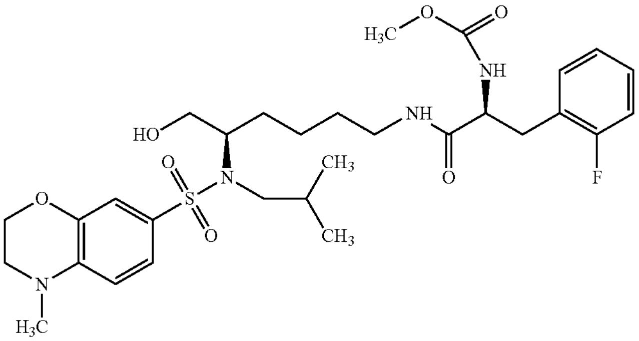 [SMILES: COC(=O)N[C@@H](Cc1ccccc1F)C(=O)NCCCC[C@H](CO)N(CC(C)C)S(=O)(=O)c1ccc2c(c1)OCCN2C] | 75.7 | | | 1832 |
| EX 15 | 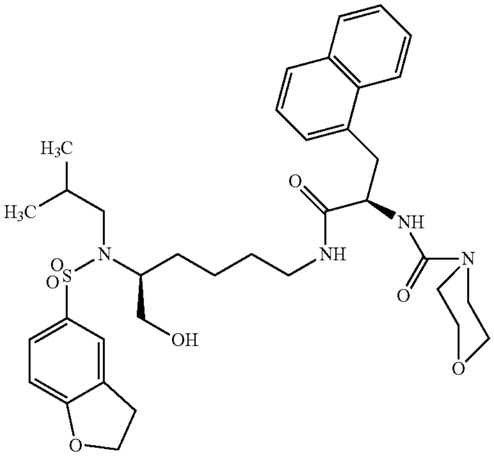 | <3.8 | 0.788 | 0.995 | 524 |
| EX 16 | 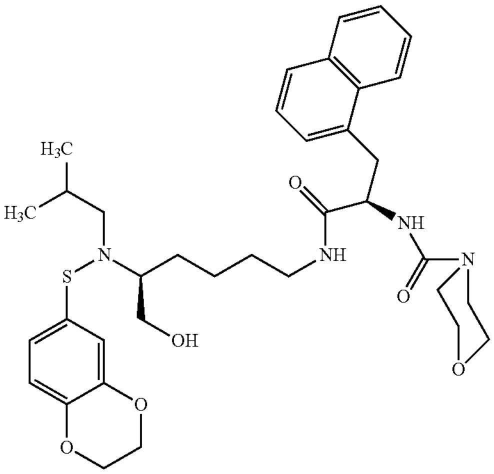 [SMILES: CC(C)CN(Sc1ccc2c(c1)OCCO2)[C@H](CO)CCCCNC(=O)[C@@H](Cc1cccc2ccccc12)NC(=O)N1CCOCC1] | <3.8 | | 2.024 | >50000 |

TABLE 2-continued
Exemplary embodiments of further HIV aspartyl protease inhibitors.
| Object ID | Structure | $KI_{\_CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
|---|---|---|---|---|---|
| EX 17 | 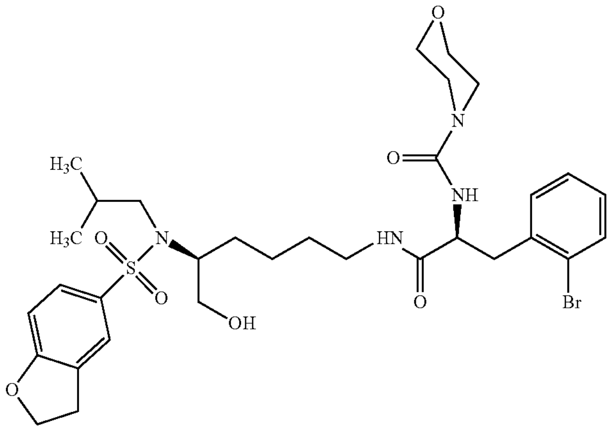 [SMILES: CC(C)CN([C@H](CO)CCCCNC(=O)[C@H](Cc1ccccc1Br)NC(=O)N1CCOCC1)S(=O)(=O)c1ccc2c(c1)CCO2] | <3.8 | 1.000<br>1.026 | 0.599 | 665 |
| EX 31 | 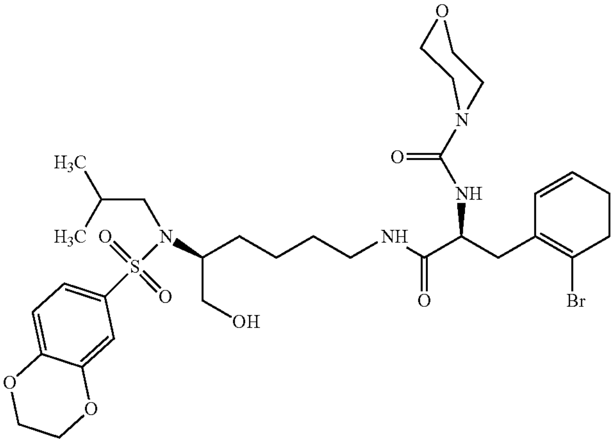 [SMILES: CC(C)CN([C@H](CO)CCCCNC(=O)[C@H](CC1=C(Br)CCC=C1)NC(=O)N1CCOCC1)S(=O)(=O)c1ccc2c(c1)OCCO2] | <3.8 | | 3.659 | 980 |
| EX 32 | 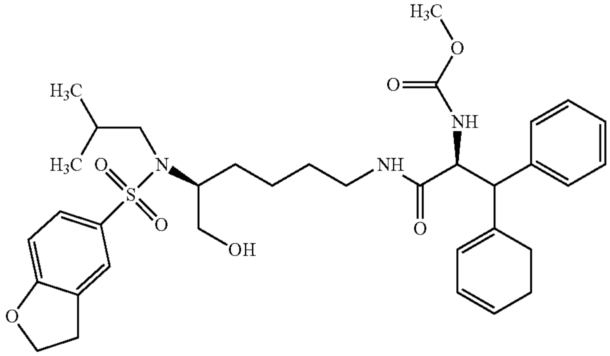 [SMILES: COC(=O)N[C@H](C(=O)NCCCC[C@@H](CO)N(CC(C)C)S(=O)(=O)c1ccc2c(c1)CCO2)C(C1=CC=CCC1)c1ccccc1] | <3.8 | 0.781 | 0.899 | 151 |

TABLE 2-continued
Exemplary embodiments of further HIV aspartyl protease inhibitors.
| Object ID | Structure | KI_CALC ENZYME HIV-1 Protease nM | KI_GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 34 | 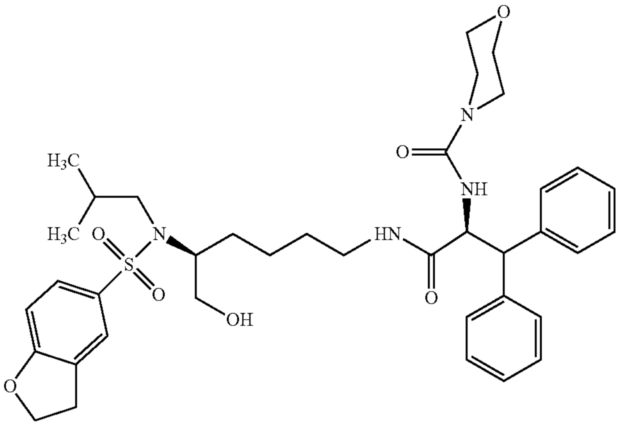 [SMILES: CC(C)CN([C@H](CO)CCCCNC(=O)[C@@H](NC(=O)N1CCOCC1)C(c1ccccc1)c1ccccc1)S(=O)(=O)c1ccc2c(c1)CCO2] | <3.8 | 0.821 | 0.963 | 1000 |
| EX 35 | 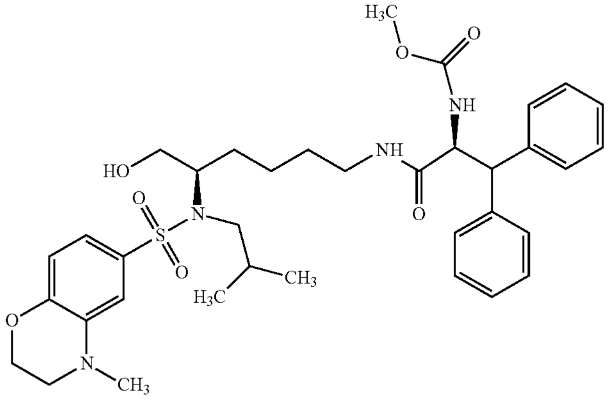 [SMILES: COC(=O)N[C@H](C(=O)NCCCC[C@H](CO)N(CC(C)C)S(=O)(=O)c1ccc2c(c1)N(C)CCO2)C(c1ccccc1)c1ccccc1] | <3.8 | | 3.011 | >50000 |
| EX 27 | 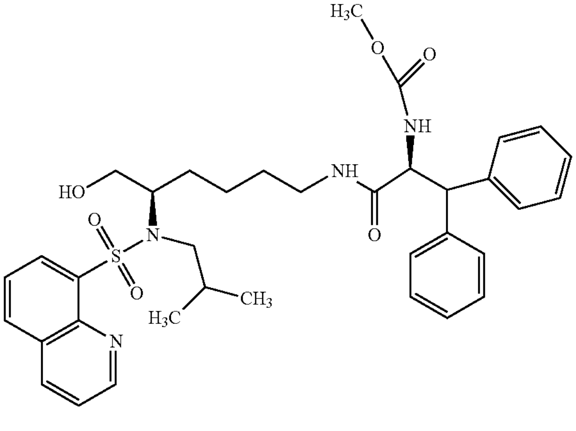 [SMILES: COC(=O)N[C@H](C(=O)NCCCC[C@H](CO)N(CC(C)C)S(=O)(=O)c1cccc2cccnc12)C(c1ccccc1)c1ccccc1] | <3.8 | | 2.55 | 369 |

TABLE 2-continued
Exemplary embodiments of further HIV aspartyl protease inhibitors.
| Object ID | Structure | $KI_{—CALC}$ ENZYME HIV-1 Protease nM | $KI_{GRAPHIC}$ ENZYME HIV-1 Protease nM | IC50 ENZYME HIV-1 Protease nM | ANTI-HIV-EC50 VIRAL STRAIN NL4-3 nM |
|---|---|---|---|---|---|
| EX 28 | 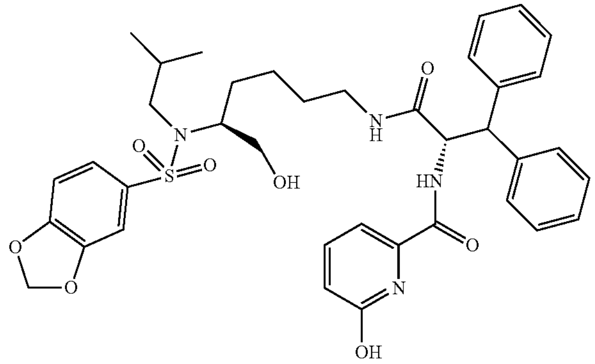 [SMILES: CC(C)CN([C@H](CO)CCCCNC(=O)[C@@H](NC(=O)c1cccc(O)n1)C(c1ccccc1)c1ccccc1)S(=O)(=O)c1ccc2c(c1)OCO2] | | 0.47 | | |
| EX 29 | 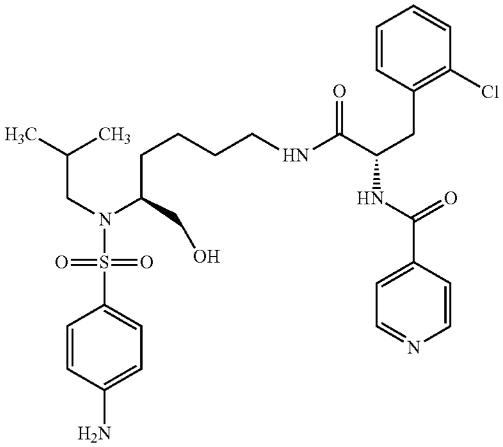 [SMILES: CC(C)CN([C@H](CO)CCCCNC(=O)[C@H](Cc1ccccc1Cl)NC(=O)c1ccncc1)S(=O)(=O)c1ccc(N)cc1] | <3.8 | | 3.81 | 144 |
| EX 30 | 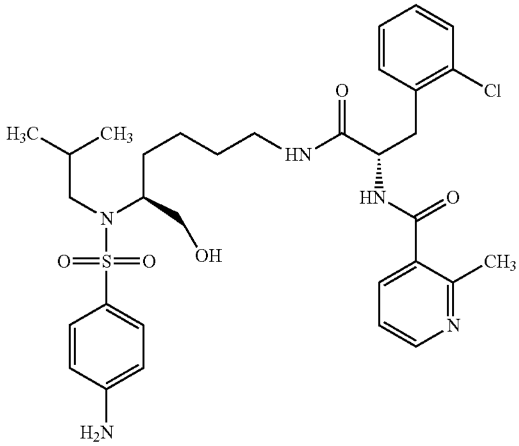 [SMILES: Cc1ncccc1C(=O)N[C@@H](Cc1ccccc1Cl)C(=O)NCCCC[C@@H](CO)N(CC(C)C)S(=O)(=O)c1ccc(N)cc1] | <3.8 | | 2.15 | 422 |

TABLE 2-continued
Exemplary embodiments of further HIV aspartyl protease inhibitors.
| Object ID | Structure | KI_CALC ENZYME HIV-1 Protease nM | KI GRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 20 | 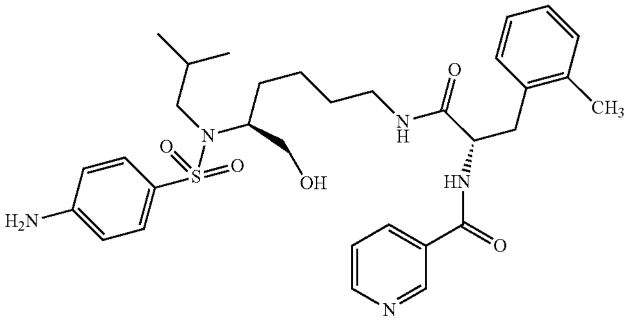 [SMILES: Cc1ccccc1C[C@H](NC(=O)c1cccnc1)C(=O)NCCCC[C@@H](CO)N(CC(C)C)S(=O)(=O)c1ccc(N)cc1] | <3.8 | | 1.417 | 148 |
| EX 21 | 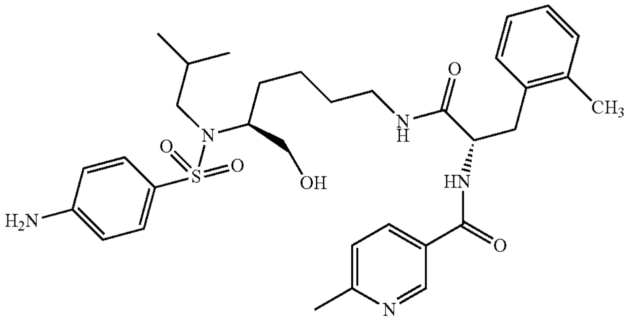 [SMILES: Cc1ccc(C(=O)N[C@@H](Cc2ccccc2C)C(=O)NCCCC[C@@H](CO)N(CC(C)C)S(=O)(=O)c2ccc(N)cc2)cn1] | <3.8 | | 1.286 | 198 |
| EX 22 | 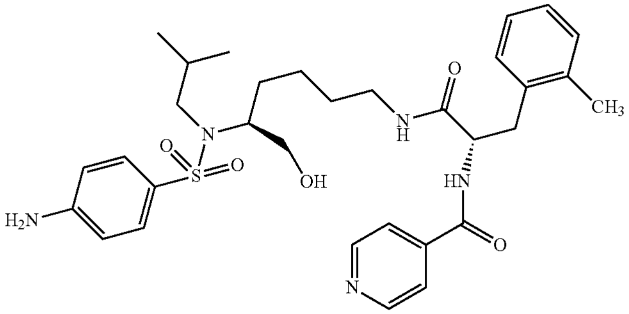 [SMILES: Cc1ccccc1C[C@H](NC(=O)c1ccncc1)C(=O)NCCCC[C@@H](CO)N(CC(C)C)S(=O)(=O)c1ccc(N)cc1] | <3.8 | | 1.353 | 158 |
| EX 23 | 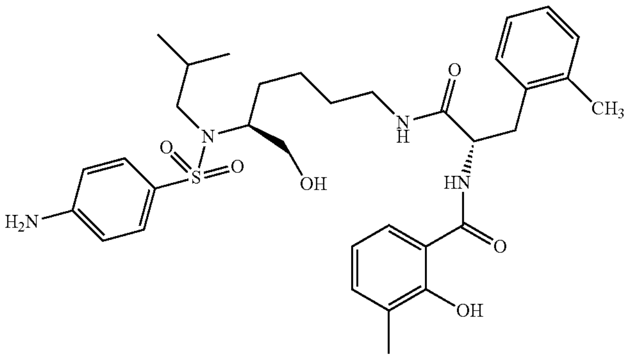 [SMILES: Cc1ccccc1C[C@H](NC(=O)c1cccc(C)c1O)C(=O)NCCCC[C@@H](CO)N(CC(C)C)S(=O)(=O)c1ccc(N)cc1] | <3.8 | | 4.122 | >50000 |

TABLE 2-continued
Exemplary embodiments of further HIV aspartyl protease inhibitors.
| Object ID | Structure | KI—CALC ENZYME HIV-1 Protease nM | KIGRAPHIC ENZYME HIV-1 Protease nM | IC50 ENZYME HIV-1 Protease nM | ANTI-HIV-EC50 VIRAL STRAIN NL4-3 nM |
|---|---|---|---|---|---|
| EX 63 | 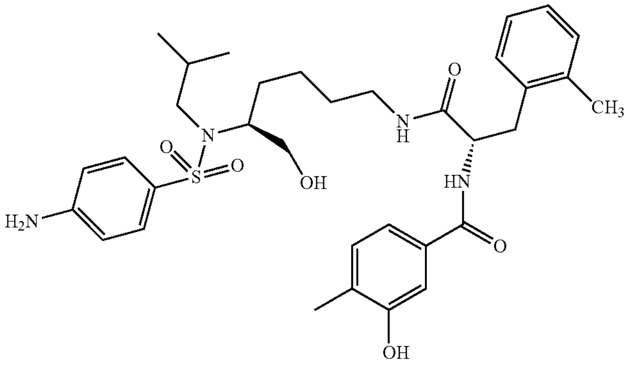 [SMILES: Cc1ccc(C(=O)N[C@@H](Cc2ccccc2C)C(=O)NCCCC[C@@H](CO)N(CC(C)C)S(=O)(=O)c2ccc(N)cc2)cc1O] | <3.8 | | 0.938 | 165 |
| EX 24 | 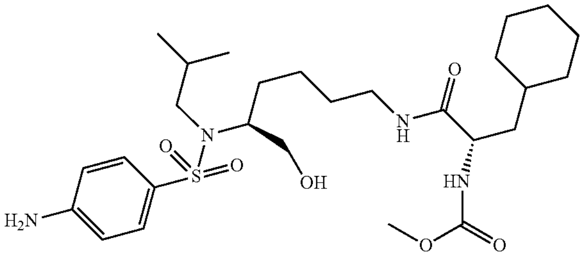 [SMILES: COC(=O)N[C@@H](CC1CCCCC1)C(=O)NCCCC[C@@H](CO)N(CC(C)C)S(=O)(=O)c1ccc(N)cc1] | 5.3 | | 5.212 | >5000 |
| EX 25 | 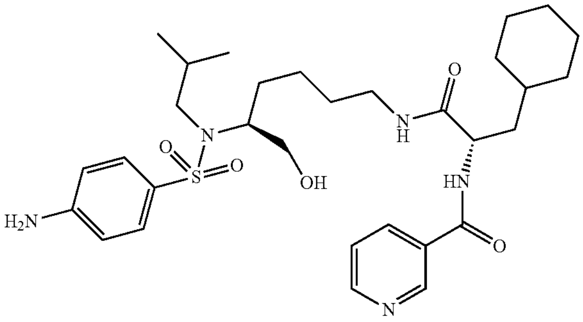 [SMILES: CC(C)CN([C@H](CO)CCCCNC(=O)[C@H](CC1CCCCC1)NC(=O)c1cccnc1)S(=O)(=O)c1ccc(N)cc1] | <3.8 | | 2.876 | >5000 |
| EX 26 | 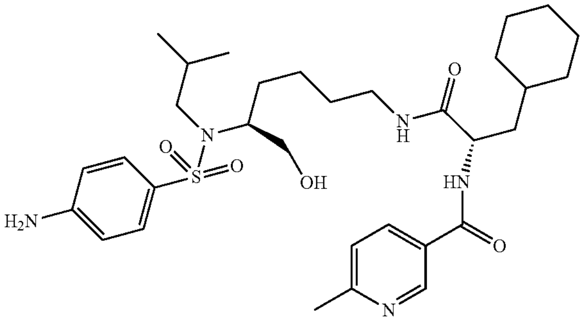 [SMILES: Cc1ccc(C(=O)N[C@@H](CC2CCCCC2)C(=O)NCCCC[C@@H](CO)N(CC(C)C)S(=O)(=O)c2ccc(N)cc2)cn1] | <3.8 | | 3.314 | >5000 |

We claim:
1. A compound having the formula:
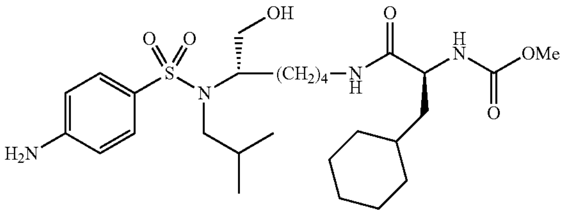
or a pharmaceutically acceptable salt thereof or a stereoisomer thereof.
* * * * *